United States Patent [19]
Mjalli et al.

[11] Patent Number: 5,840,721
[45] Date of Patent: *Nov. 24, 1998

[54] IMIDAZOLE DERIVATIVES AS MDR MODULATORS

[75] Inventors: Adnan M. M. Mjalli, Louisville, Ky.; Chengzhi Zhang, San Diego, Calif.

[73] Assignee: Ontogen Corporation, Carlsbad, Calif.

[*] Notice: The term of this patent shall not extend beyond the expiration date of Pat. Nos. 5,700,826 and 5,756,527.

[21] Appl. No.: 951,695

[22] Filed: Oct. 16, 1997

Related U.S. Application Data

[63] Continuation-in-part of Ser. No. 890,911, Jul. 9, 1997, abandoned.

[51] Int. Cl.⁶ .................. A61K 31/415; C07D 233/56; C07D 233/04; C07D 233/02; C07D 233/61
[52] U.S. Cl. .................. 514/232.2; 514/235.8; 514/255; 514/341; 514/367; 514/375; 544/111; 544/138; 544/139; 544/370; 546/44; 546/210; 548/152; 548/217; 548/159; 548/312.7; 548/241.5; 548/314.7; 548/315.4; 548/335.5; 548/340.1; 548/341.5; 548/343.5
[58] Field of Search .................. 548/159, 217, 548/315.4, 335.5, 338.1, 241.5, 340.1, 343.5, 341.5, 341.1, 152, 314.7, 312.7; 546/94, 210; 544/138, 139, 111, 370; 514/397, 398, 399, 232.2, 235.8, 367, 255, 341

[56] References Cited

U.S. PATENT DOCUMENTS

| | | |
|---|---|---|
| 2,801,243 | 7/1957 | Hanslick et al. .................. 548/315.4 X |
| 3,361,755 | 1/1968 | Green .................. 548/343.5 X |
| 3,558,645 | 1/1971 | Griot .................. 548/343.5 X |
| 3,707,475 | 12/1972 | Lombardino .................. 548/343.5 X |
| 3,784,557 | 1/1974 | Cescon .................. 548/343.5 X |
| 4,160,452 | 7/1979 | Theeuwes .................. 128/260 |
| 4,256,108 | 3/1981 | Theeuwes .................. 128/260 |
| 4,265,874 | 5/1981 | Bonsen et al. .................. 424/15 |
| 4,424,229 | 1/1984 | Jorgensen et al. .................. 548/343.5 X |
| 4,632,930 | 12/1986 | Carini et al. .................. 514/365 |
| 4,665,023 | 5/1987 | Deneke et al. .................. 435/28 |
| 4,914,096 | 4/1990 | Houlihan et al. .................. 514/220 |
| 5,274,095 | 12/1993 | Braun et al. . | |
| 5,292,699 | 3/1994 | Guder et al. . | |
| 5,296,609 | 3/1994 | McCort et al. . | |
| 5,312,828 | 5/1994 | Finkelstein et al. . | |
| 5,700,826 | 12/1997 | Mjalli et al. . | |

FOREIGN PATENT DOCUMENTS

| | | | |
|---|---|---|---|
| 0044486 | 1/1982 | European Pat. Off. ......... | 548/335.2 |
| 0582164 | 2/1994 | European Pat. Off. ......... | 548/343.5 |
| 3835195 | 4/1990 | Germany ......... | 548/343.5 |
| 42-006750 | 3/1967 | Japan ......... | 548/335.5 |
| 61-174267 | 8/1986 | Japan ......... | 548/343.5 |
| 61-229868 | 10/1986 | Japan ......... | 548/343.5 |
| 63-208570 | 8/1988 | Japan ......... | 548/343.5 |
| 1-117867 | 5/1989 | Japan ......... | 548/343.5 |
| 3-232861 | 10/1991 | Japan ......... | 548/343.5 |
| 4-279569 | 10/1992 | Japan ......... | 548/343.5 |
| 0454154 | 6/1968 | Switzerland ......... | 548/343.5 |
| 93/14081 | 7/1983 | WIPO ......... | 548/343.5 |
| 93/14082 | 7/1993 | WIPO ......... | 548/343.5 |

OTHER PUBLICATIONS

Engel et al, Liebigs Am. Chem., vol. of 1978, pp. 1916 to 1927.
Matsuda et al, Chemistry Letters, vol. of 1977, pp. 1456 to 1460.
Novelli et al, Terahedron Letters, No. 3, pp. 256 to 269 (1967).
Palkowitz et al, J. Med. Chem., vol. 37, pp. 4508 to 4521 (1994).
Salimbeni et al, J. Med. Chem., vol. 37, pp. 3928 To 3938 (1994).
Bradley et al., P–Glycoprotein Expression in Multidrug–resistant Human Ovarian Carinoma Cell Lines, *Cancer Research*, May 15, 1989, 2790–2796, 49.
Raderer and Scheithaurer, Clinical Trials of Agents that Reverse Multidrug Resistance, *Cancer*, Dec. 15, 1993, 3553–3563, 72–12.
Juranka et al., P–glycoprotein: multidrug–resistance and a superfamily of membrane–associated transport proteins, *The FASEB Journal*, Dec. 1989, 2583–2592, 3.
Krishnamachary and Center, The MRP Gene Associated with a Non–P–glycoprotein Multidrug Resistance Encodes a 190–kDa Membrane Bound Glycoprotein, *Cancer Research*, Aug. 15, 1993, 3658–3661, 53.
Leyland–Jones et al., Reversal of Multidrug Resistance to Cancer Chemotherapy, *Cancer Supplement*, Dec. 1, 1993, 3484–3488, 72–11.
Lum et al., Clinical Trials of Modulation of Multidrug Resistance, *Cancer Supplement*, Dec. 1, 1993, 3502–3514, 72–11.
Krieg and Manecke, Synthese und Halbleitereigenschaften arylsubstituierter Imidazole, *A. Naturforschg teil*, Sep. 1966, 132–141, 22b.
Bader et al., Nucleophilic Displacements of Activated Fluorine in Aromatic Compounds, *J. Organic Chemistry*, Jul. 1966, 2319–2321, 31.
Garro–Helion, et al., Mild and Selective Palladium(O)–Catalyzed Deallylation of Allylic Amines, *J. Organic Chemistry*, 1993, 6109–6113, 58–22.
Patel et al., Palladium–Catalyzed Vinylic Substitution Reactions with Carboxylic Acid Derivatives, *J. Organic Chemistry*, 1977, 3903–3907, 42–24.

*Primary Examiner*—Floyd D. Higel
*Attorney, Agent, or Firm*—Frank S. Chow

[57] ABSTRACT

The present invention relates to polysubsituted imidazole having formula 1

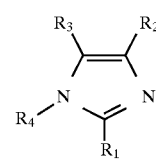

Formula 1

These compounds are useful for restoring the sensitivity of multidrug resistant cells to cancer chemotherapeutic agents.

74 Claims, No Drawings

IMIDAZOLE DERIVATIVES AS MDR MODULATORS

This is a continuation-in-part application of our co-pending application Ser. No 08/890,911 filed on Jul. 09, 1997 now abandoned, the disclosure of which is incorporated herein by reference.

FIELD OF THE INVENTION

The present invention provides novel imidazole derivatives, novel pharmaceutical compositions containing same, methods of their use, and methods of their manufacture. Such compounds are pharmacologically useful for restoring the sensitivity of multidrug resistant cells to cancer chemotherapeutic agents.

BACKGROUND OF THE INVENTION

A major problem in the treatment of cancer is the emergence of tumor cell resistance to chemotherapeutic agents and the subsequent patient relapse (Bradley et al.*J, Cancer Res.* 1989, 49, 2790–2796; Raderer and Sscheitharer, *Cancer* 1993, 72, 3553–3563). These cancer victims may fail to respond to any antitumor agent, since these tumor cells tend to exhibit clinical resistance to many drugs. This phenomenon is known as multi-drug resistance (MDR). MDR is associated with certain alterations in tumor cells resulting in reduced intracellular anticancer drug accumulation, including reduced membrane permeability and increased removal of drug from the cell via an energy-dependent efflux mechanism. Studies of this mechanism have led to the characterization of genes capable of conferring resistance to chemotherapeutic agents. One of these genes, the P-glycoprotein or MDR1 gene, has been strongly implicated since overexpression of this gene can lead to resistance to anthracyclines, vinca alkaloids, and podophyllins, all important chemotherapeutic agents. MDR1 encodes a 170 kDa membrane alycoporotein (gp-170 or Pgp) that acts as an ATP-dependent dfflux pump, transporting a number of unrelated organic compounds out of the cell (Juranka et al, *FASEB J.* 1989, 3, 2583–2592). The level of expression of gp-170 has been shown to correlate with the degree of drug resistance (Raderer and Sscheitharer, *Cancer* 1993, 72, 3553–3563). Gp-170 appears to act as a pump that actively extrudes a wide variety of structurally unrelated compounds, including a full range of antineoplastic drugs. Another ATP-dependent membrane efflux pump, the product of the MRP gene, has also been implicated in the MDR phenomenon (Krishnamachary and Center, *Cancer Res.* 1993, 53, 3658–3661), as have other ATP-dependent and enzymatic mechanisms.

Drugs of proven antitumor chemotherapeutic value to which MDR has been observed include vinblastine, vincristine, etoposide, teniposide, doxorubicin (adriamycin), daunorubicin, pliamycin (mithramycin), and actinomycin D (Jones et al, *Cancer (Suppl)*1993, 72, 3484–3488). Many tumors are intrinsically multidrug resistant (e.g., adenocarcinomas of the colon and kidney) while other tumors acquire MDR during the course of therapy (e.g., neuroblastomas and childhood leukemias).

A variety of structurally diverse agents have been identified which can restore partly or sometimes completely the normal drug sensitivity to some MDR tumor cells. It is assumed that these chemosensitizers are effective as a result of their ability to interfere with gp-170, causing a reversal in the increase in drug efflux. Among these agents are calcium channel blockers (e.g., verapamil), calmodulin inhibitors (e.g., trifluoperazine), antibiotica (e.g., erythromycin), cardiovascularagents (e.g., quinidine), noncytotoxic analogs of anthracyclines and vinca alkaloids, cyclosporin A and analogs thereof, FK-506 and analogs thereof, and derivatives of cyclopeptides (Lum et al, *Cancer (Suppl)*1993, 72, 3502–3514). However, at the present time, none of these agents has provided a significant contribution to the chemotherapeutic index for the treatment of cancer due to their significant pharmacologidal effects on other organ systems. An effective therapeutic agent for the reversal of MDR needs to have efficacy against the menbrane pump as well as lack of significant toxicity and other nonspecific pharmacological effects.

The present invention describes a family of novel substituted imidazole derivatives of Formula (1) that are effective in increasing the sensitivity of tumor cells resistant to anticancer chemotherapeutic agents, such as doxorubicin (DOX), taxol, vinblastine (VLB), and enhancing the sensitivity of multi-drug resistant cells. These compounds have the effect of reducing the resistance of MDR tumor cells, and potentiating the sensitivity of cells to antitumor drugs, such as DOX, taxol, VLB. These compounds are expected to have broad application in the chemotherapy of cancer.

SUMMARY OF THE INVENTION

The novel compounds of this invention have the general structure (1)

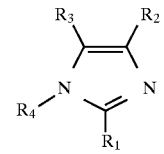

Formula 1 and are capable of restoring sensitivity to multi-drug resistant tumor cells. It is an object of this invention to provide compounds that have sufficient activity to sensitize multi-drug resistant tumor cells to antineoplastic agents.

It is an additional object of this invention to provide a method of sensitizing multi-drug resistant tumor cells using the novel compounds of the present invention.

A further object is to provide a method of treatment of MDR or drug-sensitive tumor cells by administering a sufficient amount of a compound of the present invention, prior to, together with, or subsequent to the administration of an antitumor chemotherapeutic agent. A further object is to provide pharmaceutical compositions for increasing the sensitivity of tumor cells to antitumor chemotherapeutic agents and thus for the treatment of tumors that are susceptible to anti-cancer chemotherapeutic agents but have become resistant to such chemotherapy.

Definitions

As used herein, the term "attached" signifies a stable covalent bond, certain preferred points of attachment being apparent to those skilled in the art.

The terms "halogen" or "halo" include fluorine, chlorine, bromine, and iodine.

The term "alkyl" includes $C_1$–$C_{11}$ straight chain saturated, $C_1$–$C_{11}$, branched saturated, $C_3$–$C_8$ cyclic saturated and $C_1$–$C_{11}$ straight chain or branched saturated aliphatic hydrocarbon groups substituted with $C_3$–$C_8$ cyclic saturated aliphatic hydrocarbon groups having the specified number of carbon atoms. For example, this definition shall include but is not limited to methyl (Me), ethyl (Et), propyl (Pr), butyl (Bu), pentyl, hexyl, heptyl, octyl, nonyl, decyl, undecyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, methylcyclopropyl, and the like.

The term "alkenyl" includes $C_2$–$C_{11}$ straight chain unsaturated, $C_2$–$C_{11}$ branched unsaturated, $C_5$–$C_8$ unsaturated cyclic, and $C_2$–$C_{11}$ straight chain or branched unsaturated aliphatic hydrocarbon groups substituted with $C_3$–C8 cyclic saturated and unsaturated aliphatic hydrocarbon groups having the specified number of carbon atoms. Double bonds may occur in any stable point along the chain and the carbon-carbon double bonds may have either the cis or trans configuration. For example, this definition shall include but is not limited to ethenyl, propenyl, butenyl, pentenyl, hexenyl, heptenyl, octenyl, nonenyl, decenyl, undecenyl, 1,5-octadienyl, 1,4,7-nonatrienyl, cyclopentenyl, cyclohexenyl, cycloheptenyl, cyclooctenyl, ethylcyclohexenyl, butenylcyclopentyl, 1-pentenyl-3-cyclohexenyl, and the like.

The term "alkyloxy" (e.g. methoxy, ethoxy, propyloxy, allyloxy, cyclohexyloxy) represents an alkyl group as defined above having the indicated number of carbon atoms attached through an oxygen bridge.

The term "alkylthio" (e.g. methylthio, ethylthio, propylthio, cyclohexylthio and the like) represents an alkyl group as defined above having the indicated number of carbon atoms attached through a sulfur bridge.

The term "alkylamino" (e.g. methylamino, diethylamino, butylamino, N-propyl-N-hexylamino, (2-cyclopentyl) propylamino, hexylamino, pyrrolidinyl, piperidinyl and the like) represents one or two alkyl groups as defined above having the indicated number of carbon atoms attached through an amine bridge. The two alkyl groups maybe taken together with the nitrogen to which they are attached forming a cyclic system containing 3 to 11 carbon atoms with at least one $C_1$–$C_{11}$ alkyl, aryl $C_0$–$C_{11}$ alkyl substituent.

The term "alkylaminoalkyl" represents an alkylamino group attached through an alkyl group as defined above having the indicated number of carbon atoms.

The term "alkyloxy(alkyl)amino" (e.g. methoxy(methyl) amine, ethoxy(propyl)amine) represents an alkyloxy group as defined above attached through an amino group, the amino group itself having an alkyl substituent.

The term "alkylcarbonyl" (e.g. cyclooctylcarbonyl, pentylcarbonyl, 3-hexylcarbonyl) represents an alkyl group as defined above having the indicated number of carbon atoms attached through a carbonyl group.

The term "alkylcarboxy" (e.g. heptylcarboxy, cyclopropylcarboxy, 3-pentenylcarboxy) represents an alkylcarbonyl group as defined above wherein the carbonyl is in turn attached through an oxygen. The term "alkylcarboxyalkyl" represents an alkylcarboxy group attached through an alkyl group as defined above having the indicated number of carbon atoms.

The term "alkylcarbonylamino" (e.g. hexylcarbonylamino, cyclopentylcarbonyl-aminomethyl, methylcarbonylaminophenyl) represents an alkylcarbonyl group as defined above wherein the carbonyl is in turn attached through the nitrogen atom of an amino group. The nitrogen group may itself be substituted with an alkyl or aryl group.

The term "aryl" represents an unsubstituted, mono-, di- or trisubstituted monocyclic, polycyclic, biaryl and heterocyclic aromatic groups covalently attached at any ring position capable of forming a stable covalent bond, certain preferred points of attachment being apparent to those skilled in the art (e.g., 3indolyl, 4-imidazolyl). The aryl substituents are independently selected from the group consisting of halo, nitro, cyano, trihalomethyl, $C_{1-11}$ alkyl, aryl $C_{1-11}$ alkyl, $C_{0-11}$ alkyloxy $C_{0-11}$ alkyl, aryl $C_{0-11}$ alkyloxy $C_{0-11}$ alkyl, $C_{0-11}$ alkylthio $C_{0-11}$ alkyl, aryl $C_{0-11}$ alkylthio $C_{0-11}$ alkyl, $C_{0-11}$ alkylamino $C_{0-11}$ alkyl, aryl $C_{0-11}$ alkylamino $C_{0-11}$ alkyl, di(aryl $C_{1-11}$ alkyl)amino $C_{0-11}$ alkyl, $C_{1-11}$ alkylcarbonyl $C_{0-11}$ alkyl, aryl $C_{1-11}$ alkylcarbonyl $C_{0-11}$ alkyl, $C_{1-11}$ alkylcarboxy $C_{0-11}$ alkyl, aryl $C_{1-11}$ alkylcarboxy $C_{0-11}$ alkyl, $C_{1-11}$ alkylcarbonylamino $C_{0-11}$ alkyl, aryl $C_{1-11}$ alkylcarbonylamino $C_{0-11}$ alkyl, —$C_{0-11}$ alkylCOOR$_1$, —$C_{0-11}$ alkylCONR$_2$R$_3$ wherein R$_1$, R$_2$ and R$_3$ are independently selected from hydrogen, $C_1$–$C_{11}$ alkyl, aryl $C_0$–$C_{11}$ alkyl, or R$_2$ and R$_3$ are taken together with the nitrogen to which they are attached forming a cyclic system containing 3 to 8 carbon atoms with at least one $C_1$–$C_{11}$ alkyl, aryl $C_0$–$C_{11}$ alkyl substituent.

The definition of aryl includes but is not limited to phenyl, biphenyl, naphthyl, dihydronaphthyl, tetrahydronaphthyl, indenyl, indanyl, azulenyl, anthryl, phenanthryl, fluorenyl, pyrenyl, thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, indolyl, isoindolyl, indolizinyl, indazolyl, imidazolyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl.

The term "arylalkyl" (e.g. (4-hydroxyphenyl)ethyl, (2-aminonaphthyl)hexyl, pyridylcyclopentyl) represents an aryl group as defined above attached through an alkyl group as defined above having the indicated number of carbon atoms.

The term "carbonyloxy" represents a carbonyl group attached through an oxygen bridge.

In the above definitions, the terms "alkyl" and "alkenyl" maybe used interchangeably in so far as a stable chemical entity is formed, as obvious to those skilled in the art.

The term "therapeutically effective amount" shall mean that amount of drug or pharmaceutical agent that will elicit the biological or medical response of a tissue, system, animal, or human that is being sought by a researcher, veterinarian, medical doctor or other clinician.

DETAILED DESCRIPTION OF THE INVENTION

The novel compounds of this invention have the general structure as depicted in Formula (1)

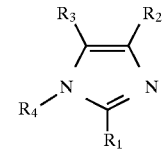

Formula 1 wherein the substituents R$_1$, R$_2$, R$_3$, and R$_4$ are defined as described in A and B below:

A. when R$_1$ is selected from the group consisting of:
 (i) substituted $C_{1-11}$ alkyl or substituted $C_{2-11}$ alkenyl, wherein the substituents are selected from the group consisting of hydroxy, $C_{1-6}$ alkyloxy; or
 (ii) mono-, di-,and tri-substituted aryl-$C_{0-11}$ alkyl wherein aryl is selected from the group consisting of phenyl, furyl, thienyl wherein the substituents are selected from the group consisting of:

(a) phenyl, trans-2-phenylethenyl, 2-phenylethynyl, 2-phenylethyl, or in which the said phenyl group is mono- or disubstituted with a member selected from the group consisting of hydroxy, halo, $C_{1-4}$ alkyl and $C_{1-4}$ alkyloxy, (b) substituted $C_{1-6}$ alkyl, substituted $C_{2-6}$ alkyloxy, substituted $C_{2-6}$ alkylthio, substituted $C_{2-6}$ alkoxycarbonyl, wherein the substituents are selected from the group consisting of $C_{1-6}$ alkoxy, $C_{1-6}$ alkylthio, or (c) $C_{1-11}$ $CO_2R_5$, $C_{1-11}$ $CONHR_5$, trans-$CH=CHCO_2R_5$, or trans-$CH=CHCONHR_5$ wherein $R_5$ is $C_{1-11}$ alkyl, or phenyl $C_{1-11}$ alkyl, $C_{1-6}$ alkoxycarbonylmethyleneoxy;

then $R_2$ and $R_3$ are each independently selected from the group consisting of mono-, di, and tri-substituted phenyl wherein the substituents are independently selected from:

(i) substituted $C_{1-6}$ alkyl, (ii) substituted $C_{1-6}$ alkyloxy, $C_{3-6}$ alkenyloxy, substituted $C_{3-6}$ alkenyloxy, (iii) substituted $C_{1-6}$ alkyl-amino, di(substituted $C_{1-6}$ alkyl)amino, (iv) $C_{3-6}$ alkenyl-amino, di($C_{3-6}$ alkenyl)amino, substituted $C_{3-6}$ alkenyl-amino, di(substituted $C_{3-6}$ alkenyl) amino, (v) pyrrolidino, piperidino, morpholino, imidazolyl, substituted imidazolyl, piperazino, N—$C_{1-6}$ alkylpiperazino, N—$C_{3-6}$ alkenylpiperazino, N—($C_{1-6}$ alkoxy $C_{1-6}$ alkyl)piperazino, N—($C_{1-6}$ alkoxy $C_{3-6}$ alkenyl)piperazino, N—($C_{1-6}$ alkylamino $C_{1-6}$ alkyl) piperazino, N—($C_{1-6}$ alkylamino $C_{3-6}$ alkenyl) piperazino, wherein the substituents are selected from the group consisting of (a) hydroxy, $C_{1-6}$ alkylalkoxy, $C_{1-6}$ alkylamino, (b) $C_{3-6}$ alkenyloxy, $C_{3-6}$ alkenylamino, or (c) pyrrolidino, piperidino, morpholino, imidazolyl, substituted imidazolyl, piperazino, N—$C_{1-6}$ alkenylpiperazino, N—$C_{3-6}$ alkenylpiperazino, N—($C_{1-6}$ alkoxy $C_{1-6}$ alkyl)piperazino, N—($C_{1-6}$ alkoxy $C_{3-6}$ alkenyl)piperazino, N—($C_{1-6}$ alkylamino $C_{1-6}$ alkyl)piperazino, N—($C_{1-6}$ alkylamino $C_{3-6}$ alkenyl)piperazino, or $R_2$ and $R_3$ taken together forming an aryl group such as phenyl, pyridyl, in which the aryl may be optionally substituted, wherein the substituents are defined as above in (i)–(v);

and $R_4$ is selected from the group consisting of:

(i) hydrogen;

(ii) substituted $C_{1-11}$ alkyl or $C_{2-11}$ alkenyl wherein the substituents are independently selected from the group consisting of hydrogen, hydroxy, $C_{1-6}$ alkyloxy, $C_{1-6}$ alkylthio, $C_{1-6}$ alkylamino, phenyl-$C_{1-6}$ alkylamino, $C_{1-6}$ alkoxycarbonyl; or (iii) substituted aryl $C_{0-11}$ alkyl wherein the aryl group is selected from phenyl, imidazolyl, furyl, thienyl in which the substituents are selected from A. (a–c); or B. when $R_1$ is selected from the group consisting of:

Mono-,di-, and tri-substituted aryl-$C_{0-6}$ alkyl wherein aryl is selected from the group consisting of phenyl, thienyl, and the substituents are selected from the group consisting of:

(a) trans-2-substituted benzimidazolylethenyl, trans-2-substituted benzoxazolylethenyl, trans-2-substituted benzthiazolylethenyl, in which the substituents are selected from the group consisting of hydrogen, hydroxy, halo, trihalomethyl, $C_{1-4}$ alkl and $C_{1-4}$ alkyloxy, $C_{1-4}$ alkloxycarbonyl, $C_{1-4}$ alkylamino, di($C_{1-4}$ alkyl)amino, $C_{3-6}$ alkenylamino, di($C_{3-6}$ alkenyl)amino, $C_{0-4}$ alkyloxy-$C_{1-4}$ alkylamino, substituted $C_{1-4}$ alkyl and $C_{1-4}$ alkyloxy, substituted $C_{1-4}$ alkyloxycarbonyl, substituted $C_{1-4}$ alkylamino, di(substituted $C_{1-4}$ alkyl)amino, substituted $C_{3-6}$ alkenylamino, di(substituted $C_{3-6}$ alkenyl)amino, wherein the substituents are as defined above, (b) trans-2-cyano ethenyl, trans-2-alkylsulfonyl ethenyl, trans-2alkenylsulfonyl ethenyl, trans-2- substituted alkylsulfonyl ethenyl, trans-2- substituted alkenylsulfonyl ethenyl, in which the substituents are defined above, (c) $C_{1-6}$ $CO_2R_5$, trans- $CH=CHCO_2R$, $C_{1-6}CONHR_5$, or trans-$CH=CHCONHR_5$, wherein $R_5$ is $C_{1-6}$ alkoxy $C_{2-6}$ alkyl, amino $C_{2-6}$ alkyl, $C_{1-6}$ alkylamino $C_{2-6}$ alkyl, di($C_{0-6}$ alkyl)amino $C_{2-6}$ alkyl, $C_{1-6}$ alkylthio $C_{2-6}$ alkyl, substituted $C_{1-6}$ alkoxy $C_{2-6}$ alkyl, substituted $C_{1-6}$ alkylamino $C_{2-6}$ alkyl, di(substituted $C_{1-6}$ alkyl)amino $C_{2-6}$ alkyl, substituted $C_{1-6}$ alkylthio $C_{2-6}$ alkyl, in which the substituents are selected from the group consisting of pyrrolidino, piperidino, morpholino, piperazino, N—$C_{1-6}$ alkenylpiperazino, N—$C_{3-6}$ alkenylpiperazino, N—($C_{1-6}$ alkoxy $C_{0-6}$ alkyl)piperazino, N—($C_{1-6}$ alkoxy $C_{3-6}$ alkenyl) piperazino, N—($C_{1-6}$ alkylamino $C_{1-6}$ alkyl) piperazino, N—($C_{1-6}$ alkylamino $C_{3-6}$ alkenyl) piperazino, imidazolyl, oxazolyl, thiazolyl, (d) $C_{1-6}CONR_6R_7$, or trans- $CH=CHCONR_6R_7$, wherein $R_6$ and $R_7$ are independently selected from the group consisting of $C_{1-6}$ alkyl, phenyl $C_{1-6}$ alkyl, $C_{1-6}$ alkoxycarbonylmethyleneoxy, hydroxy $C_{2-6}$ alkyl, $C_{1-6}$ alkyloxy $C_{2-6}$ alkyl, amino $C_{2-6}$ alkyl, $C_{1-6}$ alkylamino $C_{2-6}$ alkyl, di($C_{1-6}$ alkyl)amino $C_{2-6}$ alkyl, $C_{1-6}$ alkylthio $C_{2-6}$ alkyl, substituted $C_{1-6}$ alkoxy $C_{2-6}$ alkyl, substituted $C_{1-6}$ alkylamino $C_{2-6}$ alkyl, di(substituted $C_{1-6}$ alkyl)amino $C_{2-6}$ alkyl, substituted $C_{1-6}$ alkylthio $C_{2-6}$ alkyl, wherein the substituents are selected from the group consisting of pyrrolidino, piperidino, morpholino, piperazino, N—$C_{1-6}$ alkenylpiperazino, N—$C_{3-6}$ alkenylpiperazino, N—($C_{1-6}$ alkoxy $C_{1-6}$ alkyl)piperazino, N—($C_{1-6}$ alkoxy $C_{3-6}$ alkenyl) piperazino, N—($C_{1-6}$ alkylamino $C_{1-6}$ alkyl) piperazino, N—($C_{1-6}$ alkylamino $C_{3-6}$ alkenyl) piperazino, imidazolyl, oxazolyl, thiazolyl, (e) $R_7$ C(O) $C_{1-6}$ alkyl, $R_7$ C(O) carbonyl $C_{2-6}$ alkenyl, in which $R_7$ is defined as above [2(d)], (f) HO—$C_{1-6}$ alkyl-$C_{2-6}$ alkenyl, $R_7—O—C_{1-6}$ alkyl-$C_{2-6}$ alkenyl, $R_7NH—C_{1-6}$ alkyl-$C_{2-6}$ alkenyl, $R_6R_7N—C_{1-6}$ alkyl-$C_{2-6}$ alkenyl, $R_7NH—C(O)—O—C_{1-6}$ alkyl-$C_{2-6}$ alkenyl, $R_{1-6}R_7N—C(O)—O—C_{1-6}$ alkyl-$C_{2-6}$ alkenyl, $R_7O—C(O)—O—C_{1-6}$ alkyl-$C_{2-6}$ alkenyl, $R_7—C(O)—O—C_{1-6}$ alkyl-$C_{2-6}$ alkenyl, wherein $R_6$ and $R_7$ is defined as above [2(d)], (g) $R_7—O—CO_{0-3}$ alkyl-$C_{3-6}$ cycloalkan-1-yl, $R_7NH—C_{0-3}$ alkyl- $C_{3-6}$ cycloalkan1-yl, $R_6R_7N—C_{0-3}$ alkyl-$C_{3-6}$ cycloalkan-1-yl, $R_7NH—C(O)—O—C_{0-3}$ $C_{3-6}$ cycloalkan-1-yl, $R_6R_7N—C(O)—O—C_{0-3}$ alky- $C_{3-6}$ cycloalkan-1-yl, $R_7O—C(O)—O—C_{0-3}$ alkyl- $C_{3-6}$ cycloalkan-1-yl, $R_7—C(O)—O—C_{0-3}$ alkyl- $C_{3-6}$ cycloalkan-1-yl, $R_7O—C(O)—CO_{0-3}$ alkyl- $C_{3-6}$ cycloalkan-1-yl, wherein $R_7$ and is defined as above [2(d)];

then $R_2$ and $R_3$ are each independently selected from the group consisting of (1) hydrogen, halo, trihalomethyl, $C_{1-6}$ alkyl, substituted $C_{1-6}$ alkyl, $C_{1-6}$ alkenyl, substituted $C_{1-6}$ alkenyl, $C_{1-6}$ alyloxy, substituted $C_{1-6}$ alkyloxy, $C_{3-6}$ alkenyloxy, substituted $C_{3-6}$ alkenyloxy, $C_{1-6}$ alkylamino, substituted $C_{1-6}$ alkylamino, $C_{3-6}$ alkenylamino, substituted $C_{3-6}$ alkenylamino, (2) mono-, di-, and tri-substituted phenyl wherein the substituents are independently selected from:
 (i) halo, trifluoromethyl, substituted $C_{1-6}$ alkyl,
 (ii) $C_{1-6}$ alkyloxy, substituted $C_{1-6}$ alkyloxy, $C_{3-6}$ alkenyloxy, substituted $C_{3-6}$ alkenyloxy,
 (iii) $C_{1-6}$ alkyl-amino, di($C_{1-6}$ alkyl)amino, substituted $C_{1-6}$ alkyl-amino, di(substituted $C_{1-6}$ alkyl)amino, $C_{3-6}$ alkenyl-amino, di($C_{3-6}$ alkenyl)amino, substituted $C_{3-6}$ alkenyl-amino, di(substituted $C_{3-6}$ alkenyl)amino,or
 (iv) pyrrolidino, piperidino, morpholino, imidazolyl, substituted imidazolyl, piperazino, N—$C_{1-6}$ alkenylpiperazino, N—$C_{3-6}$ alkenylpiperazino, N—($C_{1-6}$ alkoxy $C_{1-6}$ alkyl)piperazino, N—($C_{1-6}$ alkoxy $C_{3-6}$ alkenyl)piperazino, N—($C_{1-6}$ alkylamino $C_{1-6}$ alkyl)piperazino, N—($C_{1-6}$ alkylamino $C_{3-6}$ alkenyl)piperazino, wherein the substituents are selected from the group consisting of
 (a) hydrogen, hydroxy, halo, trifluoromethyl,
 (b) $C_{1-6}$ alkylalkoxy, $C_{0-6}$ alkylamino, $C_{1-6}$ alkylthio,
 (c) $C_{3-6}$ alkenyloxy, $C_{3-6}$ alkenylamino, $C_{3-6}$ alkenylthio, or
 (d) pyrrolidino, piperidino, morpholino, imidazolyl, substituted imidazolyl, piperazino, N—$C_{1-6}$ alkenylpiperazino, N—$C_{3-6}$ alkenylpiperazino, N—($C_{1-6}$ alkoxy $C_{1-6}$ alkyl)piperazino, N—($C_{1-6}$ alkoxy $C_{3-6}$ alkenyl)piperazino, N—($C_{1-6}$ alkylamino $C_{1-6}$ alkyl)piperazino, N—($C_{1-6}$ alkylamino $C_{3-6}$ alkenyl)piperazino;

with the proviso that at least one of $R_2$ and $R_3$ group be selected from [B (2)] and the phenyl and the substituents be selected from (ii)–(v) above; or $R_2$ and $R_3$ taken together forming an aryl group such as phenyl, pyridyl, in which the aryl may be optionally substituted, wherein the substituents are defined as above in (i)–(iv);

and $R_4$ is selected from the group consisting of:
 (a) hydrogen;
 (b) substituted $C_{1-11}$ alkyl or $C_{2-11}$ alkenyl wherein the substituents are independently selected from the group consisting of hydrogen, hydroxy, $C_{1-6}$ allyloxy, $C_{1-6}$ alkylthio, $C_{1-6}$ alkylamino, phenyl-$C_{1-6}$ alkylamino, $C_{1-6}$ alkoxycarbonyl and the substituents are selected from (ii)–(iv); or
 (c) aryl $C_{0-11}$ alkyl wherein the aryl group is selected from phenyl, imidazolyl, furyl, thienyl.

Novel compounds of the present invention include but are not limited to the following compounds:

2-[trans-2-(2-benzoxazolyl)ethenylphenyl]-4,5-bis (4-N, N-dimethylaminophenyl) imidazole, 2-[trans-2-(2-benzoxazolyl)ethenylphenyl]-4-(4-N,N-dimethylaminophenyl)-5-(4N-methylaminophenyl) imidazole, 2-[trans-2-(2-benzoxazolyl)ethenylphenyl]-4-(4-N,N-diethylaminophenyl)-5-(4-N-methylaminophenyl) imidazole, 2-[trans-2-(2-benzoxazolyl)ethenylphenyl]-4-(4-N-disopropylaminophenyl)-5-(4-N-methylaminophenyl) imidazole, 2-[trans-2-(2-benzoxazolyl)ethenylphenyl]-4-(4-N-methylaminophenyl)-5-(4pyrrolidinophenyl) imidazole, 2-[trans-2-(2-benzoxazolyl)ethenylphenyl] -4-(4-N,N-dimethylaminophenyl)-5-[4(2-methoxyethylamino)phenyl] imidazole, 2-[trans-2-(2-benzthiazolyl)ethenylphenyl]-4, 5-bis (4-N, N-dimethylaminophenyl) imidazole, 2-[trans-2-(2-benzthiazolyl)ethenylphenyl]-4-(4-N,N-dimethylaminophenyl)-5-(4N-methylaminophenyl) imidazole, 2-[trans-2-(2-cyano)ethenylphenyl]-4, 5-(4-N,N-dimethylaminophenyl) imidazole, 2-[trans-2-(2-cyano)ethenylphenyl]-4-(4-N,N-dimethylaminophenyl)-5-[4-N-(2methoxyethyl)amino) phenyl] imidazole, 2-(trans-2-methoxycarbonyl-ethenylphenyl)-4-(4-N,N-diallylaminophenyl)-5-(4fluoro-phenyl) imidazole, 2-(trans-2-methoxycarbonyl-ethenylphenyl)-4-(4-N-methylaminophenyl)-5-(4-pyrrolidinophenyl) imidazole, 2-(trans-2-methoxycarbonyl-ethenylphenyl)-4-(4-N-methylaminophenyl)-5-(4-piperidinophenyl) imidazole, 2-(trans-2-methoxycarbonyl-ethenylphenyl)-4-[4-N,N-di(2-methoxyethyl)aminophenyl]-5-(4-N-methylaminophenyl) imidazole, 2-(trans-2-methoxycarbonyl-ethenylphenyl)-4-[4-(1-imidazolyl)phenyl]-5-(4-N-methylaminophenyl) imidazole, 2-(trans-2-methoxycarbonyl-ethenylphenyl)-4,5-bis (4-N-morpholinophenyl) imidazole, 2-(trans-2-methoxycarbonyl-ethenylphenyl)-4-(4-N,N-dimethylaminophenyl)-5-(4N-morpholinophenyl) imidazole, 2-(trans-2-methoxycarbonyl-ethenylphenyl)-4-(4-N-methylaminophenyl)-5-(4-N-morpholinophenyl) imidazole:

2-[4-(3-methoxy-trans-1-propen-1-yl)phenyl]-4,5-bis (4-N-dimethylaminophenyl) imidazole, 2-[4-(3-ethoxy-trans-1-propen-1-yl)phenyl]-4,5-bis (4-N, N-dimethylaminophenyl) imidazole, 2-[4-(3-ethoxy-trans-1-propen-1-yl)phenyl]-4-(4-N,N-dimethylaminophenyl)-5-(4-N-methylaminophenyl) imidazole, 2-[4-(3-benzyloxy-trans-1-propen-1-yl)phenyl]-4,5-bis (4-N, N-dimethylaminophenyl) imidazole, 2-[4-(3-phenoxy-trans-1-propen-1-yl)phenyl]-4-(4-N, N-dimethylaminophenyl)-5-(4-N-methylaminopheny) imidazole, 2-{4-[3-(3,4-dimethoxy-phenoxy)-trans-1-propen-1-yl] phenyl}-4-(4-N-dimethylaminophenyl)-5-(4-N-methylaminopheny) imidazole, 2-[4-(3-N,N-diethylamino-trans-1-propen-1-yl)phenyl]-4,5-bis (4-N,N-dimethylaminophenyl) imidazole, 2-[4-(3-N-morpholino-trans-1-propen-1-yl)phenyl]-4, 5-bis (4-N,N-dimethylaminophenyl) imidazole, 2-[4-(3-N-piperidino-trans-1-propen-1-yl)phenyl]-4,5-bis (4-N,N-dimethylaminophenyl) imidazole, 2-[4-(3-N,N-dimethylamino-trans-1-propen-1-yl)phenyl]-4,5-bis (4-N,N-dimethylaminophenyl) imidazole, 2-{4-[3-(2-methoxy-ethoxy)-trans-1-propen-1-yl] phenyl}-4, 5-bis (4-N,N-dimethylaminophenyl) imidazole, 2-[4-(3-butoxy-trans-1-propen-1-yl)phenyl]-4,5-bis (4-N, N-dimethylaminophenyl) imidazole, 2-[4-(3-ethoxy-trans-1-propen-1-yl)phenyl]-4,5-bis (4-N, N-diethylaminophenyl) imidazole, 2-[4-(3-ethoxy-trans-1-propen-1-yl)phenyl]-4-(4-N,N-diethylaminophenyl)-5-(4-N-methylaminophenyl) imidazole, 2-[4-(3-methoxy-trans-1-propen-1-yl)phenyl]-4,5-bis (4-pyrrolidinophenyl) imidazole, 2-[4-(3-ethoxy-trans-1-propen-1-yl)phenyl]-4,5-bis (4-pyrrolidinophenyl) imidazole, 2-[4-(3-ethoxy-trans-1-propen-1-yl)phenyl]-4-(4-N,N-dimethylaminophenyl)-5-(4-pyrrolidinophenyl) imidazole, 2-[4-(3-ethoxy-trans-1-propen-1-yl)phenyl]-4-(4-N-methylaminophenyl)-5-(4-pyrrolidinophenyl) imidazole, 2-[4-(3-ethoxy-trans-1-propen-1-yl)phenyl]-4,5-bis (4-N-morpholinophenyl) imidazole, 2-[4-(3-ethoxy-trans-1-propen-1-yl)phenyl]-4-(4-N,N-dimethylaminophenyl)-5-(4-N-morpholinophenyl) imidazole, 2-[4-(3-ethoxy-trans-1-propen-1-yl)phenyl]-4-(4-N-methylaminophenyl)-5-(4-N-morpholinophenyl) imidazole, 2-[4-(3-ethoxy-trans-1-propen-1-yl)phenyl]-4-(4-N-methylaminophenyl)-5-(4-N-isopropylaminophenyl) imidazole, 2-[4-trans-(2-methanesulfonyl-ethenyl)-phenyl]-4,5-bis (4-N, N-dimethylaminophenyl) imidazole, 2-(4-N-morpholinophenyl)-4,5-bis (4-N,N-dimethylaminophenyl) imidazole, 2-[4-(5-ethylcarboxyisoxazol-3-yl)-phenyl]-4,5-bis (4-N, N-dimethylaminophenyl) imidazole, 2-[4-trans-(2-methoxycarbonyl-ethenyl)phenyl]-4-(p-tolyl)-5-(4-N,N-diethylaminomethylphenyl) imidazole, 2-[4-trans-(2-methoxycarbonyl-ethenyl)phenyl]-4,5-bis (4-N,N-diethylaminomethylphenyl) imidazole, 2-[4-trans-(2-methoxycarbonyl)cyclopropan-1-yl]-4,5-bis (4-N,N-diethylaminomethylphenyl) imidazole, 2-[4-(3-ethoxy-trans-1-propen-1-yl)phenyl]-4,5-bis (4-dimethoxyphenyl) imidazole, 2-[4-(3-ethoxy-trans-1-propen-1-yl)phenyl]-4,5-bis (4-diethoxyphenyl) imidazole, 2-[4-(3-ethoxy-trans-1-propen-1-yl)phenyl]-4,5-bis (4-diisopropyloxyphenyl) imidazole, 1-(3-imidazole-1-yl-propyl)-2-[4-(3-ethoxy-trans-1-propen-1-yl)phenyl]-4,5-bis (4dimethoxyphenyl) imidazole, 1-(3-imidazole-1-yl-propyl)-2-[4-(3-ethoxy-trans-1-propen-1-yl)phenyl]-4,5-bis (4-diethoxyphenyl) imidazole, 1-(3-imidazole-1-yl-propyl)-2-[4-(3-ethoxy-trans-1-propen-1-yl)phenyl]-4,5-bis (4-diisopropyloxyphenyl) imidazole, 2-[4-(3-ethoxy-trans-1-propen-1-yl)phenyl]-4-(4-N, N-diethylphenyl) imidazole, 2-[4-(3-ethoxy-trans-1-propen-1-yl)phenyl]-4-(4-methoxyphenyl) imidazole, 2-[4-trans-(2-N,N-dimethylcarbonyl)-ethenyl]phenyl}-4,5-bis (4-N,N-dimethylaminophenyl) imidazole, 2-[4-(3-hydroxy-trans-1-propen-1-yl)phenyl]-4, 5-bis (4-N,N-dimethylaminophenyl) imidazole, 1-methyl-2-[4-(3-hydroxy-trans-1-propen-1-yl)phenyl]-4,5-bis (4-N,N-dimethylaminophenyl) imidazole, 2-[4-(3-pivalate-trans-1-propen-1-yl)phenyl]-4,5-bis (4-N,N-dimethylaminophenyl) imidazole, 2-[4-(3-methylcarbonyl-trans-1-propen-1-yl)phenyl]-4,5-bis (4-N,N-dimethylaminophenyl) imidazole, 2-[4-(3-methylcarbonyl-trans-1-propen-1-yl)phenyl]-5-methoxy benzimidazole, 2-[4-(3-ethoxy-trans-1-propen-1-yl)phenyl]-4,5-bis-(4-N-isopropylaminophenyl) imidazole, 2-[4-(3-ethoxy-trans-1-propen-1-yl)phenyl]-4-(4-N-ethylaminophenyl)-5-(4-N-isopropylaminophenyl) imidazole, 2-[4-(3-ethoxy-trans-1-propen-1-yl)phenyl]-4-(4-fluorophenyl)-5-(4-N-isopropylaminophenyl) imidazole, 2-[4-(3-ethoxy-trans-1-propen-1-yl)phenyl]-4-(4-N,N-dipropylphenyl) imidazole, 2-[4-(3-ethoxy-trans-1-propen-1-yl)phenyl]-4-(4-N-isopropylphenyl) imidazole, 2-[4-(3-ethoxy-trans-1-propen-1-yl)phenyl]-4-(4-N-isobutylphenyl) imidazole, 2-[4-(3-ethoxy-trans-1-propen-1-yl)phenyl]-4-(4-N-morpholinophenyl) imidazole, 2-[4-(3-ethoxy-trans-1-propen-1-yl)phenyl]-4-[4-N-(N'-ethyl)-piperizanophenyl) imidazole, 2-[4-(3-ethoxy-trans-1-propen-1-yl)phenyl]-4-(4-N-morpholinophenyl)-5-methyl-imidazole.

Preferred compositions of the invention include compositions comprising compounds as defined above in structural formula (1) (or pharmaceutically acceptable salts, prodrugs, esters, or solvates of these compounds) in admixture with a pharmaceutically acceptable diluent, adjuvent, or carrier.

Provided according to the invention, therefore, are novel compounds which modulate multi-drug resistance (MDR) in vitro in CEM/VLB1000 human cells.

Provided according to the invention, therefore, are novel compounds which modulate multi-drug resistance (MDR) in murine models with P388-ADR human cells.

Provided according to the invention, therefore, are novel compounds which modulate multi-drug resistance (MDR) in murine models with P388-ADR ascites human tumors.

Another aspect of the present invention provides compositions comprising MDR modulating compounds of the invention suitable for administration to a mammalian host.

As a preferred embodiment, the compounds of the invention may be used as therapeutics to modulate MDR in cancer patients who show resistance to anticancer chemotherapeutic agents such as DOX, taxol and VLB.

Preferred embodiments of the invention further include use of compounds of the invention in pharmaceutical preparations to increase the sensitization of MDR cancer cells in patients who show resistance to anticancer chemotherapeutic agents such as DOX, taxol and VLB.

Compounds of the invention may additionally be used for treatment or modulation of MDR in animals, including commercially important animals.

Provided according to this invention are methods of sensitizing multidrug resistant tumor cells using the novel compounds of the present invention.

Provided according to this invention are methods of treatment of MDR or drug-sensitive tumor cells by administering a sufficient amount of a compound of the present invention, prior to, together with, or subsequent to the administration of an antitumor chemotherapeutic agent.

Provided according to this invention are pharmaceutical compositions for increasing the sensitivity of tumor cells to antitumor chemotherapeutic agents and thus for the treatment of tumors that are susceptible to anti-cancer chemotherapeutic agents but have become resistant to such chemotherapy.

The invention further provides methods for making compounds of Formula (1) of the present invention having MDR modulating activity. The compounds of Formula (1) maybe prepared by procedures known to those skilled in the art from known compounds or readily preparable intermediates.

The following Examples are intended to illustrate the preparation of compounds of Formula 1, and as such are not intended to limit the invention as set forth in the claims appended thereto. Furthermore, the compounds described in the following examples are not to be construed as forming the only genus that is considered as the invention, and any combination of the compounds or their moieties may itself form a genus. The structure and purity of all final products were assured ny at least one of the following methods: thin-layer chromatography (TLC), mass spectroscopy, nuclear magnetic resonance (NMR) spectroscopy. NMR data is in the form of delta (d) values for major diagnostic protons, given in parts per million (ppm) relative to tetramethylsilane (TMS) as internal standard, determined at 400 MHz in deuterated sovents such as deuteriochloroform (CDCl₃), and deuteriomethanol (CD₃OD); conventional abbreviations used for signal shape are: s, singlet; d, doublet; t, triplet; dd, double of doublet; dt, double of triplet; m, multiplet; br., broad; etc. The following abbreviations have also been used: mL (milliliter), g (gram), mg (milligram), mol (moles), mmol (millimoles), equiv (equivalent).

The procedures employed to synthesize compounds depicted in Formula 1 are as follows:

Method A. General Procedure for the Preparation of Diones:

There are three methods by which these diones were synthesized, namely:

Method 1

4,4'-difluorodione 4 was reacted with a series of amines ($R_1R_2NH$) using an appropriate base such as $K_2CO_3$, $Na_2CO_3$, $Et_3N$, diisopropylethylamine (DIEA), etc., at elevated temperature (60°–150° C.) in an appropriate solvent such as alcohol, acetonitrile, N,N-dimethylformamide (DMF), dimethylsulfoxide (DMSO) to provide the mono-amino-diones 2 (procedure Bader et al *J. Org. Chem.* 1966, 31, 2319). The mono-amino-diones 2 were further reacted with another amine ($R_3R_4NH$) under the same conditions to afford the desired diones 3 as shown in Scheme 1. This procedure allows for the synthesis of unsymmetrical diones 6 (wherein $R_1R_2NH$ is different from $R_3R_4NH$). This chemistry was carried out using 1–1.5 equivalent of $R_1R_2NH$ and upon the completion of the reaction another equivalent of different amine ($R_3R_4NH$) was added to the reaction mixture to provide the desired unsymmetrical diones (Scheme 1).

Scheme 1

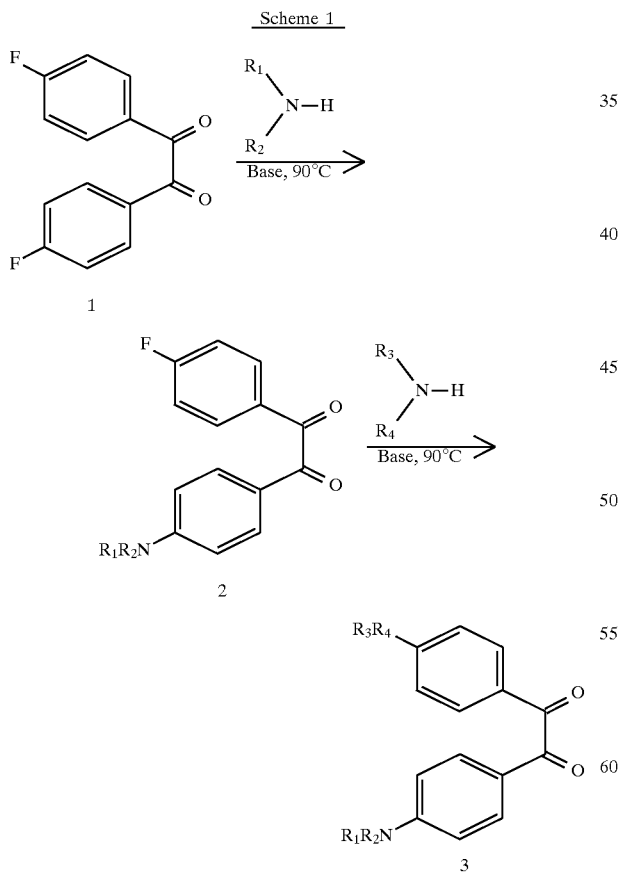

Unsymmetrcal diones were prepared according to the following procedure: To a solution of 4,4'-difluorobenzil in DMSO (0.5M) was added 1.2 equiv of amine $R_1R_2NH$ and 2 equiv of potassium carbonate. The resulting mixture was stirred in a 90° C. oil bath for 6–15 hours (TLC monitoring). After completion, the mixture was diluted with ether and extracted with 3M hydrochloric acid (×5) to remove the small amount of product resulted from the di-displacement. The organic layer was then washed with 6M hydrochloric acid until no more desired product in the ether layer (5 times). The aqueous layer was neutralized to pH 8 with 6M aqueous sodium hydroxide and it was extracted with dichloromethane. The organic layers were dried ($Na_2SO_4$), evaporated to give 4-amino,4'-fluorobenzil. This procedure was repeated with the second amine $R_3R_4NH$ (normally 2–3 equiv) and a simple workup by diluting the reaction mixture into ether and washed with water to remove DMSO. 4, 4'-diaminobenzil was thus obtained (50–90% overall depending amines used) in high purity.

For symmetrical diones (wherein $R_1R_2NH$ is equal to $R_2R_3NH$) the following procedure was followed:

To a solution of 4,4'-difluorobenzil in DMSO (0.5M) was added 2–3 equiv of amine $R_1R_2NH$ and 2–3 equiv of potassium carbonate. The resulting mixture was stirred in an 90° C. oil bath for 6–15 hours (TLC monitoring). After completion, the mixture was diluted into ether and washed with water to remove DMSO. The desired diones 6 were obtained (50–90% overall depending amines used) in high purity. The following examples have been synthesized according to method 1:

EXAMPLES 4) 4-N,N-dimethylamino-4'-methylaminobenzil

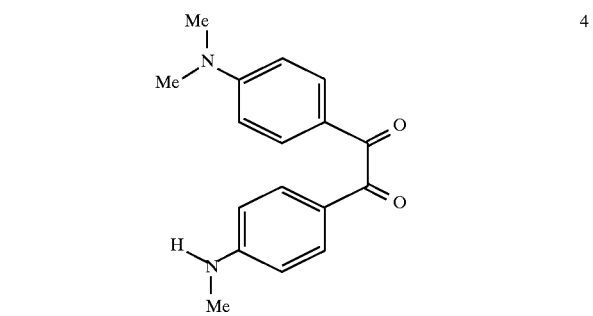

¹H NMR (400 MHz, CDCl₃) 67 2.80 (s, 3 H), 3.03 (s, 6 H), 4.48 (br s, 1 H),
6.48 (d, 2 H), 6.59 (d, 2 H), 7.75 (d, 2 H), 7.79 (d, 2 H).

5) 4-N,N-diethylamino-4'-methylaminobenzil

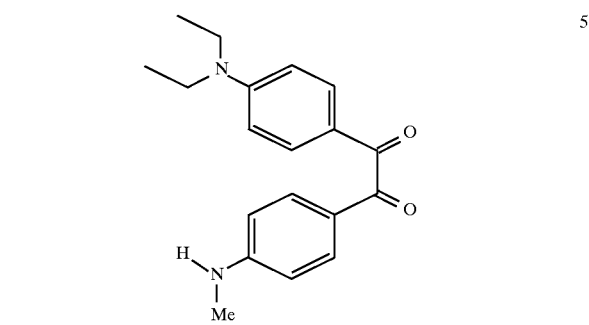

¹H NMR (400 MHz, CDCl₃) δ1.15 (t, 6 H), 2.85 (s, 3 H), 3.37 (q, 4 H), 4.40 (s, 1 H), 6.50 (d, 2 H), 6.57 (d, 2 H), 7.78 (d, 4 H).

6) 4-N-isopropylamino-4'-methylaminobenzil

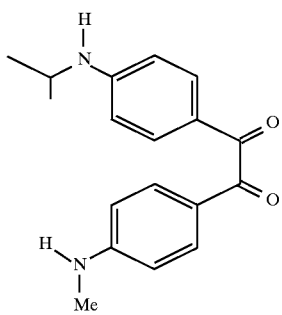

¹H NMR (400 MHz, CDCl₃) δ 1.18 (d, 6 H), 2.83 (d, 3 H), 3.65 (m, 1 H), 4.28 (br d, 1 H), 4.54 (br s, 1 H), 6.47 (d, 2 H), 6.49 (d, 2 H), 7.74 (d, 2 H), 7.76 (d, 2 H).

7) 4-pyrrolidino-4'-methylaminobenzil

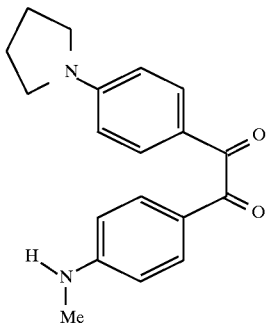

¹H NMR (400 MHz, CDCl₃) δ 1.98 (m, 4 H), 2.83 (s, 3 H), 3.32 (m, 4 H), 4.48 (s, 1 H), 6.46 (d, 2 H), 6.48 (d, 2 H), 7.76 (d, 2 H), 7.78 (d, 2 H).

8) 4-piperidino-4'-methylaminobenzil

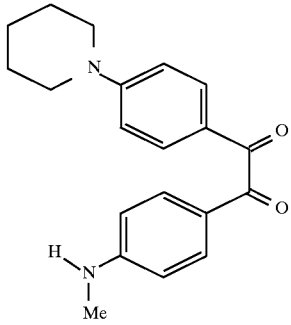

¹H NMR (400 MHz, CDCl₃) δ 1.61 (br s, 6 H), 2.83 (d, 3 H), 3.35 (br s, 4 H), 4.48 (s, 1 H), 6.49 (d, 2 H), 6.77 (d, 2 H), 7.76 (d, 2 H), 7.78 (d, 2 H).

9) 4-N,N-dimnethylamino-4'-N-(2-methoxyethyl)aminobenzil

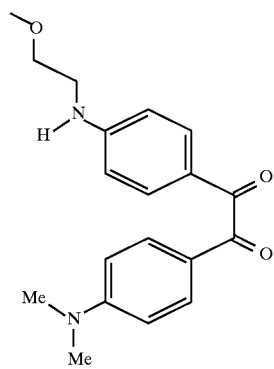

¹H NMR (400 MHz, CDCl₃) δ 3.03 (s, 6 H), 3.32 (m, 5 H), 3.56 (t, 2 H), 4.66 (s, 1 H), 6.53 (d, 2 H), 6.60 (d, 2 H), 7.77 (d, 2 H), 7.80 (d, 2 H).

10) 4-N,N-di-(2-methoxyethyl)amino-4'-methylaminobenzil

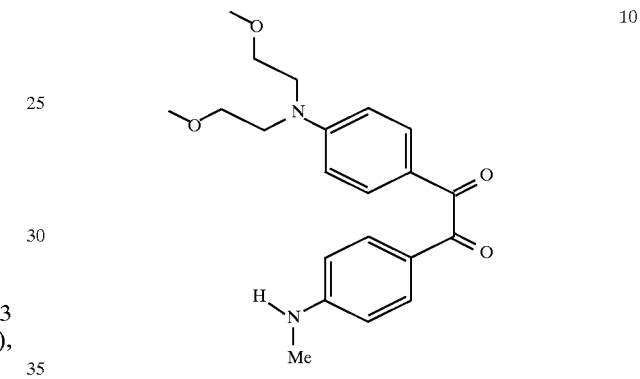

¹H NMR (400 MHz, CDCl₃) δ 2.82 (d, 3 H), 3.29 (s, 6 H), 3.50 (t, 4 H), 3.60 (t, 4 H), 4.48 (br s, 1 H), 6.49 (d, 2 H), 6.64 (d, 2 H), 7.76 (d, 4 H).

11) 4-(imidazole-1-yl)-4'-N-(2-methoxyethyl)aminobenzil

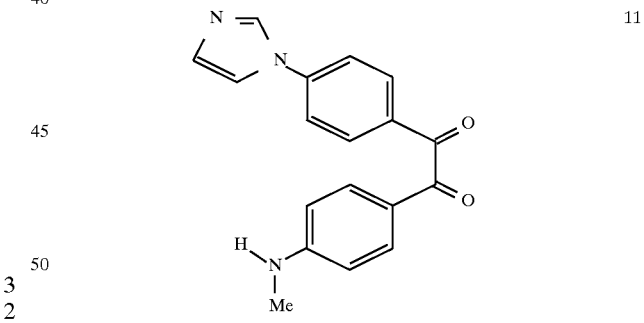

¹H NMR (400 MHz, CD₃OD) δ 2.82 (s, 3 H), 6.59 (d, 2 H), 7.15 (s, 1 H), 7.69 (m, 3 H), 7.76 (d, 2 H), 8.05 (d, 2 H), 8.29 (s, 1 H).

12) 4,4'-bis(4-morpholino)benzi

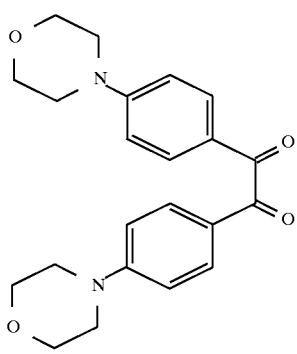

$^1$H NMR (400 MHz, CDCl$_3$) δ3.30 (m, 8 H), 3.80 (m, 8 H), 6.80 (d, 4 H), 7.82 (d, 4 H).

13) 4-N,N-dimethylamino-4'-(4-morpholino)benzil

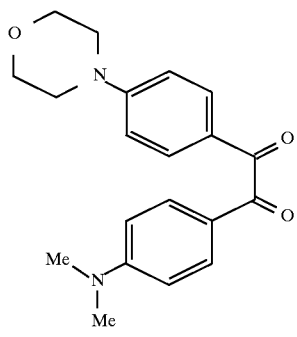

$^1$H NMR (400 MHz, CDCl$_3$) δ3.04 (s, 6 H), 3.30 (m, 4 H), 3.81 (m, 4 H), 6.61 (d, 2 H), 6.82 (d, 2 H), 7.81 (d, 2 H), 7.85 (d, 2 H).

14) 4-N-methylamino-4'-(4-morpholino)benzil

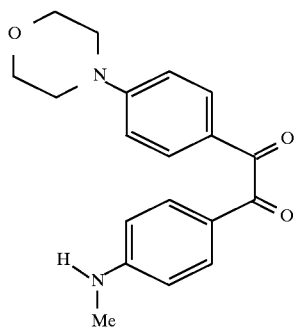

$^1$H NMR (400 MHz, CDCl$_3$) 67 2.90 (d, 3 H), 3.30 (m, 4 H), 3.80 (m, 4 H), 4.42 (m, 1 H), 6.52 (d, 2 H), 6.82 (d, 2 H), 7.78 (d, 2 H), 7.84 (d, 2 H).

15) 4-N,N-diallylamino-4'-fluorobenzil

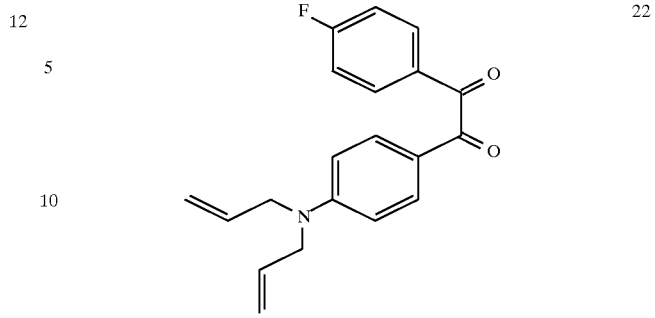

$^1$H NMR (400 MHz, CDCl$_3$) 67 3.95 (d, 4 H), 5.12 (m, 4 H), 5.78 (m, 2 H), 6.63 (d, 2 H), 7.09 (d, 1 H), 7.10 (d, 1 H), 7.75 (d, 2 H), 7.96 (m, 2 H).

Method 2

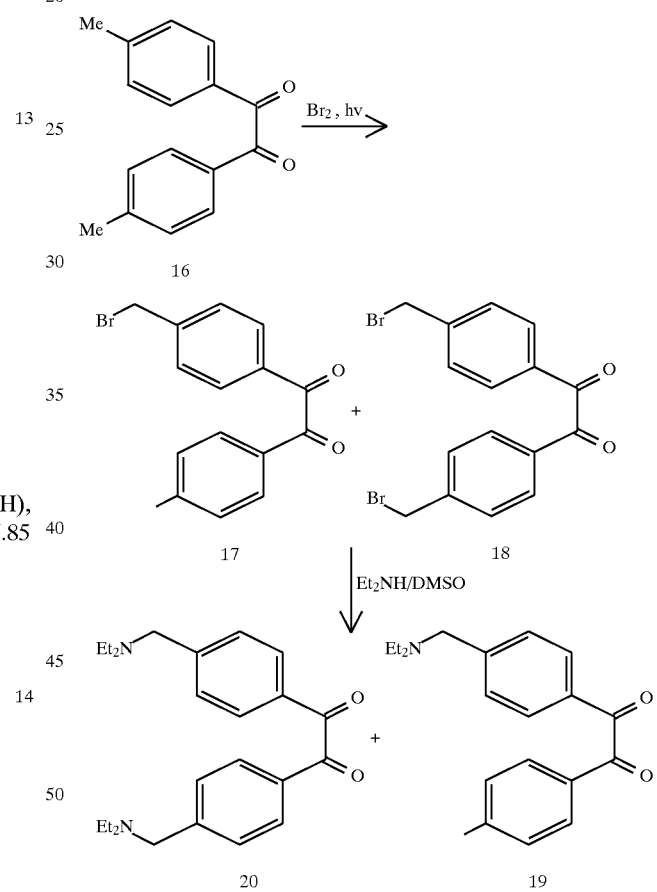

Compound 19 and 20 were prepared according to Venugopalan et al (*Indian J. Chem.* 1991, 30B, 777–783).

Compound 19 has: $^1$H NMR (400 MHz, CDCl$_3$) δ1.00 (t, 6 H), 2.39 (s, 3 H), 2.50 (q, 4 H), 3.60 (s, 3 H), 3.61 (s, 2 H), 7.26 (d, 2 H), 7.45 (d, 2 H), 7.83 (d, 2 H), 7.86 (d, 2 H).

Compound 20 has: $^1$H NMR (400 MHz, CDCl$_3$) δ1.00 (t, 12 H), 2.50 (q, 8 H), 3.60 (s, 4 H), 7.46 (d, 4 H), 7.87 (d, 4 H).

Method B. General method for the synthesis of aldehydes

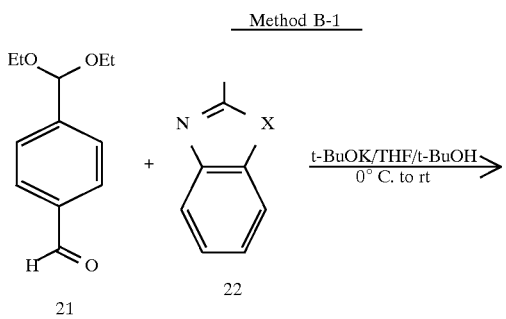

Aldehydes 23 were prepared according to Houpis et al (*J Org. Chem.* 1993, 58, 3176–3178).

EXAMPLES 25) p-[trans-2-(benzoxazol-2-yl)ethenyl]benzaldehyde

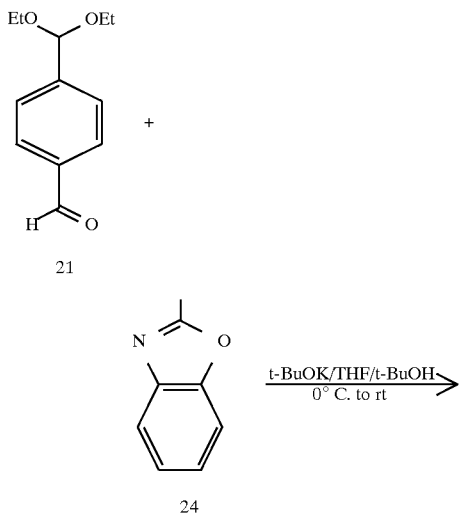

To a solution of terephthaldehyde momo (diethyl acetal) 21 (5.000 g, 24 mmol.), 2-methylbenzoxazole in 5:1 THF-t-BuOH (77.4 mL) cooled at −5° C., was added t-BuOK in THF (1.0M, 36.0 mL, 36.0 mmol.) in such a rate to keep the internal temperature of the reaction below 0° C. (ca. 10 min). The resulting mixture was stirred under nitrogen overnight during which time the temperature rised up to room tempt. It was then diluted with ethyl acetate and washed with sat. sodium bicarbonate. The organic layer was dried ($Na_2SO_4$) and evaporated to give a brown oily solid. It was then dissolved in boiling methanol (50 mL) and cooled to room tempt. The white solid was precipitated out after the addition of water (25 mL) and the solid was collectted. The acetal thus obtained was hydrolysed by stirring the product in 3:1 THF-1N HCl solution for 10 min. The mixture was extracted with ethyl acetate, the organic layers were washed with sat. sodium bicarbonate, brine and dried ($Na_2SO_4$). Evaporation gave a slightly yellow solid 25, 4.43 g (74% overall yield). Compound 25 has: $^1$H NMR (400 MHz, $CDCl_3$) δ7.14 (d, 1 H), 7.31 (m, 2 H), 7.49 (m, 1 H), 7.68 (m, 3 H), 7.75 (d, 1 H), 7.86 (d, 2 H), 10.00 (s, 1 H).

26) p-[trans-2-(benzthiazol-2-yl)ethenyl]benzaldehyde

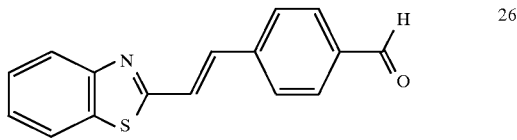

Compound 26 has: $^1$H NMR (400 MHz, $CDCl_3$) δ7.36 (dd, 1 H), 7.44 (dd, 1 H), 7.50 (d, 2 H), 7.68 (d,, 2 H), 7.84 (d, 1 H), 7.88 (d, 2 H), 7.98 (d, 1 H), 9.98 (s, 1 H).

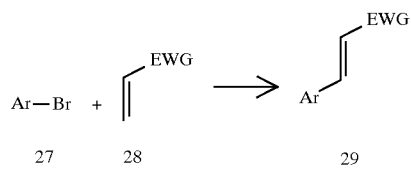

By allowing a compound (27) wherein Ar is defined as above to react with compound (28) wherein EWG is esters and other electron withdrawing groups, under the following condintions, the desired compounds (29) can be obtained.

These reactions may be carried out neat or in a solvent such as dimethylformamide (DMF), tetrahydrofuran (THF), and toluene in the presence of a catalyst (e.g. $Pd(OAc)_2$, $Pd(PPh_3)_4$, $Pd_2dba_3$), a ligand (e.g. $Ph_3P$, $Ph_3As$, $(o\text{-tolyl})_3P$) and a base (e.g. $K_2CO_3$, $CsCO_3$, $Et_3N$) at temperatures ranging from 23° C. to 130° C., for 1 to 60 hours.

EXAMPLES

32) Methyl 4-formyl trans-cinnamate

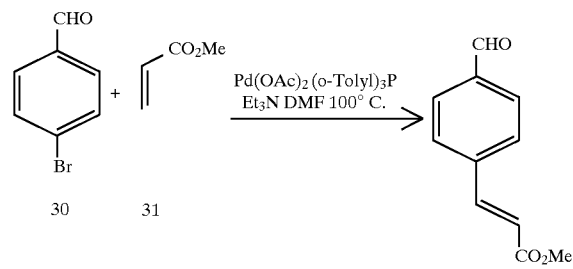

Prepared according to Patel et al (*J. Org. Chem.,* 1977, 42, 3903).

Compound 32 has: $^1$H NMR (400 MHz, $CDCl_3$) δ3.78 (s, 3 H), 6.50 (d, 1 H), 7.63 (m, 3 H), 7.85 (d, 2 H), 9.98 (s, 1 H)..

33) p-[trans-2-(methylsulfonyl)ethenyl]benzaldehyde

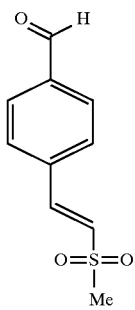

33

Compound 33 has: $^1$H NMR (400 MHz, CDCl$_3$) δ3.00 (s, 3 H), 7.01 (d, 1 H), 7.63 (d, 1 H), 7.64 (d, 2 H), 7.90 (d, 2 H).

Method B-3

36) p-[trans-2-(cyano)ethenyl]benzaldehyde

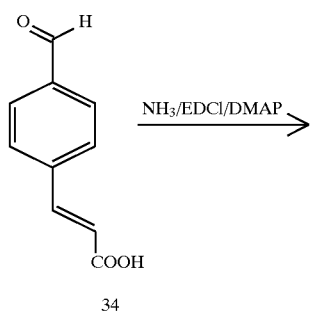

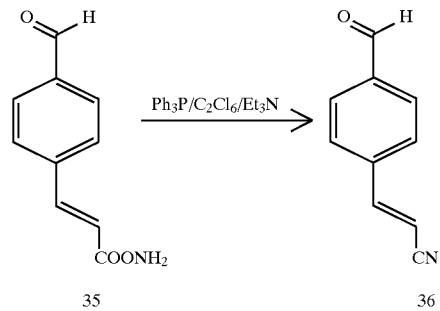

Amonia (0.5M in dioxane, 45 mL, 22.5 mmol.) was added to a suspension of 34 2.10 g, 12 mmol.), EDCI (2.37 g, 14.4 mmol.) and DMAP (0.293 g, 2.4 mmol.) in dichloromethane (50 mL). The resulting mixture was stirred at room tempt overnight. It was then diluted with dichloromethane and washed with 1.0 M hydrochloric acid, followed by sat. sodium bicarbonate. The organic layer was dried (Na$_2$SO$_4$) and evaporated to give 1.244 g of compound 35 as a sightly yellow solid.

To a solution of Compound 35 (340 mg, 1.94 mmol.) in dichloromethane (20.0 mL) was added triethylamine (1.62 mL, 11.64 mmol.), thriphenylphosphine (1.5 g, 5.8 mmol.) and hexachloroethane (1.37 g, 5.8 mmol.). The resulting mixture was stirred at room temperature for 10 min and evaporated. Flash chromatography of the residue (silica, 2.0×10 cm) by using 20 and 30% ethyl acetate—hexanes gave compound 36, 118 mg. Compound 36 has: 1 H NMR (400 MHz, CDCl$_3$) δ5.98 (d, 1 H), 7.57 (d, 2 H), 7.61 (d, 1 H), 7.87 (d, 2 H), 1.00 (s, 1 H).

Method B-4

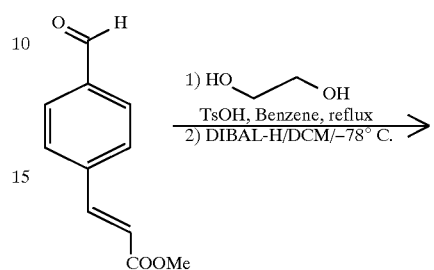

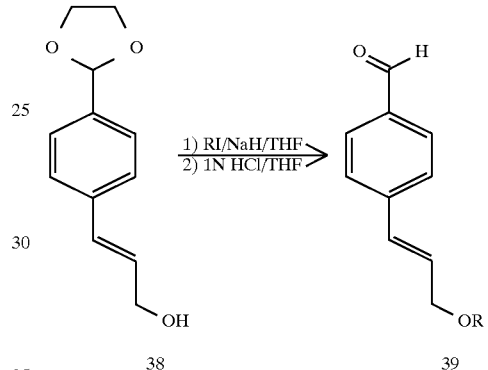

A solution of aldehyde 37 (2.3 g, 12.1 mmol), ethylene glycol (1.35 mL, 24.2 mmol), and p-toluenesulfonic acid (10 mg, catalytic amount) in benzene (30.0 mL) was refluxed for 2 h. Then it was diluted with ethyl acetate and washed with sat. aqueous sodium bicarbonate and brine, dried (Na$_2$SO$_4$), evaporated. The crude material thus obtained was dissolved in dichloromethane (DCM, 100.0 mL) and cooled to −78° C. DIBAL-H (1.0M in DCM, 45 mL, 45.0 mmol) was added over 20 min. Aqueous NaOH (1.0M, 100 mL) was added and the mixture was warmed to room temperature (23° C.) and the layers were separated. The aqueous layer was extracted with DCM (×3), and the combined organic layers were dried (Na$_2$SO$_4$) and evaporated. Flash chromatography of the residue over silica gel gave the desired allylic alcohol 37. Compound 37 has: $^1$H NMR (400 MHz, CDCl$_3$) δ4.00 (d, 2 H), 4.10 (m, 2 H), 4.30 (d, 2 H), 6.35 (dt, 1 H), 6.60 (d, 1 H), 7.48 (m, 4 H).

Alkylation of allylic alcohol 38 with alkyl iodide and sodium hydride in THF following the standard procedure (Jung, M. E. et aL, *Tetrahedron Lett.*, 1989, 30, 641) and hydrolysis of the resulting acetal with 1N aqueous HCl gave the corresponding allylic ether 39.

EXAMPLES 40) p-(3-methoxy-trans-1-propen-1-yl) benzaldehyde

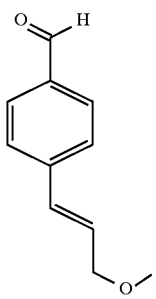

Compound 40 has: $^1$H NMR (400 MHz, CDCl$_3$) δ3.20 (s, 3 H), 4.10 (d, 2 H), 6.40 (dt, 1 H), 6.64 (d, 1 H), 7.49 (d, 2 H), 7.80 (d, 2 H).

41) p-(3-ethoxy-trans-1-propen-1-yl) benzaldehyde

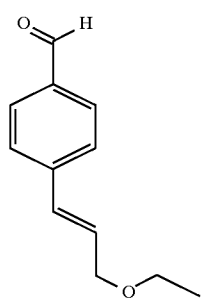

Compound 41 has: $^1$H NMR (400 MHz, CDCl$_3$) δ1.23 (t, 3 H), 3.54 (q, 2 H), 4.14 (d, 2 H), 6.42 (dt, 1 H), 6.64 (d, 1 H), 7.49 (d, 2 H), 7.79 (d, 2 H).

42) p-(3-benzyloxy-trans-1-propen-1-yl) benzaldehyde

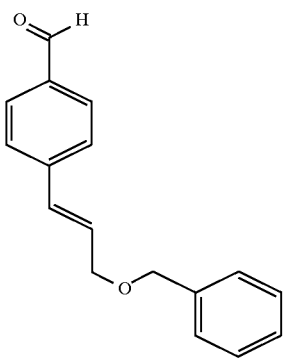

Compound 42 has: $^1$H NMR (400 MHz, CDCl$_3$) δ4.20 (d, 2 H), 4.56 (s, 2 H), 6.46 (dt, 1 H), 6.67 (d, 1 H), 7.34 (m, 5 H), 7.49 (d, 2 H), 7.79 (d, 2 H).

43) p-(3-butyloxy-trans-1-propen-1-yl) benzaldehyde

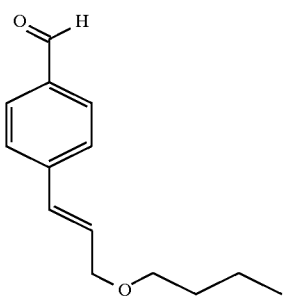

Compound 43 has: $^1$H NMR (400 MHz, CDCl$_3$) δ0.90 (t, 3 H), 1.39 (m, 2 H), 1.57 (m, 2 H), 3.47 (t, 2 H), 4.13 (d, 2 H), 6.43 (m, 1 H), 6.64 (d, 1 H), 7.49 (d, 2 H), 7.79 (d, 2 H), 9.94 (s, 1 H).

44) p-[3-(2-methoxyethyl)-trans-1-propen-1-yl)]benzaldehyde

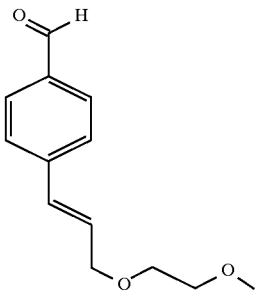

Compound 44 has: $^1$H NMR (400 MHz, CDCl$_3$) δ3.38 (s, 3 H), 3.55 (m, 2 H), 3.64 (m, 2 H), 4.20 (d, 2 H), 6.43 (m, 1 H), 6.64 (d, 1 H), 7.48 (d, 2 H), 7.79 (d, 2 H), 9.94 (s, 1 H).

Method B-5

46) p-(3-phenoxy-trans-1-propen-1-yl) benzaldehyde

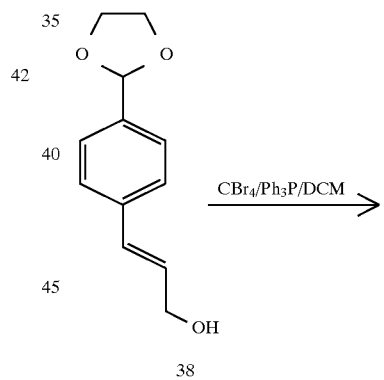

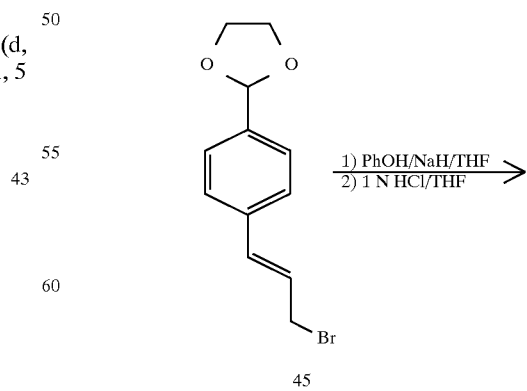

-continued

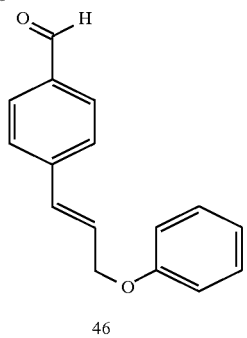

46

Carbon tetrabromide (723 mg, 2.18 mmol) was added, in one prtion, to a solution of allylic alcohol 38 (300 mg, 1.45 mmol), and triphenylphosphine (456 mg, 1.75 mmol) in DCM at room temperature (23° C.). After 2 min, sat aqueous sodium bicarbonate was added and the layers were separated. The aqueous layer was extracted with DCM once and the combined organic layers were dried ($Na_2SO_4$), and evaporated. Flash chromatography of the residue over silica gel gave a white solid 344 mg (88%). Allylic bromide 45 has: $^1$H NMR (400 MHz, $CDCl_3$) δ4.20 (d, 2 H), 4.56 (s, 2 H), 6.46 (dt, 1 H), 6.67 (d, 1 H), 7.34 (m, 5 H), 7.49 (d, 2 H), 7.79 (d, 2 H).

The mixture of allylic bromide 45 (50 mg, 0.185 mmol), phenol (35 mg, 0.37 mmol), and sodium hydride (excess) in THF (2.0 mL) was heated at 50° C. for 5 h. 1N aqueous HCl was added after cooling down to 23° C., 20 min later, the mixture ws diluted with ethyl acetate and washed with 1N NaOH. The organic layer was dried ($Na_2SO_4$), and evaporated. Purification of the residue on preparative TLC gave the desired aldehyde 46, 24 mg, as a white solid. Compound 46 has: $^1$H NMR (400 MHz, $CDCl_3$) δ4.70 (d, 2 H), 6.55 (dt, 1 H), 6.77 (d, 1 H), 6.94 (m, 3 H), 7.28 (m, 2 H), 7.51 (d, 2 H), 7.81 (d, 2 H), 9.98 (s, 1 H).

47) p-[3-(3,4-dimethoxyphenoxy)-trans-1-propen-1-yl) benzaldehyde

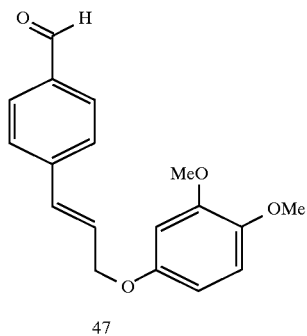

47

Compound 47 has: $^1$H NMR (400 MHz, $CDCl_3$) δ3.80 (s, 3 H), 3.82 (s, 3 H), 4.63 (d, 2 H), 6.44 (m, 1 H), 6.54 (m, 2 H), 6.75 (m, 2 H), 7.50 (d, 2 H), 7.79 (d, 2 H), 9.96 (s, 1 H).

Method B-6

48) p-[3-(1-morpholino)-trans-1-propen-1-yl] benzaldehyde

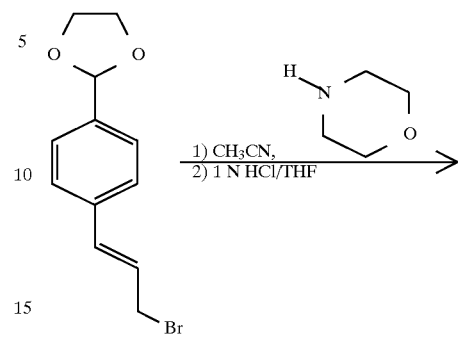

45

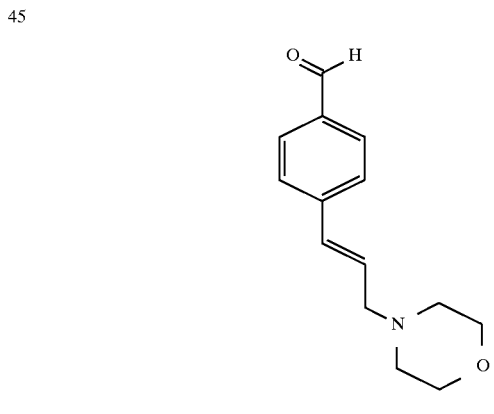

48

Morpholine (82 mL, 0.945 mmol) was added to a solution of allylic bromide 45 in acetonitrile (3.0 mL). 30 min later, 1N aqueous HCl was added and the resulting mixture was stirred for 20 min. It was then diluted with ethyl acetate and washed with sat. aqueous $Na_2CO_3$, dried ($Na_2SO_4$). Evaporation off the solvents gave the desired product 48, 55 mg. Compound 48 has: $^1$H NMR (400 MHz, $CDCl_3$) δ2.50 (m, 4 H), 3.20 (d, 2 H), 3.64 (m, 4 H), 6.46 (m, 1 H), 6.65 (d, 1 H), 7.58 (d, 2 H), 7.82(d, 2 H), 9.92 (s, 1 H).

49) p-[3-(1-piperidino)-trans-1-propen-1-yl] benzaldehyde

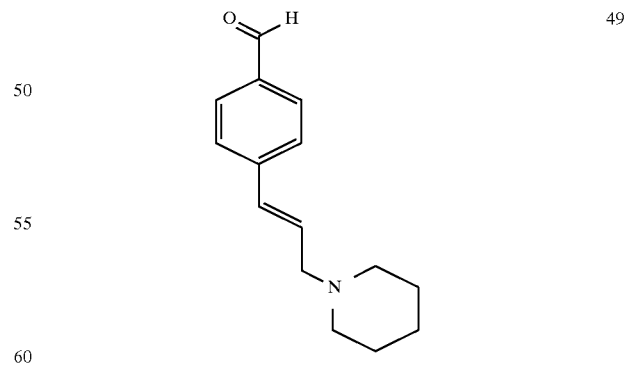

49

Compound 49 has: $^1$H NMR (400 MHz, $CDCl_3$) δ1.24 (m, 2 H), 1.60 (m, 4 H), 2.50 (m, 4 H), 3.18 (d, 2 H), 6.46 (m, 1 H), 6.64 (d, 1 H), 7.58 (d, 2 H), 7.82(d, 2 H), 9.92 (s, 1 H).

50) p-(3-N,N-dimethylamino-trans-1-propen-1-yl) benzaldehyde

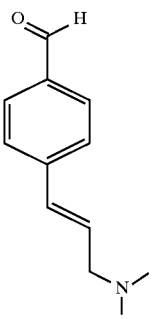

50

Compound 50 has: ¹H NMR (400 MHz, CDCl₃) δ2.30 (s, 6 H), 3.18 (d, 2 H), 6.46 (m, 1 H), 6.64 (d, 1 H), 7.58 (d, 2 H), 7.82(d, 2 H), 9.92 (s, 1 H).

Method B-7

51) p-(3-N,N-diethylcarbamate-trans-1-propen-1-yl) benzaldehyde

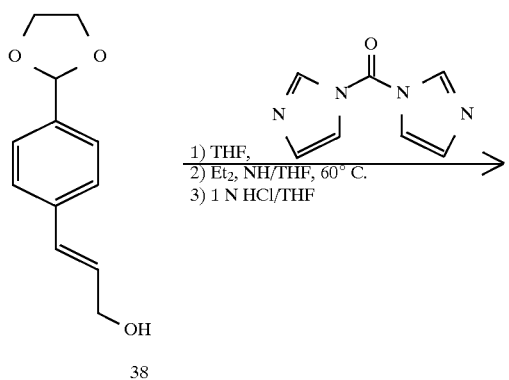

38

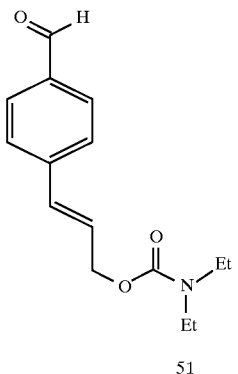

51

Carbonyl diimidazole (66 mg, 0.407 mmol) was added to a solution of allylic alcohol 38 (42 mg, 0.204 mmol) in THF. The resulting mixture was stirred for 1 h at 23° C. and diethylamine (63 mL, 0.612 mmol). It was then heated up to 60 ° C. for overnight. 1N HCl was then added and the resulting mixture was stirred for 20 min. It was then diluted with ethyl acetate and washed with water. The organic layer was dried and evaporated. The crude material (30 mg) was chromatographically pure. Compound 51 has: ¹H NMR (400 MHz, CDCl₃) δ1.10 (t, 6 H), 3.28 (m, 4 H), 4.75 (d, 2 H), 6.44 (m, 1 H), 6.62 (d, 1 H), 7.50 (d, 2 H), 7.80 (d, 2 H), 9.95 (s, 1 H).

Method B-8

52) p-[trans-(2-methoxycarbonylcyclopropan-1-yl] benzaldehyde

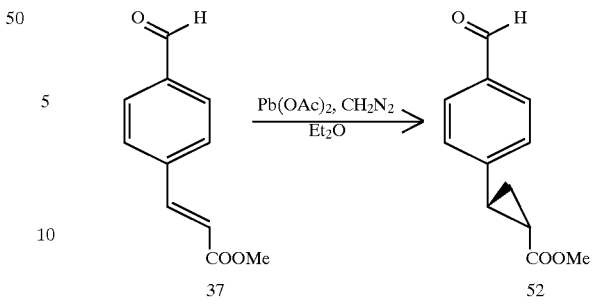

Diazomethane (0.3 M in Et₂O, 8.6 mL, 2.6 mmol) was added to a suspension of compound 37 (123 mg, 0.64 mmol), palladium acetate (catalytic amount) in ether (1.0 mL). After stirring at 23° C. overnight, it was quenched with acetic acid. The mixture was diluted with DCM, washed with sat. aqueous sodium carbonate, and dried (Na₂SO₄). Evaporation off the solvents gave the desired compound as an oil (99 mg). Compound 52 has: ¹H NMR (400 MHz, CDCl₃) δ1.35 (m, 1 H), 1.60 (m, 1 H), 1.92 (m, 1 H), 2.50 (m, 1 H), 3.64 (s, 3 H), 7.18 (d, 2 H), 7.78 (d, 2 H), 9.90 (s, 1 H).

Method C. General Procedure for the Preparation of Imidazoles:

Method 1

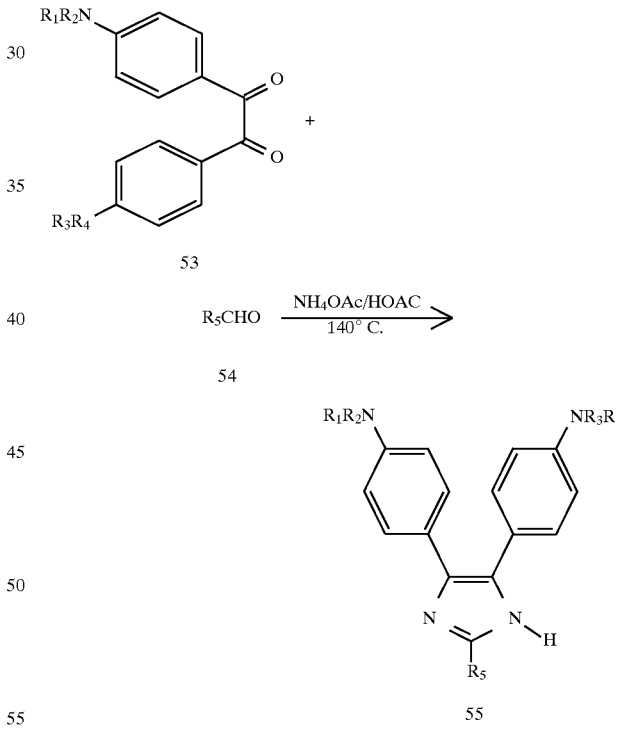

Imidazoles 55 were synthesed according to modified literature procedure (Krieg et al Z Naturforsch teil 1967, 22b, 132).

The proper dione (3.04 mmol.) and aldehyde (4.56 mmol.) were placed in acetic acid (5.85 mL) and ammonium acetate (30.4 mmol.) was placed in acetic acid (1.75 mL) in a separated reaction flask. Both of the flasks were heated in an preheated oil bath (140° C.). As soon as the solids in the two flasks were dissolved, poured the hot solution of ammonium acetate in acetic acid into the other flask which contains the aldehyde and dione. The resulting mixture was heated at 140° C. for 40 min. It was then cooled to room temperature. The pH of solution was adjusted to 0.8 using 3.0M hydrochloric acid. It was then extracted with ether (5 times) to remove the unreacted aldehyde and dione). The aqueous layer was neutralized to pH 8 with 3M sodium hydroxide and extracted with methylenechloride (3 times). The organic layers were dried ($N_2SO_4$) and evaporated to give the corresponding imidazole compound.

EXAMPLE 56

2-[trans-2-(2-benzoxazolyl)ethenylphenyl]-4,5-bis (4-N,N-dimethylaminophenyl) imidazole:

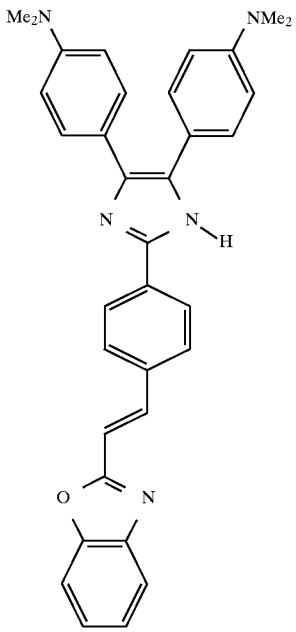

$^1$H NMR (400 MHz, $CDCl_3$) δ2.95 (s, 12 H), 6.55 (d, 4 H), 6.90 (d, 1 H), 7.21 (m, 6 H), 7.39 (m, 1 H), 7.50 (m, 3 H), 7.63 (d, 1 H), 7.83 (d, 2 H); ESIMS, m/z for $C_{34}H_{31}ON_5$ [M+H]$^+$: 526.

EXAMPLE 57

2-[trans-2-(2-benzoxazolyl)ethenylphenyl]-4-(4-N,N-dimethylaminophenyl)-5-(4-N-methylaminophenyl) imidazole:

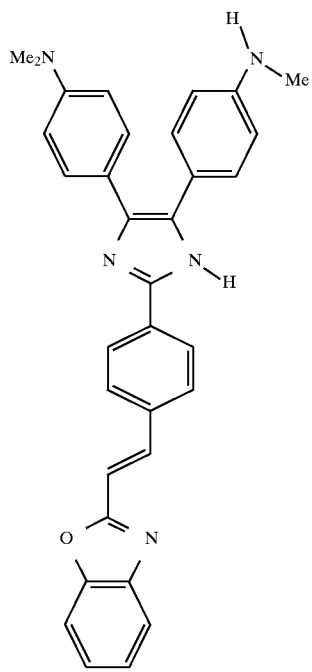

$^1$H NMR (400 MHz, $CD_3OD$) δ2.78 (s, 3 H), 2.95 (s, 6 H), 6.51 (d, 2 H), 6.63 (d, 2 H), 6.98 (d, 2 H), 7.36 (in, 8 H), 7.64 (m, 1 H), 7.70 (d, 1 H), 7.85 (d, 2 H); ESIMS, m/z for $C_{33}H_{29}ON_5$ [M+H]$^+$: 512.

EXAMPLE 58

2-[trans-2-(2-benzoxazolyl)ethenylphenyl]-4-(4-N,N-diethylaminophenyl)-5-(4-N-methylaminophenyl) imidazole:

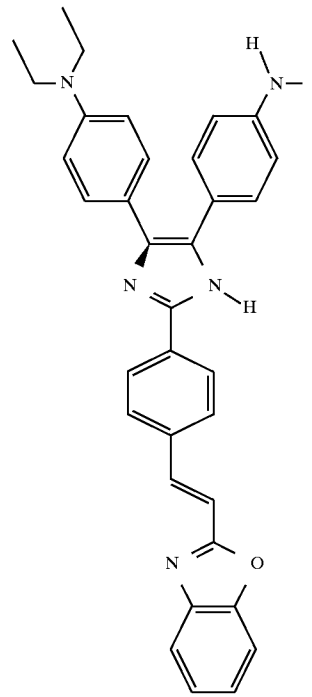

$^1$H NMR (400 MHz, CDCl$_3$) δ1.12 (t, 6 H), 2.80 (s, 3 H), 3.31 (q, 4 H), 6.53 (d, 2 H), 6.59 (d, 2 H), 6.98 (d, 1 H), 7.29 (m, 2 H), 7.39 (m, 4 H), 7.49 (m, 1 H), 7.52 (d, 2 H), 7.65 (m, 1 H), 7.70 (d, 1 H), 7.86 (d, 2 H); ESIMS, m/z for C$_{35}$H$_{33}$ON$_5$ [M+H]$^+$: 540.

EXAMPLE 59

2-[trans-2-(2-benzoxazolyl)ethenylphenyl]-4-(4-N-disopropylaminophenyl)-5-(4-N-methylaminophenyl) imidazole:

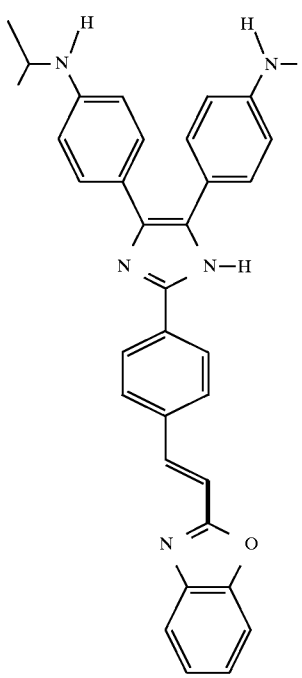

59

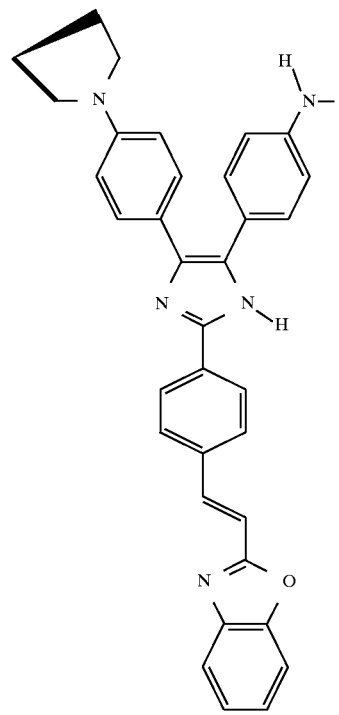

60

$^1$H NMR (400 MHz, CDCl$_3$) δ1.95 (br s, 4 H), 2.80 (br s, 3 H), 3.30 (br s, 4 H), 6.50 (m, 4 H), 7.00 (br d, 1 H), 7.22–7.90 (m, 13 H); ESIMS, m/z for C$_{35}$H$_{31}$ON$_5$ [M+H]$^+$: 538.

EXAMPLE 61

2-[trans-2-(2-benzoxazolyl)ethenylphenyl]-4-(4-N,N-dimethylaminophenyl)-5-[4-(2-methoxyethylamino)phenyl] imidazole:

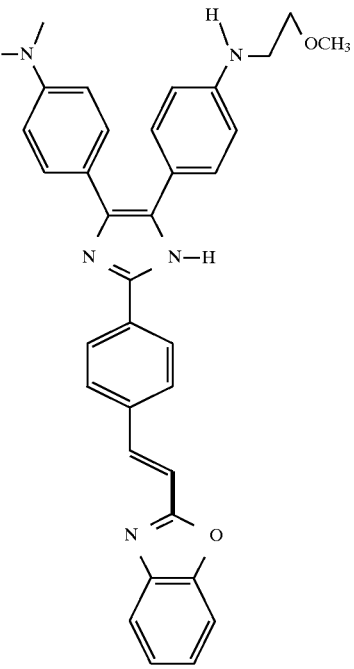

61

$^1$H NMR (400 MHz, CDCl$_3$) δ1.14 (s, 3 H), 1.16 (s, 3 H), 2.76 (s, 3 H), 3.56 (m, 1 H), 6.48 (m, 4 H), 6.92 (d, 1 H), 7.31 (m, 6 H), 7.46 (m, 3 H), 7.62 (m, 1 H), 7.66 (d, 1 H), 7.83 (d, 2 H); ESIMS, m/z for C$_{34}$H$_{31}$ON$_5$ [M+H]$^+$: 526.

EXAMPLE 60

2-[trans-2-(2-benzoxazolyl)ethenylphenyl]-4-(4-N-methylaminophenyl)-5-(4-pyrrolidinophenyl) imidazole:

$^1$H NMR (400 MHz, CDCl$_3$) δ2.90 (s, 6 H), 3.24 (br s, 2 H), 3.35 (s, 3 H), 3.56 (t, 2 H), 6.54 (d, 2 H), 6.63 (d, 2 H), 6.97 (d, 1 H), 7.24–7.44 (m, 6 H), 7.49 (m, 3 H), 7.64 (m, 1 H), 7.69 (s, 1 H), 7.85 (d, 2 H); ESIMS, m/z for C$_{35}$H$_{33}$O$_2$N$_5$ [M+H]$^+$: 556.

EXAMPLE 62

2-[trans-2-(2-benzthiazolyl)ethenylphenyl]-4,5-bis (4-N,N-dimethylaminophenyl) imidazole:

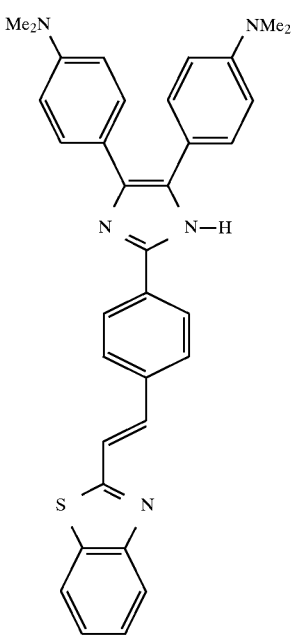

$^1$H NMR (400 MHz, CDCl$_3$) δ2.85 (s, 12 H), 6.62 (d, 4 H), 7.26–7.56 (m, 9 H), 7.76–7.88 (m, 3 H), 7.92 (d, 2 H); ESIMS, m/z for C$_{34}$H$_{31}$SN$_5$ [M+H]$^+$: 542.

EXAMPLE 63

2-[trans-2-(2-benzthiazolyl)ethenylphenyl]-4-(4-N-dimethylaminophenyl)-5-(4-N-methylaminophenyl) imidazole:

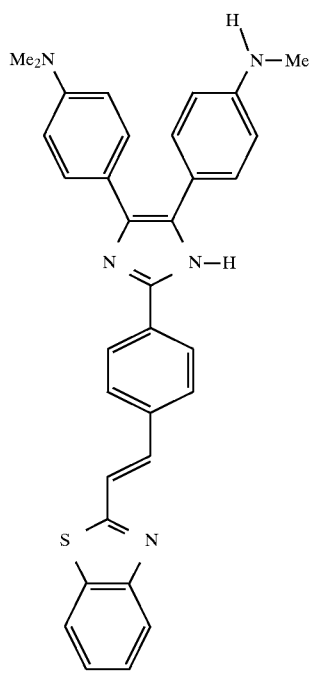

$^1$H NMR (400 MHz, CDCl$_3$) δ2.80 (s, 3 H), 2.90 (s, 6 H), 6.53 (d, 2 H), 6.64 (d, 4 H), 7.26–7.50 (m, 6 H), 7..54 (d, 2 H), 7.80 (d, 1 H), 7.85 (d, 2 H), 7.93 (d, 1 H); ESIMS, m/z for C$_{33}$H$_{29}$SN$_5$ [M+H]$^+$: 528.

EXAMPLE 64

2-[trans-2-(2-cyano)ethenylphenyl]-4, 5-(4-N,N-dimethylaminophenyl) imidazole:

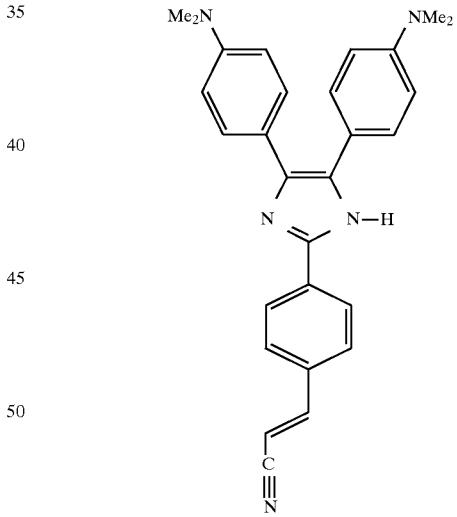

$^1$H NMR (400 MHz, CDCl$_3$) δ2.95 (s, 12 H), 5.80 (d, 1 H), 6.65 (d, 4 H), 7.40 (m, 7 H), 7.85 (br s, 2 H); ESIMS, m/z for C$_{28}$H$_{27}$N$_5$ [M+H]$^+$: 434.

EXAMPLE 65

2-[trans-2-(2-cyano)ethenylphenyl]-4-(4-N,N-dimethylaminophenyl)-5-[4N-(2-methoxyethyl)amino)phenyl] imidazole:

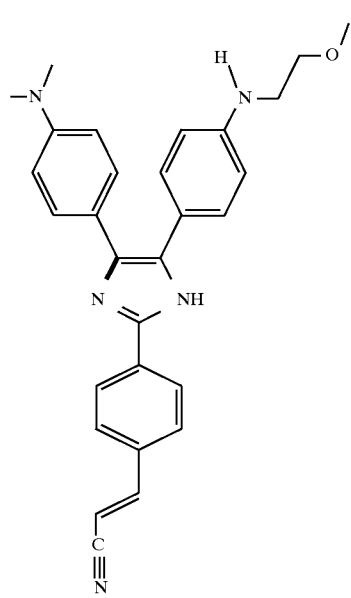

$^1$H NMR (400 MHz, CD$_3$OD) δ2.92 (s, 6 H), 3.25 (m, 2 H), 3.34 (s, 3 H), 3.54 (t, 2 H), 6.20 (d, 1 H), 6.60 (d, 2 H), 6.70 (d, 2 H), 7.26 (m, 4 H), 7.50 (d, 1 H), 7.60 (d, 2 H), 7.96 (d, 2 H); ESIMS, m/z for C$_{29}$H$_{29}$N$_5$O[M+H]$^+$: 464.

EXAMPLE 66

2-(trans-2-methoxycarbonyl-ethenylphenyl)-4-(4-N,N-diallylaminophenyl)5-(4-fluoro-phenyl) imidazole:

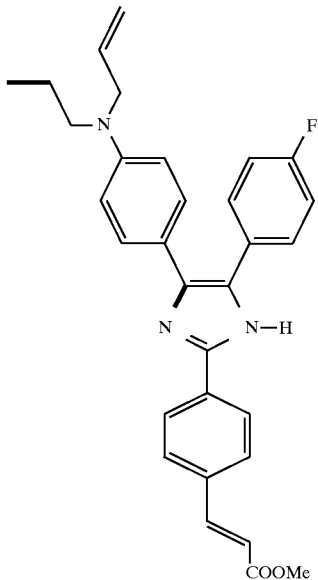

Compound 66 was prepared according the method C by using the proper dione and aldehyde. Compound 66 has: $^1$H NMR (400 MHz, CDCl$_3$) δ3.76 (s, 3 H), 3.91 (s, 4 H), 5.16 (m, 4 H), 5.83 (m, 2 H), 6.41 (d, 1 H), 6.63 (d, 2 H), 6.96 (m, 2 H), 7.24 (d, 2 H), 7.57 (m, 5 H), 7.84 (d, 2 H); ESIMS, m/z for C$_{31}$H$_{28}$O$_2$N$_3$F [M+H]$^+$: 494.

EXAMPLE 67

2-(trans-2-methoxycarbonyl-ethenylphenyl)-4-(4-N-methylaminophenyl)5-(4-pyrrolidinophenyl) imidazole:

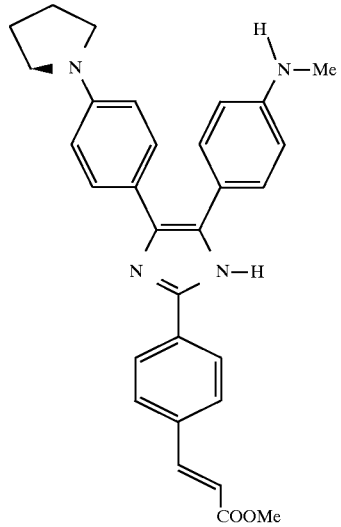

Compound 67 was prepared according the method C by using the proper dione and aldehyde. Compound 67 has: $^1$H NMR (400 MHz, CD$_3$OD) δ1.96 (m, 4 H), 2.74 (s, 3 H), 3.10 (s, 4 H), 3.78 (s, 3 H), 6.42–6.56 (m, 5 H), 7.24 (dd, 4 H), 7.58 (d, 2 H), 7.64 (d, 1 H), 7.91 (d, 2 H); ESIMS, m/z for C$_{30}$H$_{30}$O$_2$N$_4$ [M+H]$^+$: 479.

EXAMPLE 68

2-(trans-2-methoxycarbonyl-ethenylphenyl) -4- (4-N-methylaminophenyl)5-(4-piperidinophenyl) imidazole:

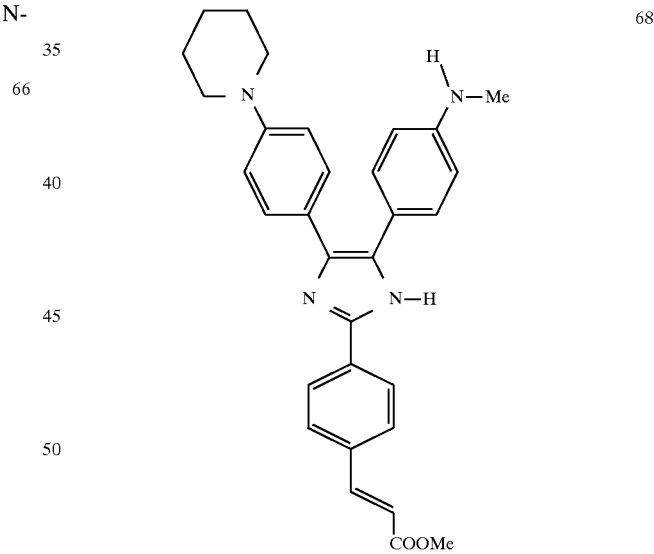

Compound 68 was prepared according the method C by using the proper dione and aldehyde. Compound 68 has: $^1$H NMR (400 MHz, CD$_3$OD) δ1.54 (m, 2 H), 1.64 (m, 4 H), 2.74 (s, 3 H), 3.08 (s, 4 H), 3.78 (s, 3 H), 6.48 (d, 1 H), 6.54 (d, 2 H), 6.85 (d, 2 H), 7.20 (d, 2 H), 7.31 (d, 2 H), 7.58 td, 2 H), 7.63 (d, 1 H), 7,.91 (d, 2 H); ESIMS, m/z for C$_{31}$H$_{32}$O$_2$N$_4$ [M+H]$^+$: 493.

EXAMPLE 69

2-(trans-2-methoxycarbonyl-ethenylphenyl)-4-[4-N,N-di(2methoxyethyl)aminophenyl]-5-(4-N-methylaminophenyl) imidazole:

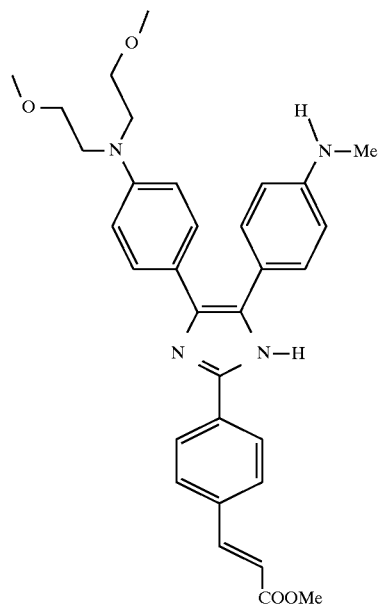

¹H NMR (400 MHz, CDCl₃) δ2.82 (s, 3 H), 3.30 (s, 6 H), 3.52 (m, 8 H), 3.80 (s, 3 H), 6.42 (d, 1 H), 6.60 (m, 4 H), 7.30–7.60 (m, 6 H), 7.68 (d, 1 H), 7.90 (br s, 2 H); ESIMS, m/z for $C_{32}H_{36}O_4N_4$ [M+H]⁺: 541.

EXAMPLE 70

2-(trans-2-methoxycarbonyl-ethenylphenyl)-4-[4-(1-imidazolyl)phenyl]-5(4-N-methylaminophenyl) imidazole:

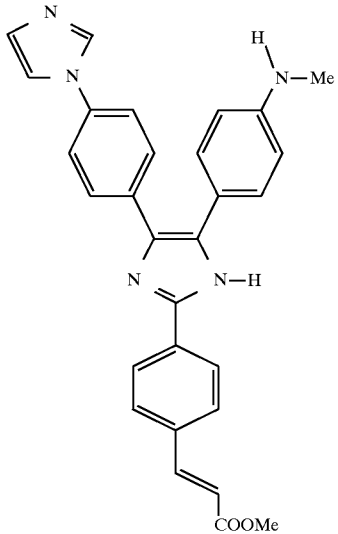

¹H NMR (400 MHz, CDCl₃) δ2.80 (s, 3 H), 3.72 (s, 3 H), 6.36 (d, 1 H), 6.53 (d, 2 H), 7.06 (s, 1 H), 7.21 (d, 4 H), 7.48 (d, 2 H), 7.59 (d, 1 H), 7.62 (d, 2 H), 7.74 (s, 1 H), 7.89 (d, 2 H); ESIMS, m/z for $C_{29}H_{25}O_2N_5$ [M+H]⁺: 476.

EXAMPLE 71

2-(trans-2-methoxycarbonyl-ethenylphenyl)-4, 5-bis (4-N-morpholinophenyl) imidazole:

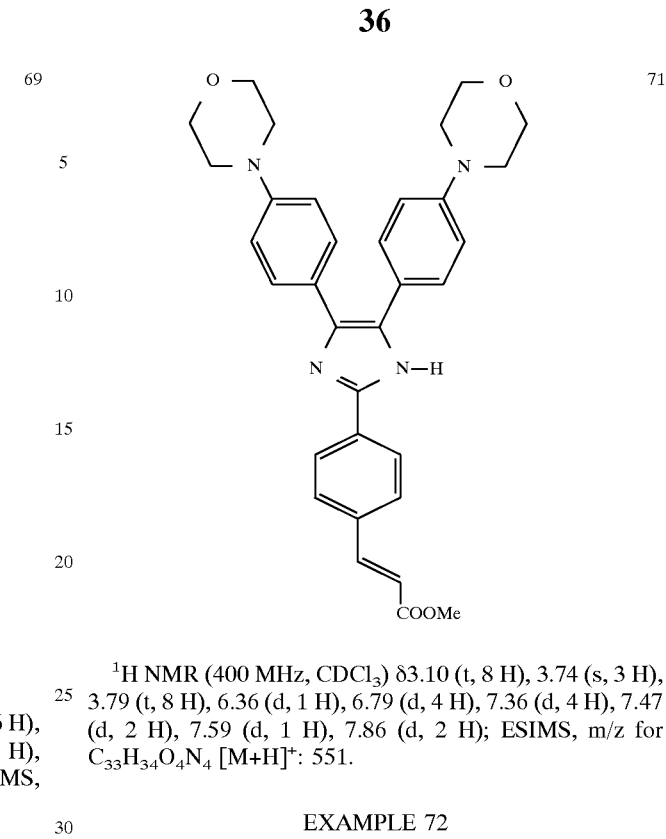

¹H NMR (400 MHz, CDCl₃) δ3.10 (t, 8 H), 3.74 (s, 3 H), 3.79 (t, 8 H), 6.36 (d, 1 H), 6.79 (d, 4 H), 7.36 (d, 4 H), 7.47 (d, 2 H), 7.59 (d, 1 H), 7.86 (d, 2 H); ESIMS, m/z for $C_{33}H_{34}O_4N_4$ [M+H]⁺: 551.

EXAMPLE 72

2-(trans-2-methoxycarbonyl-ethenylphenyl)-4-(4-N-dimethylaminophenyl)-5-(4-N-morpholinophenyl) imidazole:

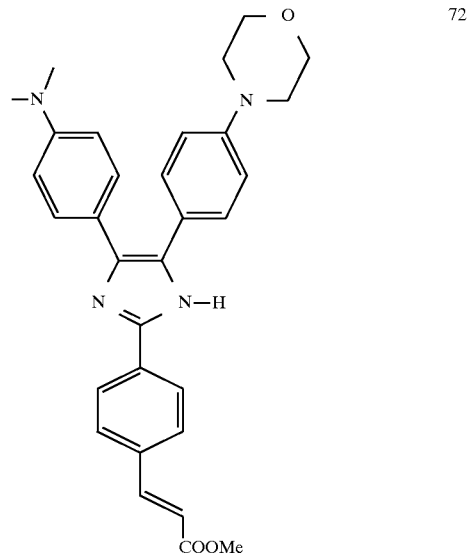

¹H NMR (400 MHz, CDCl₃) δ2.90 (br s, 6 H), 3.10 (br s, 4 H), 3.76 (s, 3 H), 3.82 (m, 4 H), 6.40 (d, 1 H), 6.65 (d, 2 H), 6.81 (d, 2 H), 7.28–7.56 (m, 6 H), 7.63 (d, 1 H), 7.84 (d, 2 H); ESIMS, m/z for $C_{31}H_{32}O_3N_4$ [M+H]⁺: 506.

EXAMPLE 73

2-(trans-2-methoxycarbonyl-ethenylphenyl)-4-(4-N-methylaminophenyl)5-(4-N-morpholinophenyl) imidazole:

37

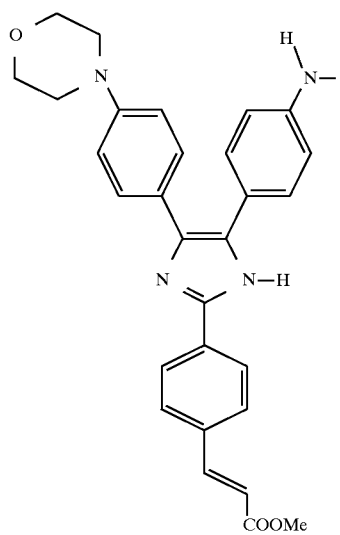

¹H NMR (400 MHz, CDCl₃) δ2.80 (br s, 3 H), 3.10 (m, 4 H), 3.76 (s, 3 H), 3.82 (t, 4 H), 6.37 (d, 1 H), 6.52 (d, 2 H), 6.80 (d, 2 H), 7.28–7.56 (m, 6 H), 7.61 (d, 1 H), 7.83 (d, 2 H); ESIMS, m/z for $C_{30}H_{30}O_3N_4$ [M+H]⁺: 495.

EXAMPLE 74

2-[4-(3-methoxy-trans-1-propen-1-yl)phenyl]-4,5-bis (4-N,N-dimnethylaminophenyl) imidazole:

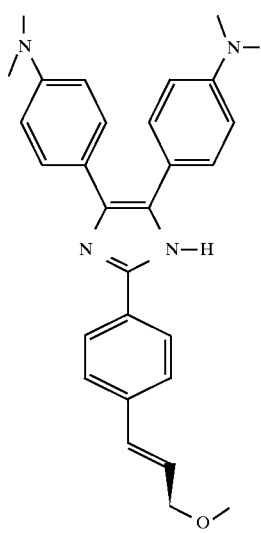

¹H NMR (400 MHz, CD₃OD) δ2.90 (s, 12 H), 3.35 (s, 3 H), 4.10 (d, 2 H), 6.35 (m, 1 H), 6.65 (d, 1 H), 6.70 (d, 4 H), 7.30 (d, 4 H), 7.50 (d, 2 H), 7.90 (d, 2 H); ESIMS, m/z for $C_{29}H_{32}ON_4$ [M+H]⁺: 453.

EXAMPLE 75

2-[4-(3-ethoxy-trans-1-propen-1-yl)phenyl]-4,5-bis (4-N,N-dimethylaminophenyl) imidazole:

38

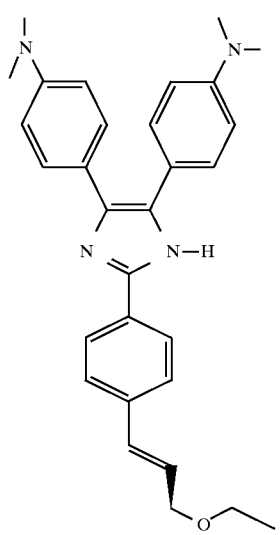

¹H NMR (400 MHz, CD₃OD) δ1.10 (t, 3 H), 2.90 (s, 12 H), 3.50 (q, 2 H), 4.10 (br s, 2 H), 6.35 (m, 1 H), 6.65 (d, 1 H), 6.70 (d, 4 H), 7.30 (br s, 4 H), 7.50 (d, 2 H), 7.90 (br s, 2 H); ESIMS, m/z for $C_{30}H_{34}ON_4$ [M+H]⁺: 467.

EXAMPLE 76

2-[4-(3-ethoxy-trans-1-propen-1-yl)phenyl]-4-(4-N-dimethylaminophenyl)-5-(4-N-methylaminophenyl) imnidazole:

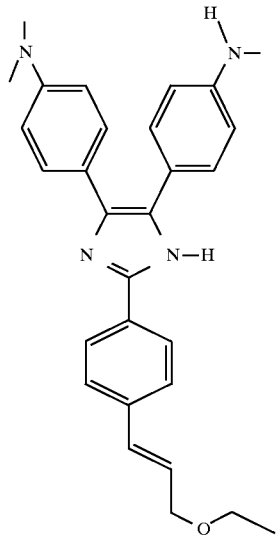

¹H NMR (400 MHz, CD₃OD) δ1.36 (t, 3 H), 2.90 (s, 3 H), 3.08 (s, 6 H), 3.70 (q, 2 H), 4.28 (d, 2 H), 6.45 (m, 1 H), 6.71 (d, 2 H), 6.76 (d, 1 H), 6.85 (d, 2 H), 7.39 (d, 2 H), 7.47 (d, 2 H), 7.60 (d, 2 H), 8.02 (d, 2 H); ESIMS, m/z for $C_{29}H_{32}ON_4$ [M+H]⁺: 453.

EXAMPLE 77

2-[4-(3-benzyloxy-trans-1-propen-1-yl)phenyl]-4, 5-bis (4-N,N-dimethylaminophenyl) imidazole:

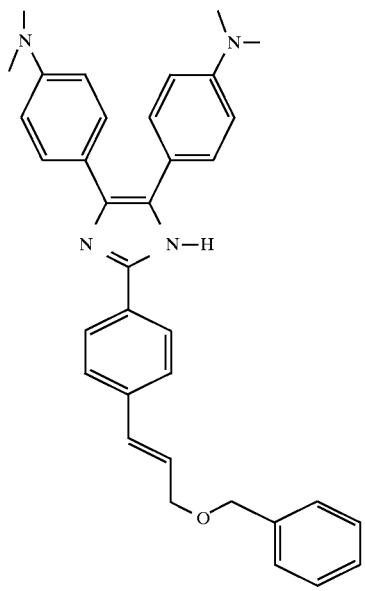

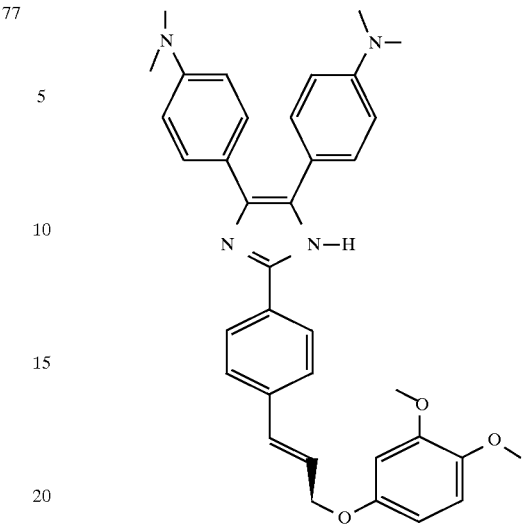

¹H NMR (400 MHz, CD₃OD) δ2.90 (s, 12 H), 4.17 (d, 2 H), 4.54 (s, 2 H), 6.38 (m, 1 H), 6.64 (d, 1 H), 6.69 (d, 4 H), 7.30 (m, 9 H), 7.46 (d, 2 H), 7.86 (d, 2 H); ESIMS, m/z for $C_{35}H_{36}ON_4$ [M+H]⁺: 529.

¹H NMR (400 MHz, CD₃OD) δ2.90 (s, 12 H), 3.70 (s, 3 H), 3.78 (s, 3 H), 5.10 (m, 2 H), 6.30 (m, 1 H), 6.44 (s, 1 H), 6.70 (m, 6 H), 7.30 (m, 7 H), 7.80 (d, 2 H).

EXAMPLE 78

2-[4-(3-phenoxy-trans-1-propen-1-yl)phenyl]-4-(4-N-dimethylaminophenyl)-5-(4-N-methylaminopheny) imidazole:

EXAMPLE 80

2-[4-(3-N,N-diethylamino-trans-1-propen-1-yl)phenyl]-4,5-bis (4-N,N-dimethylaminophenyl) imidazole:

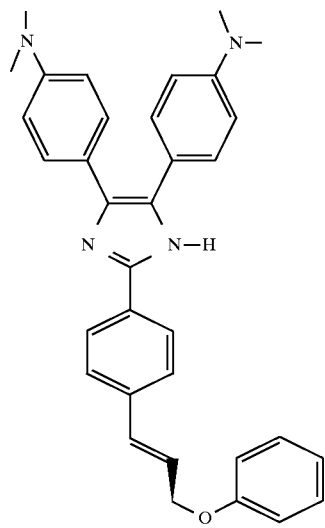

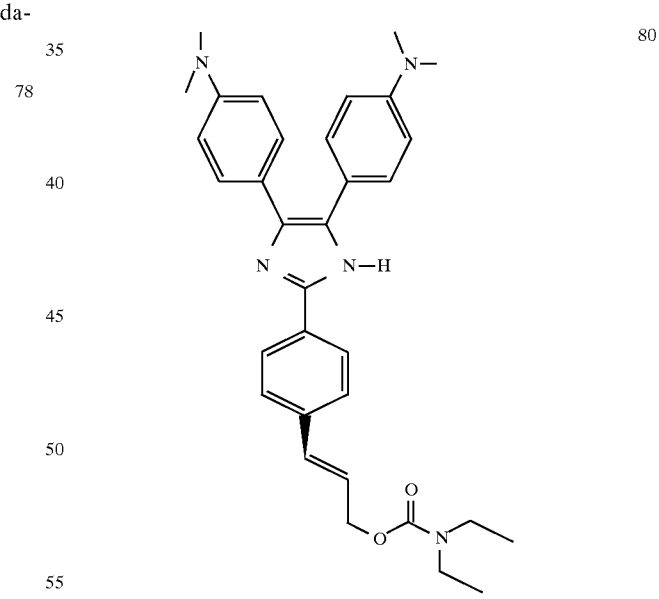

¹H NMR (400 MHz, CD₃OD) δ2.70 (s, 3 H), 2.90 (s, 6 H), 4.68 (d, 2 H), 6.48 (m, 1 H), 6.57 (d, 1 H), 6.72 (m, 4 H), 6.88 (t, 1 H), 6.94 (d, 1 H), 7.24 (m, 4 H), 7.32 (d, 2 H), 7.48 (d, 2 H), 7.88 (d, 2 H).

¹H NMR (400 MHz, CD₃OD) δ1.10 (m, 6 H), 2.90 (s, 12 H), 3.28 (m, 4 H), 4.70 (d, 2 H), 6.34 (m, 1 H), 6.65 (d, 1 H), 6.67 (d, 4 H), 7.30 (d, 4 H), 7.46 (d, 2 H), 7.86 (d, 2 H).

EXAMPLE 79

2-{4-[3-(3,4-dimethoxy-phenoxy)-trans-1-propen-1-yl] phenyl}-4-(4-N-dimethylaminophenyl)-5-(4-N-methylaminopheny) imidazole:

EXAMPLE 81

2- [4-(3-N-morpholino-trans-1-propen-1-yl)phenyl]-4,5-bis (4-N,N-dimethylaminophenyl) imidazole:

41

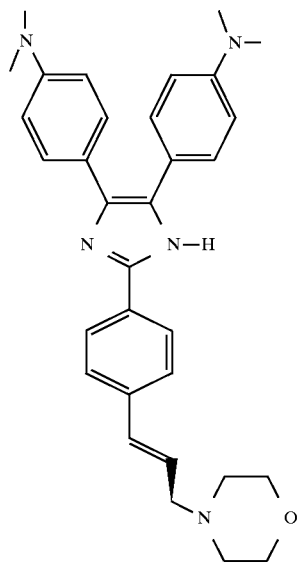

81

¹H NMR (400 MHz, CD$_3$OD) δ2.49 (br s, 4 H), 2.89 (s, 12 H), 3.15 (d, 2 H), 3.67 (dd, 4 H), 6.29 (m, 1 H), 6.58 (d, 1 H), 6.69 (d, 4 H), 7.29 (d, 4 H), 7.44 (d, 2 H), 7.86 (d, 2 H); ESIMS, m/z for C$_{32}$H$_{37}$ONs [M+H]$^+$: 508.

EXAMPLE 82

2-[4-(3-N-piperidino-trans-1-propen-1-yl)phenyl]-4,5-bis (4-N,N-dimethylaminophenyl) imidazole:

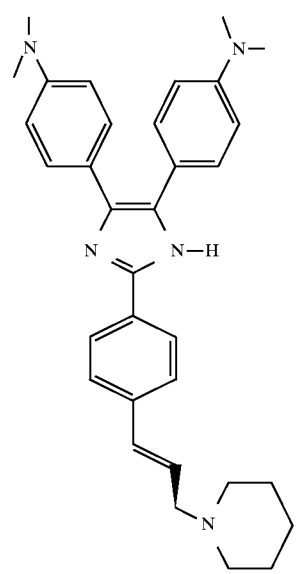

82

¹H NMR (400 MHz, CD$_3$OD) δ1.45 (br s, 2 H), 1.60 (m, 4 H), 2.47 (br s, 4 H), 2.89 (s, 12 H), 3.13 (d, 2 H), 6.30 (m, 1 H), 6.55 (d, 1 H), 6.69 (d, 4 H), 7.29 (d, 4 H), 7.43 (d, 2 H), 7.86 (d, 2 H); ESIMS, m/z for C$_{33}$H$_{39}$N$_5$ [M+H]$^+$: 506.

EXAMPLE 83

2-[4-(3-N,N-dimethylamino-trans-1-propen-1-yl)phenyl] -4,5-bis (4-N,N-dimethylaminophenyl) imidazole:

42

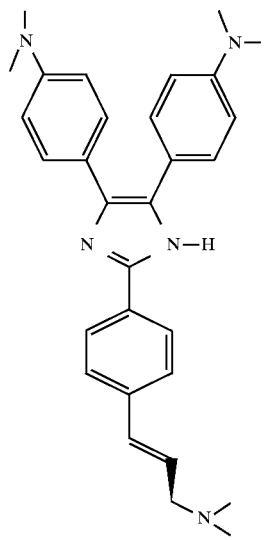

83

¹H NMR (400 MHz, CD$_3$OD) δ2.28 (s, 6 H), 2.89 (s, 12 H), 3.13 (d, 2 H), 6.28 (m, 1 H), 6.56 (d, 1 H), 6.67 (d, 4 H), 7.29 (d, 4 H), 7.43 (d, 2 H), 7.86 (d, 2 H); ESIMS, m/z for C$_{30}$H$_{35}$N$_5$ [M+H]$^+$: 466.

EXAMPLE 84

2-{4-[3-(2-methoxy-ethoxy)-trans-1-propen-1-yl] phenyl}-4, 5-bis (4-N,N-dimethylaminophenyl) imidazole:

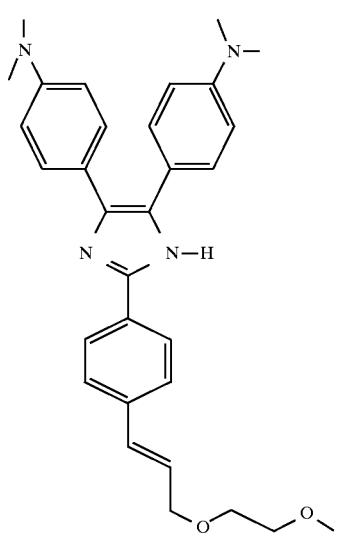

84

¹H NMR (400 MHz, CD$_3$OD) δ2.90 (s, 12 H), 3.34 (s, 3 H), 3.55 (m, 2 H), 3.62 (m, 2 H), 4.16 (d, 2 H), 6.36 (m, 1 H), 6.64 (d, 1 H), 6.70 (d, 4 H), 7.30 (d, 4 H), 7.46 (d, 2 H), 7.87 (d, 2 H); ESIMS, m/z for C$_{31}$H$_{36}$O$_2$N$_4$ [M+H]$^+$: 497.

EXAMPLE 85

2- [4-(3-butoxy-trans-1-propen-1-yl)phenyl]-4,5-bis (4-N,N-dimethylaminophenyl) imidazole:

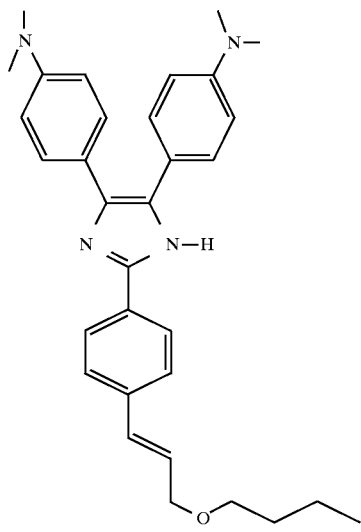

¹H NMR (400 MHz, CD₃OD) δ0.91 (t, 3 H), 1.39 (m, 2 H), 1.56 (m, 2 H), 2.09 (s, 12 H), 3.47 (t, 2 H), 4.10 (d, 2 H), 6.34 (m,. 1 H), 6.61 (d, 2 H), 6.69 (d, 4 H), 7.29 (d, 4 H), 7.44 (d, 2 H), 7.86 (d, 2 H); ESIMS, m/z for $C_{32}H_{38}ON_4$ [M+H]⁺: 495.

EXAMPLE 86

2-[4-(3-ethoxy-trans-1-propen-1-yl)phenyl]-4,5-bis (4-N,N-diethylaminophenyl) imidazole:

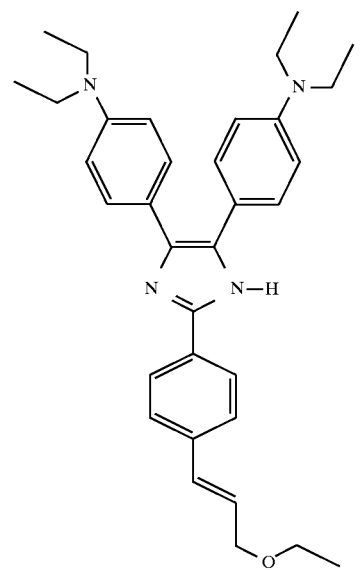

¹H NMR (400 MHz, CD₃OD) δ1.10 (t, 12 H), 1.20 (t, 3 H), 3.30 (br s, 8 H), 3.55 (q, 2 H), 4.08 (d, 2 H), 6.34 (m, 1 H), 6.58 (m, 5 H), 7.20 (d, 4 H), 7.40 (d, 2 H), 7.80(d, 2 H); ESIMS, m/z for $C_{34}H_{42}ON_4$ [M+H]⁺: 523.

EXAMPLE 87

2-[4-(3-ethoxy-trans-1-propen-1-yl)phenyl]-4-(4-N,N-diethylaminophenyl)5-(4-N-methylaminophenyl) imidazole:

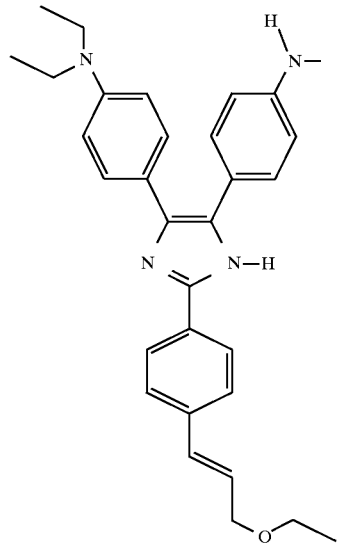

¹H NMR (400 MHz, CD₃OD) δ1.10 (t, 6 H), 1.19 (t, 3 H), 2.74 (s, 3 H), 3.33 (q, 4 H), 3.52 (q, 2 H), 4.10 (d, 2 H), 6.34 (m, 1 H), 6.59 (m, 5 H), 7.25 (m, 4 H), 7.44(d, 2 H), 7.85 (d, 2 H); ESIMS, m/z for $C_{31}H_{36}ON_4$ [M+H]⁺: 481.1

EXAMPLE 88

2-[4-(3-methoxy-trans-1-propen-1-yl)phenyl]-4,5-bis (4-pyrrolidinophenyl) imidazole:

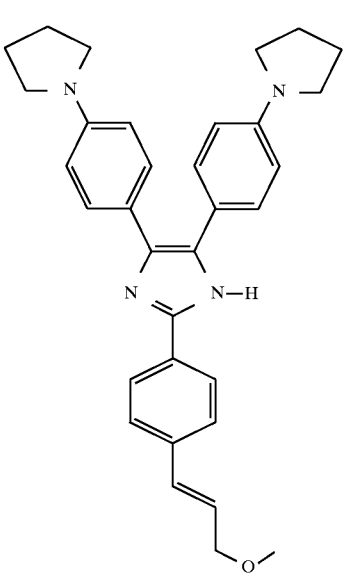

¹H NMR (400 MHz, CD₃OD) δ1.97 (m, 8 H), 3.28 (m, 8 H), 3.36 (s, 3 H), 4.12 (d, 2 H), 6.35 (m, 1 H), 6.50 (d, 4 H), 6.62 (d, 1 H), 7.27 (d, 4 H), 7.46 (d, 2 H), 7.87 (d, 2 H); ESIMS, m/z for $C_{33}H_{36}ON_4$ [M+H]⁺: 505.

EXAMPLE 89

2-[4-(3-ethoxy-trans-1-propen-1-yl)phenyl]-4,5-bis (4-pyrrolidinophenyl) imidazole:

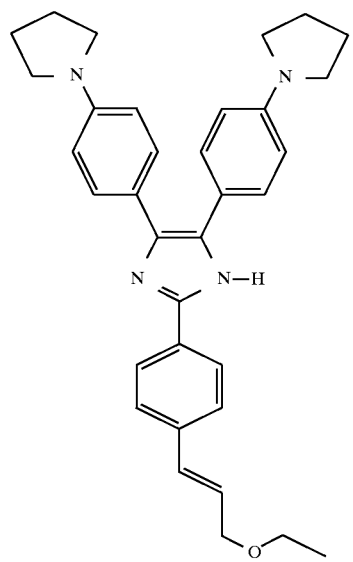

¹H NMR (400 MHz, CD₃OD) δ1.19 (t, 3 H), 1.97 (m, 8 H), 3.28 (m, 8 H), 3.53 (q, 2 H), 4.12 (d, 2 H), 6.35 (m, 1 H), 6.50 (d, 4 H), 6.62 (d, 1 H), 7.27 (d, 4 H), 7.46 (d, 2 H), 7.87 (d, 2 H); ESIMS, m/z for $C_{34}H_{38}ON_4$ [M+H]⁺: 519.

EXAMPLE 90

2-[4-(3-ethoxy-trans-1-propen-1-yl)phenyl]-4-(4-N-dimethylaminophenyl)-5-(4-pyrrolidinophenyl) imidazole:

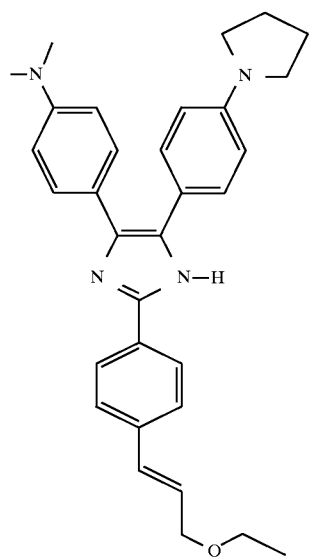

¹H NMR (400 MHz, CD₃OD) δ1.17 (t, 3 H), 1.91 (m, 4 H), 2.85 (s, 6 H), 3.16 (br s, 4 H), 3.50 (q, 2 H), 4.07 (d, 2 H), 6.30 (m, 1 H), 6.43 (d, 2 H), 6.57 (d, 1 H), 6.63 (d, 2 H), 7.21 (d, 2 H), 7.27 (d, 2 H), 7.40 (d, 2 H), 7.82 (d, 2 H); ESIMS, m/z for $C_{32}H_{36}ON_4$ [M+H]⁺: 493.

EXAMPLE 91

2-[4-(3-ethoxy-trans-1-propen-1-yl)phenyl]-4-(4-N-methylaminophenyl)-5(4-pyrrolidinophenyl) imidazole:

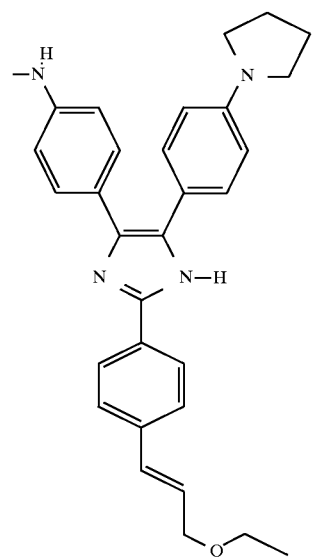

¹H NMR (400 MHz, CD₃OD) δ1.17 (t, 3 H), 1.91 (m, 4 H), 2.85 (s, 3 H), 3.16 (br s, 4 H), 3.50 (q, 2 H), 4.07 (d, 2 H), 6.30 (m, 1 H), 6.43 (d, 2 H), 6.57 (d, 1 H), 6.63 (d, 2 H), 7.21 (d, 2 H), 7.27 (d, 2 H), 7.40 (d, 2 H), 7.82 (d, 2 H); ESIMS, m/z for $C_{31}H_{34}ON_4$ [M+H]⁺: 479.

EXAMPLE 92

2-[4-(3-ethoxy-trans-1-propen-1-yl)phenyl]-4,5-bis (4-N-morpholinophenyl) imidazole:

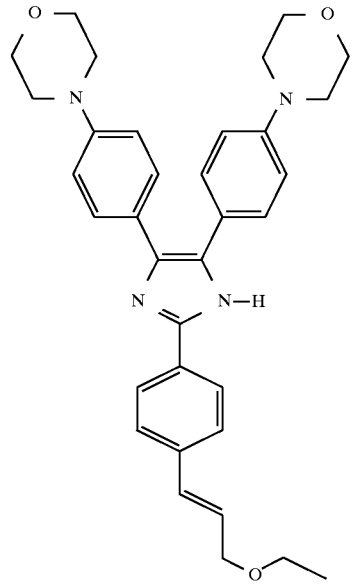

¹H NMR (400 MHz, CD₃OD) δ1.18 (t, 3 H), 3.10 (br s, 8 H), 3.56 (m, 2 H), 3.78 (br s, 8 H), 4.14 (d, 2 H), 6.38 (m, 1 H), 6.88 (d, 4 H), 7.36 (d, 4 H), 7.48 (d, 2 H), 7.88 (d, 2 H); ESIMS, m/z for $C_{34}H_{38}O_3N_4$ [M+H]⁺: 551.

EXAMPLE 93

2-[4-(3-ethoxy-trans-1-propen-1-yl)phenyl]-4-(4-N-dimethylaminophenyl)-5-(4-N-morpholinophenyl) imidazole:

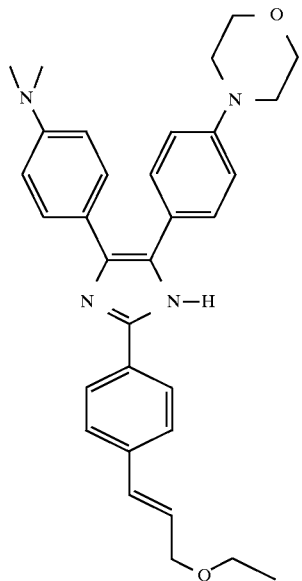

¹H NMR (400 MHz, CD₃OD) δ1.18 (t, 3 H), 2.90 (br s, 6 H), 3.09 (m, 4 H), 3.52 (q, 2 H), 3.76 (m, 4 H), 4.12 (d, 2 H), 6.34 (m, 1 H), 6.62 (d, 1 H), 6.69 (d, 2 H), 6.86 (d, 2 H), 7.27 (d, 2 H), 7.34 (d, 2 H), 7.45 (d, 2 H), 7.87 (d, 2 H); ESIMS, m/z for $C_{32}H_{36}O_2N_4$ [M+H]⁺: 509.

EXAMPLE 94

2-[4-(3-ethoxy-trans-1-propen-1-yl)phenyl]-4-(4-N-methylaminophenyl)-5(4-N-morpholinophenyl) imidazole:

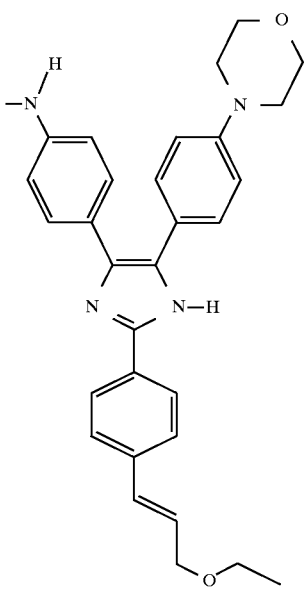

¹H NMR (400 MHz, CD₃OD) δ1.19 (t, 3 H), 2.73 (s, 3 H), 3.08 (m, 4 H), 3.52 (q, 2 H), 3.76 (m, 4 H), 4.10 (d, 2 H), 6.34 (m, 1 H), 6.55 (d, 2 H), 6.61 (d, 1 H), 6.85 (d, 2 H), 7.20 (d, 2 H), 7.34 (d, 2 H), 7.45 (d, 2 H), 7.86 (d, 2 H); ESIMS, m/z for $C_{31}H_{34}O_2N_4$ [M+H]⁺: 495.

EXAMPLE 95

2-[4-(3-ethoxy-trans-1-propen-1-yl)phenyl]-4-(4-N-methylaminophenyl)-5-(4-N-isopropylaminophenyl) imidazole:

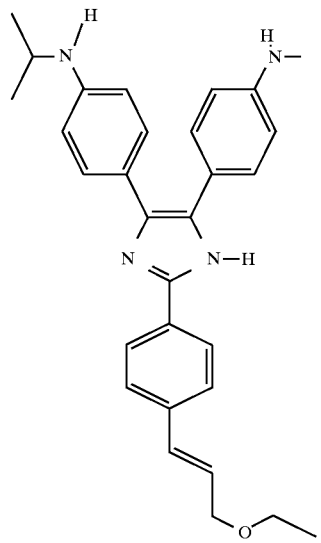

¹H NMR (400 MHz, CD₃OD) δ1.15 (s, 3 H), 1.16 (s, 3 H), 1.18 (t, 3 H), 2.74 (s, 3 H), 3.53 (m, 3 H), 4.10 (d, 2 H), 6.33 (m, 1 H), 6.56 (m, 4 H), 6.60 (d, 1 H), 7.23 (t, 4 H), 7.44 (d, 2 H), 7.85 (d, 2 H); ESIMS, m/z for $C_{30}H_{34}ON_4$ [M+H]⁺: 467.

EXAMPLE 96

2-[4-trans-(2-methanesulfonyl-ethenyl)-phenyl]-4,5-bis (4-N,N-dimethylaminophenyl) imidazole:

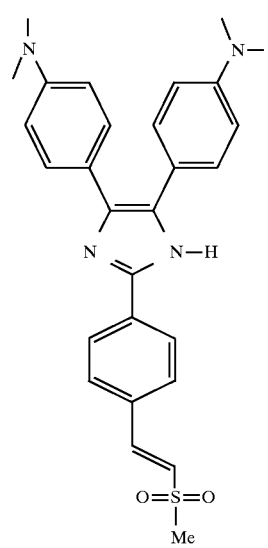

¹H NMR (400 MHz, CD₃OD) δ2.90 (s, 12 H), 3.04 (s, 3 H), 6.70 (d, 4 H), 7.28 (d, 1 H), 7..32 (d, 4 H), 7.58 (d, 1 H), 7.68 (d, 2 H), 8.00 (d, 2 H); ESIMS, m/z for $C_{28}H_{30}O_2N_4S$ [M+H]⁺: 487.

EXAMPLE 97

2-(4-N-morpholinophenyl)-4,5-bis (4-N,N-dimnethylaminophenyl) imidazole:

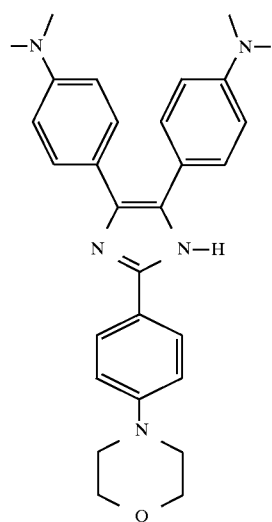

97

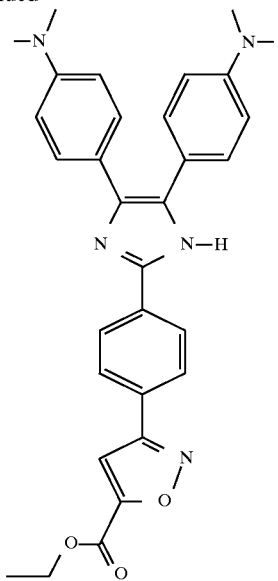

98

¹H NMR (400 MHz, CD₃OD) δ2.85 (br s, 12 H), 3.10 (t, 4 H), 3.74 (t, 4 H), 6.64 (d, 4 H), 6.92 (d, 2 H), 7.26 (d, 4 H), 7.76 (d, 2 H); ESIMS, m/z for $C_{29}H_{33}ON_5$ [M+H]⁺: 468.

EXAMPLE 98

2-[4-(5-ethylcarboxyisoxazol-3-yl)-phenyl]-4,5-bis (4-N,N-dimethylamainophenyl) imidazole:

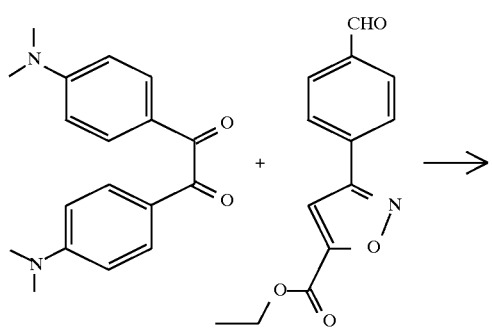

The aldehyde was prepared from terephthaldehyde momo (diethyl acetal) according to a similar literature preparation (Cf. Moriya, O. et al J. Chem. Soc. Perkin Trans 1, 1994, 413.).

Imidazole 98 was prepared according to method C-1. Compound 96 has: ¹H NMR (400 MHz, CD₃OD) δ1.20 (t, 3 H), 2.90 (br s, 12 H), 4.40 (q, 2 H), 6.90 (br s, 4 H), 7.30 (br s, 2 H), 7.58 (s, 1 H), 7.90 (br s, 4 H), 8.30 (br s, 2 H); ESIMS, m/z for $C_{31}H_{31}O_3N_5$ [M+H]⁺: 522.

EXAMPLE 99

2-[4-trans-(2-methoxycarbonyl-ethenyl)phenyl]-4-(p-tolyl)-5-(4-N,N-diethylaminomethylphenyl) imidazole:

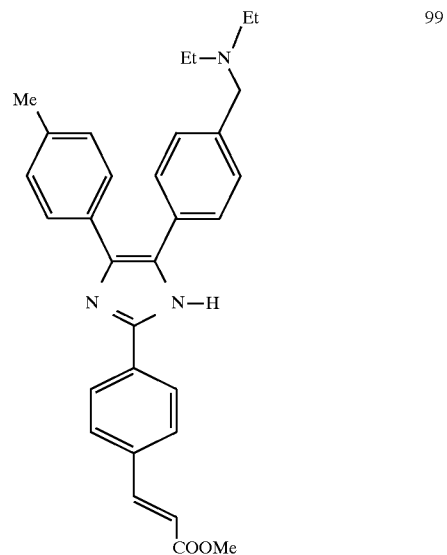

99

¹H NMR (400 MHz, CDCl₃) δ1.01 (t, 6 H), 2.30 (s, 3 H), 2.51 (q, 4 H), 3.54 (s, 2 H), 3.76 (s, 3 H), 6.38 (d, 1 H), 7.04–7.54 (m, 10 H), 7.62 (d, 1 H), 7.92 (d, 2 H); ESIMS, m/z for C₃₁H₃₃O₂N₃ [M+H]⁺: 480.

EXAMPLE 100

2-[4-trans-(2-methoxycarbonyl-ethenyl)phenyl]-4,5-bis (4-N,N-diethylaminomethylphenyl) imidazole:

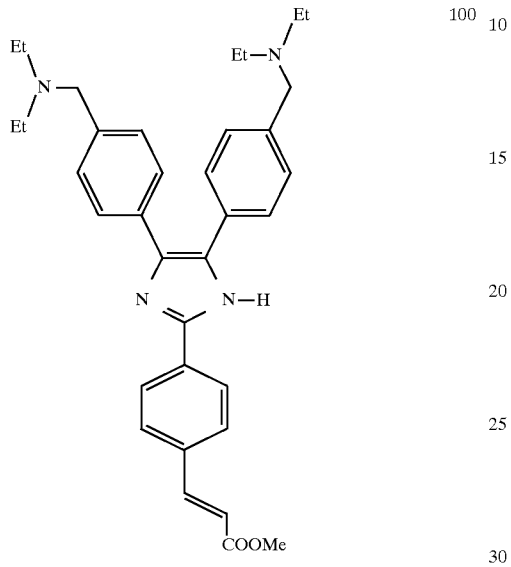

¹H NMR (400 MHz, CDCl₃) δ1.01 (t, 12 H), 2.51 (q, 8 H), 3.54 (s, 4 H), 3.76 (s, 3 H), 6.40 (d, 1 H), 7.20–7.54 (m, 10 H), 7.64 (d, 1 H), 7.92 (d, 2 H); ESIMS, m/z for C₃₅H₄₂O₂N₄ [M+H]⁺: 551.

EXAMPLE 101

2-[4-trans-(2-methoxycarbonyl)cyclopropan-1-yl]-4,5-bis (4-N,N-diethylaminomethylphenyl) imidazole:

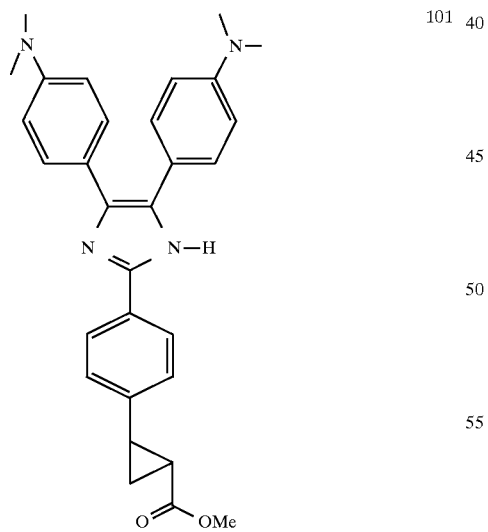

¹H NMR (400 MHz, CD₃OD) δ1.38 (m, 1 H), 1.53 (m, 1 H), 1.92 (m, 1 H), 2.48 (m, 1 H), 2.90 (s, 12 H), 3.68 (s, 3 H), 6.69 (d, 4 H), 7.17 (d, 2 H), 7.28 (d, 4 H), 7.82 (d, 2 H); ESIMS, m/z for C₃₀H₃₂O₂N₄ [M+H]⁺: 481.

EXAMPLE 102

2-[4-(3-ethoxy-trans-1-propen-1-yl)phenyl]-4,5-bis (4-dimethoxyphenyl) imidazole:

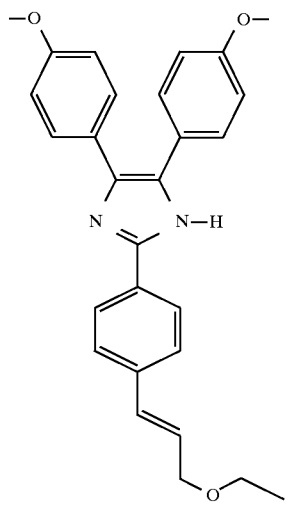

¹H NMR (400 MHz, CD₃OD) δ1.18 (t, 3 H), 3.50 (q, 2 H), 3.72 (s, 6 H), 4.08 (d, 2 H), 6.33 (m, 1 H), 6.58 (d, 1 H), 6.82 (d, 4 H), 7.32 (d, 4 H), 7.42 (d, 2 H), 7.85 (d, 2 H); ESIMS, m/z for C₂₈H₂₈O₃N₂ [M+H]⁺: 441.

EXAMPLE 103

2-[4-(3-ethoxy-trans-1-propen-1-yl)phenyl]-4,5-bis (4-diethoxyphenyl) imidazole:

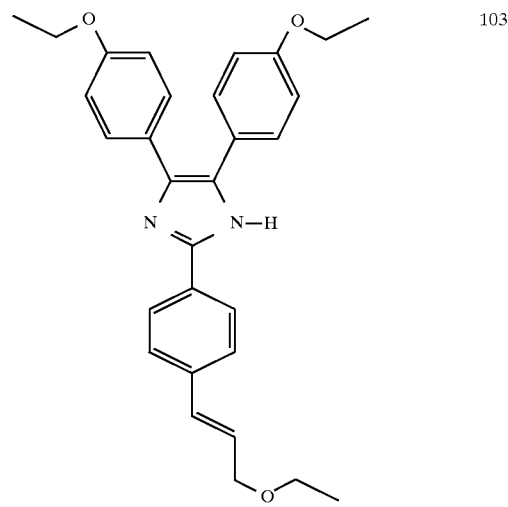

¹H NMR (400 MHz, CD₃SOCD₃) δ1.18 (t, 3 H), 1.32 (t, 6 H), 3.52 (q, 2 H), 3.96 (q, 4 H), 4.10 (d, 2 H), 6.33 (m, 1 H), 6.61 (d, 1 H), 6.81 (d, 4 H), 7.31 (d, 4 H), 7.45 (d, 2 H), 7.86 (d, 2 H); ESIMS, m/z for C₃₀H₃₂O₃N₂ [M+H]⁺: 469.

EXAMPLE 104

2-[4-(3-ethoxy-trans-1-propen-1-yl)phenyl]-4,5-bis (4diisopropyloxyphenyl) imidazole:

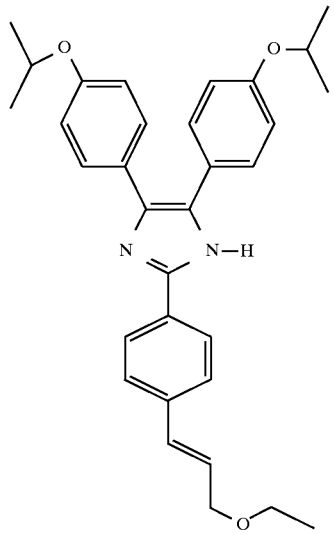

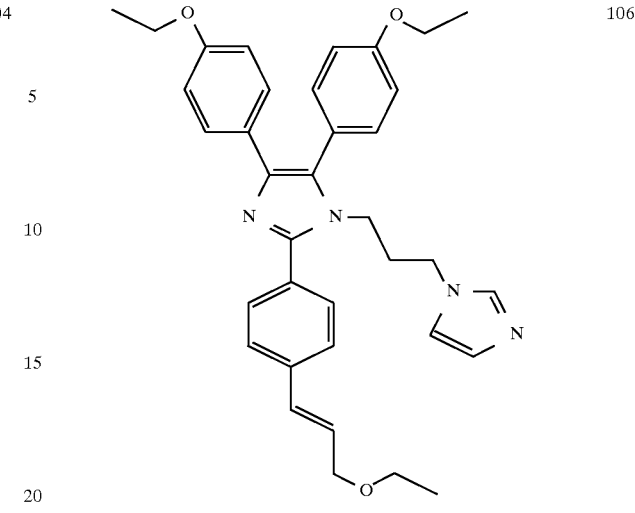

¹H NMR (400 MHz, CD₃OD) δ1.18 (t, 3 H), 1.25 (d, 12 H), 3.51 (q, 2 H), 4.10 (d, 2 H), 4.53 (m, 2 H), 6.32 (m, 1 H), 6.60 (d, 1 H), 6.80 (d, 4 H), 7.31 (d, 4 H), 7.43 (d, 2 H), 7.86 (d, 2 H); ESIMS, m/z for $C_{32}H_{36}O_3N_2$ [M+H]⁺: 497.

EXAMPLE 105

1-(3-imidazole-1-yl-propyl)-2-[4-(3-ethoxy-trans-1-propen-1-yl)phenyl]-4,5bis (4-dimethoxyphenyl) imidazole:

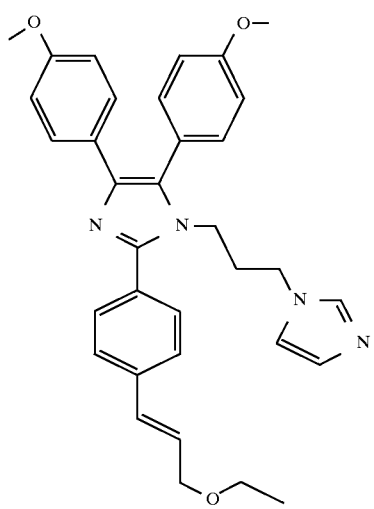

¹H NMR (400 MHz, CD₃OD) δ1.20 (t, 3 H), 1.75 (m, 2 H), 3.55 (q, 2 H), 3.68 (m, 5 H), 3.82 (s, 3 H), 3.88 (t, 2 H), 4.14 (d, 2 H), 6.41 (m, 1 H), 6.70 (m, 5 H), 6.97 (d, 2 H), 7.21 (d, 2 H), 7.28 (d, 2 H), 7.30 (s, 1 H), 7.50 (s, 4 H); ESIMS, m/z for $C_{34}H_{36}O_3N_4$ [M+H]⁺: 549.

EXAMPLE 106

1-(3-imidazole-1-yl-propyl)-2-[4-(3-ethoxy-trans-1-propen-1-yl)phenyl]-4,5bis (4-diethoxyphenyl) imidazole:

¹H NMR (400 MHz, CD₃OD) δ1.20 (t, 3 H), 1.29 (t, 3 H), 1.39 (t, 3 H), 1.74 (m, 2 H), 3.55 (q, 2 H), 3.66 (t, 2 H), 3.86 (t, 2 H), 3.91 (q, 2 H), 4.04 (q, 2 H), 4.14 (d, 2 H), 6.41 (m, 1 H), 6.67 (m, 5 H), 6.94 (d, 2 H), 7.18 (d, 2 H), 7.27 (d, 2 H), 7.31 (s, 1 H), 7.50 (s, 4 H); ESIMS, m/z for $C_{36}H_{40}O_3N_4$ [M+H]⁺: 577.

EXAMPLE 107

1-(3-imidazole-1-yl-propyl)-2-[4-(3-ethoxy-trans-1-propen-1-yl)phenyl]-4,5bis (4-diisopropyloxyphenyl) imidazole:

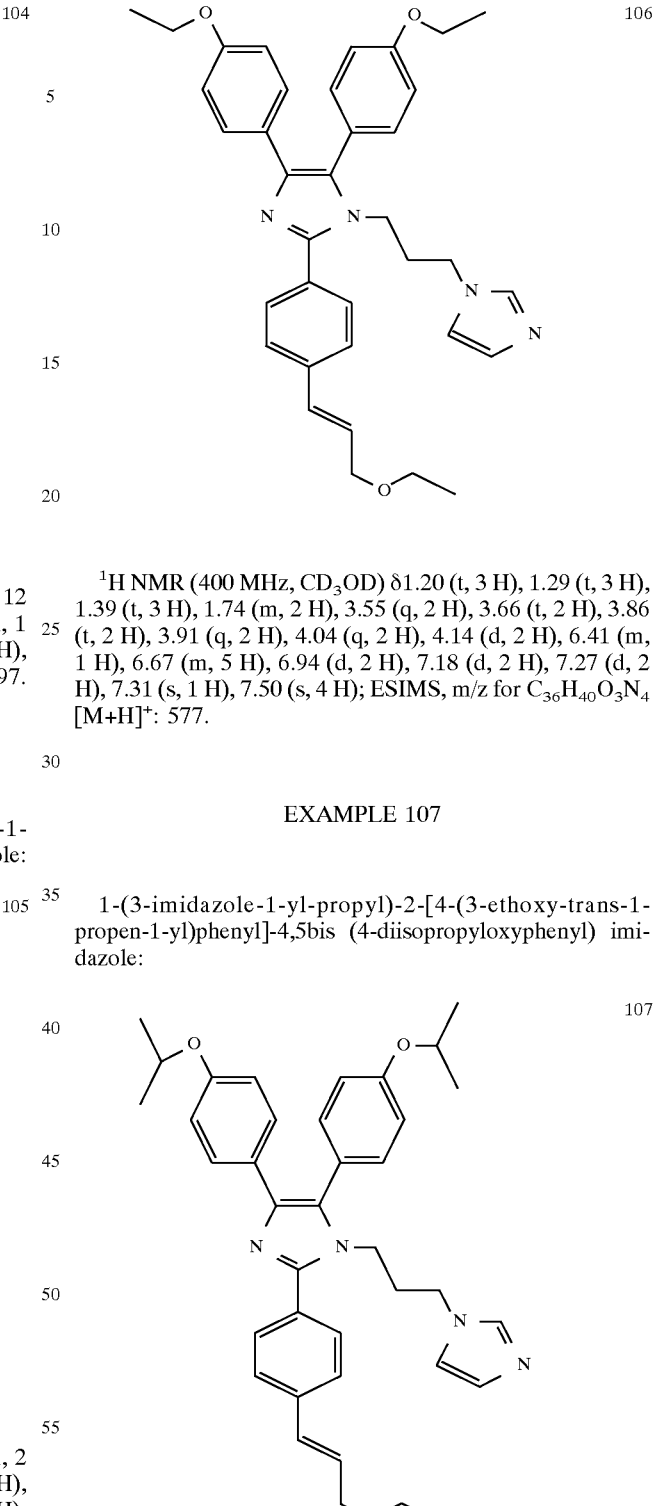

¹H NMR (400 MHz, CD₃OD) δ1.20 (t, 3 H), 1.20 (d, 6 H), 1.30 (d, 6 H), 1.74 (m, 2 H), 3.54 (q, 2 H), 3.65 (t, 2 H), 3.85 (t, 2 H), 4.14 (d, 2 H), 4.47 (m, 1 H), 4.60 (m, 1 H), 6.40 (m, 1 H), 6.67 (m, 5 H), 6.93 (d, 2 H), 7.17 (d, 2 H), 7.28 (d, 2 H), 7.34 (s, 1 H), 7.50 (s, 4 H); ESIMS, m/z for $C_{38}H_{44}O_3N_4$ [M+H]⁺: 605.

Method C-2

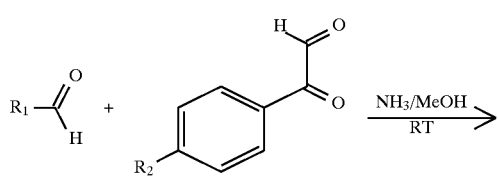

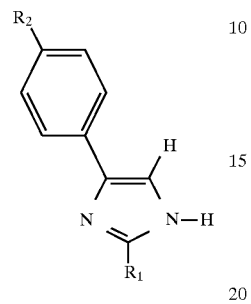

Imidazoles of this type were synthesized in the following way:

The appropriate substituted phenylglyoxal and aldehyde (equal molar amount to the phenylglyoxal)) were stirred in methanolic ammonia at room temperature (TLC mornitored). At completion, the reaction mixture diluted with ethyl acetate and washed with water (×2). The organic layer was then washed with hydrochloric acid (2N) until no more desired compound in the organic layer. The aqueous layer was then neutralized with aqueous NaOH (2N), and extracted with $CH_2CL_2$ (×2). The organic layer was dried ($Na_2SO_4$) and evaporated. Further chromatographic purification then gave the desired compound. The following compounds were synthesized in this way:

EXAMPLE 108

2-[4-(3-ethoxy-trans-1-propen-1-yl)phenyl]-4-(4-N,N-diethylphenyl) imidazole:

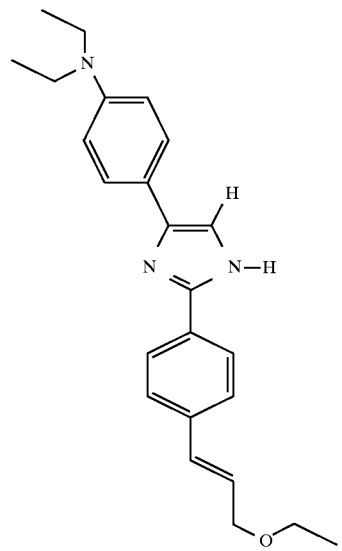

$^1$H NMR (400 MHz, $CD_3OD$) δ1.10 (t, 6 H), 1.17 (t, 3 H), 3.30 (q, 4 H), 3.49 (q, 2 H), 4.08 (d, 2 H), 6.31 (m, 1 H), 6.58 (d, 1 H), 6.68 (d, 2 H), 7.18 (s, 1 H), 7.42 (d, 2 H), 7.50 (d, 2 H), 7.82 (d, 2 H); ESIMS, m/z for $C_{24}H_{29}ON_3$ [M+H]$^+$: 376.

EXAMPLE 109

2-[4-(3-ethoxy-trans-1-propen-1-yl)phenyl]-4-(4-methoxyphenyl) imidazole:

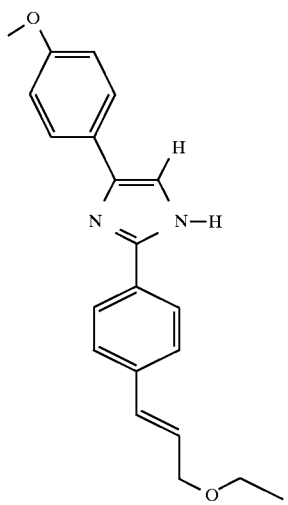

$^1$H NMR (400 MHz, $CD_3OD$) δ1.18 (t, 3 H), 3.51 (q, 2 H), 3.78 (s, 3 H), 4.08 (d, 2 H), 6.32 (m, 1 H), 6.59 (d, 1 H), 6.90 (d, 2 H), 7.29 (s, 1 H), 7.44 (d, 2 H), 7.62 (d, 2 H), 7.82 (d, 2 H); ESIMS, m/z for $C_{21}H_{22}O_2N_2$ [M+H]$^+$: 335.

Method C-3

EXAMPLE 111

2-[4-trans-(2-N,N-dimnethylcarbonyl)-ethenyl]phenyl}-4,5-bis (4-N-dimethylaminophenyl) imidazole:

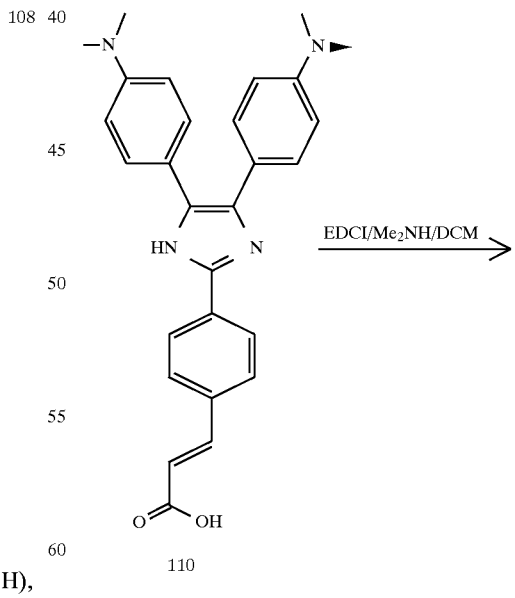

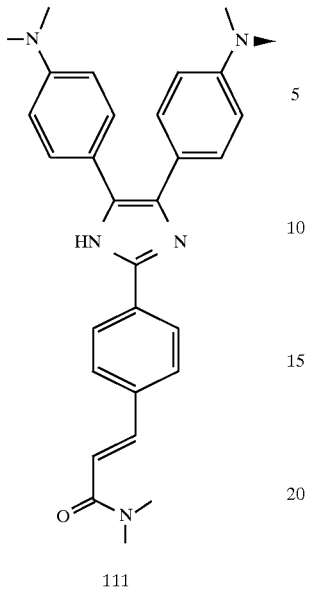

111

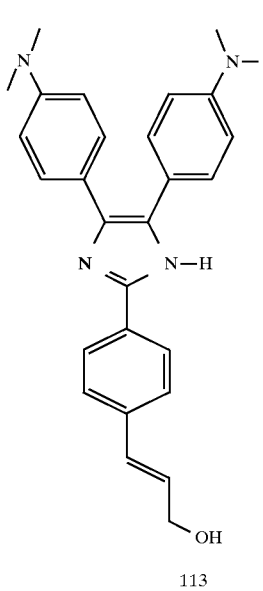

113

To a solution of compound 110 (100 mg, 0.22 mmol) in dichloromethane (5.0 mL) was added dimethylamine hydrochloride (54 mg, 0.66 mmol), EDCI (51 mg, 0.26 mmol), and DMAP (40 mg, 0.33 mmol). After stirring overnight at room temperature (23° C.), the solution was diluted with ethyl acetate and washed with water. The organic layer was dried ($Na_2SO_4$), and evaporated. The residue was purified via preparative TLC to give the desired compound as a yellow solid. Compound 111 has $^1$H NMR (400 MHz, $CD_3OD$) δ2.92 (s, 12 H), 3.03 (s, 3 H), 3.22 (s, 3 H), 6.72 (d, 4 H), 7.16 (d, 1 H), 7.32 (d, 4 H), 7.55 (d, 1 H), 7.75 (d, 2 H), 7.96 (d, 2 H); ESIMS, m/z for $C_{30}H_{33}ON_5$ [M+H]$^+$: 480.

Method C-4

EXAMPLE 113

2-[4-(3-hydroxy-trans-1-propen-1-yl)phenyl]-4,5-bis (4-N,N-dimethylaminophenyl) imidazole:

DIBAL-H (1.0M in DCM, 1.76 ml, 1.76 mmol) was added dropwise to a solution of compound 112 DCM (207 mg, 0.44 mmol) at −78° C. After 1 h at 78° C., aqueous sodium hydroxide (1.0M, 20 mL) was added and the mixture was warmed to 23° C. Layers were separated and the aqueous layer was extracted with DCM (×2). The combined organic layers were dried ($Na_2SO_4$) and evaporated. Purification on preparative TLC gave the desired compound 113 159 mg, as a yellow solid. Compound 113 has: $^1$H NMR (400 MHz, $CD_3OD$) δ2.90 (s, 12 H), 4.20 (d, 2 H), 6.38 (m, 1 H), 6.59 (d, 1 H), 6.67 (d, 4 H), 7.28 (d, 4 H), 7.43 (d, 2 H), 7.85 (d, 2 H); ESIMS, m/z for $C_{28}H_{30}ON_4$ [M+H]$^+$: 439.

Method C-5

EXAMPLE 114

1-methyl-2-[4-(3-hydroxy-trans-1-propen-1-yl)phenyl]-4,5-bis (4-N,N-dimethylaminophenyl) imidazole:

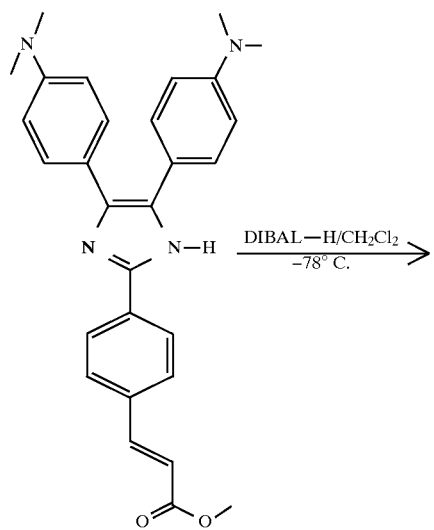

112

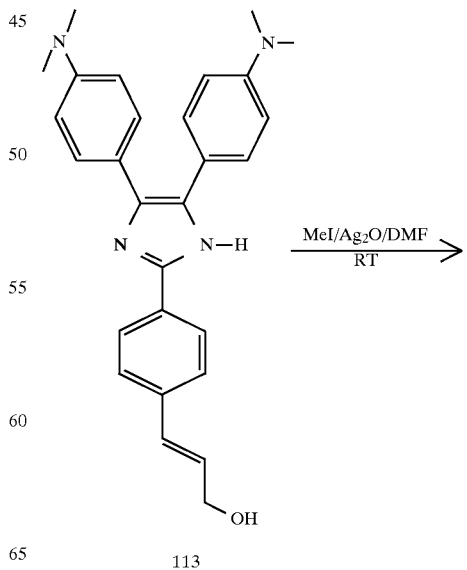

113

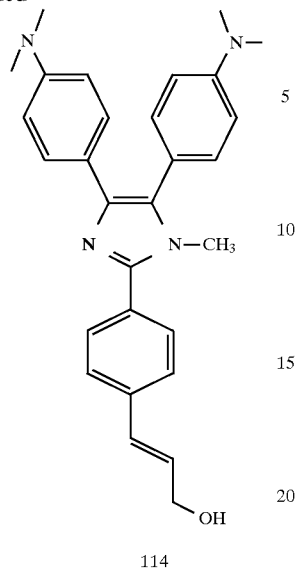

114

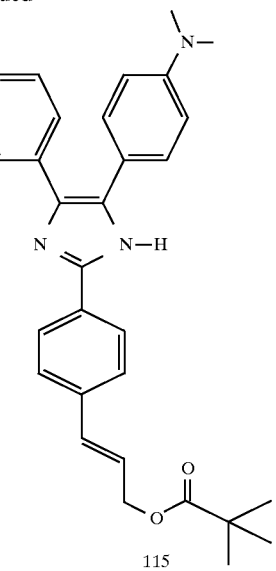

115

A suspention of compound 113 (11 mg, 0.026 mmol), methyliodide (31 mL, 0.031 mmol), silver oxide (excess) in DMF was stirred at 23° C. overnight. The mixture was then diluted with DCM and washed with water. ). The organic layer was dried ($Na_2SO_4$) and evaporated. Purification on preparative TLC gave the desired compound, 4.0 mg, as a yellow solid. Compound 114 has: $^1$H NMR (400 MHz, $CD_3OD$) δ2.84 (s, 6 H), 2.96 (s, 6 H), 3.45 (s, 3 H), 4.23 (d, 2 H), 6.45 (m, 1 H), 6.63 (d, 2 H), 6.66 (d, 1 H), 6.80 (d, 2 H), 7.15 (d, 2 H), 7.27 (d, 2 H), 7.53 (d, 2 H), 7.63 (d, 2 H); ESIMS, m/z for $C_{29}H_{32}ON_4$ [M+H]$^+$: 453.

Method C-6

EXAMPLE 115

2-[4-(3-pivalate-trans-1-propen-1-yl)phenyl]-4,5-bis (4-N,N-dimethylaminophenyl) imidazole:

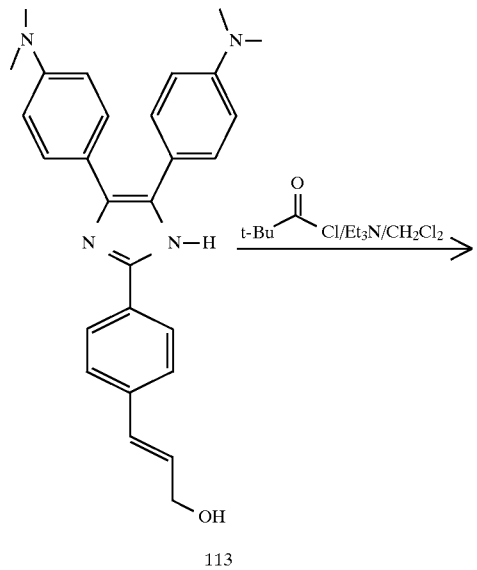

113

Compound 114 was prepared via acylation of allylic alcohol 113 A mixture of pivaloyl chloride (0.1M) and triethylamine (0.15M) (0.55 mL) was added to a solution of allylic alcohol 113 (20 mg, 0.045 mmol) in DCM. at −20° C. The resulting mixture was stirred for 30 min, diluted with DCM, washed with water. The organic layer was dried ($Na_2SO_4$) and evaporated. Purification on preparative TLC gave the desired compound 115 5 mg, as a yellow solid. Compound 115 has: $^1$H NMR (400 MHz, $CD_3OD$) δ1.10 (s, 9 H), 2.90 (s, 12 H), 4.70 (d, 2 H), 6.34 (m, 1 H), 6.65 (d, 1 H), 6.67 (d, 4 H), 7.30 (d, 4 H), 7.48 (d, 2 H), 7.85 (d, 2 H); ESIMS, m/z for $C_{33}H_{38}O_2N_4$ [M+H]$^+$: 523.

Method C-7

EXAMPLE 116

2-[4- (3-methylcarbonyl-trans-1-propen-1-yl)phenyl]-4, 5-bis (4-N,N-dimethylaminophenyl) imidazole:

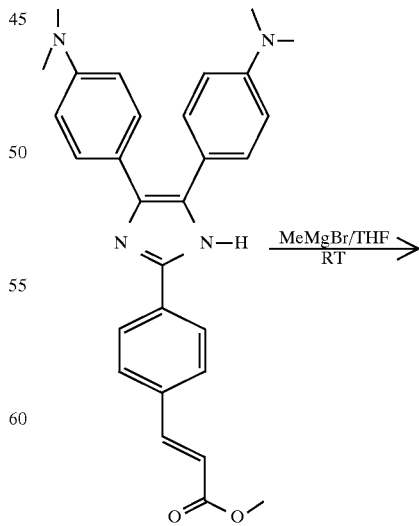

112

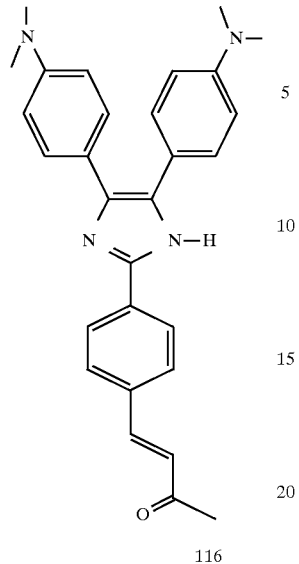

116

Methylmagnesium bromide (1.0M, in dibutylether, 0.63 mL, 0.65 mmol) was added to solution of compound 112 in THF (5.0 mL) at −78 °C. After stirring overnight under argon, during which time the mixture was warmed to 23° C., it was diluted with water and extracted with DCM. The combined organic layers were dried ($Na_2SO4$) and evaporated. Purification on preparative TLC gave the desired compound as a yellow solid. Compound 116 has: $^1$H NMR (400 MHz, $CD_3OD$) δ2.36 (s, 3 H), 2.92 (s, 12 H), 6.71 (d, 4 H), 6.80 (d, 1 H), 7.31 (d, 4 H), 7.64 (d, 1 H), 7.70 (d, 2 H), 7.98 (d, 2 H); ESIMS, m/z for $C_{29}H_{30}ON_4$ $[M+H]^+$: 451.

Method C-8

EXAMPLE 118

2-[4-(3-methylcarbonyl-trans-1-propen-1-yl)phenyl]-5-methoxy benzimidazole:

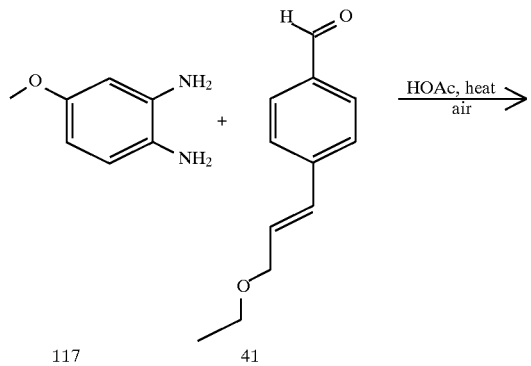

117    41

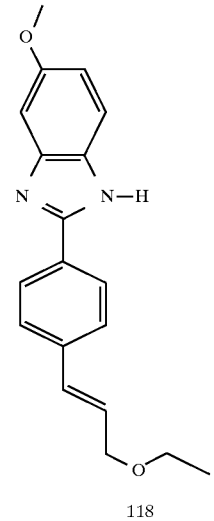

118 compound 118 was prepared according to a known procedure (Lee, M. et al *Med. Chem.Res.* 1993, 2, 79–86). Compound 118 has: $^1$H NMR (400 MHz, $CD_3OD$) δ1.20 (t, 3 H), 3.54 (q, 2 H), 3.81 (s, 3 H), 4.13 (d, 2 H), 6.41 (m, 1 H), 6.66 (d, 1 H), 6.86 (m, 1 H), 7.04 (d, 1 H), 7.44 (d, 1 H), 7.53 (d, 2 H), 7.96 (d, 2 H); ESIMS, m/z for $C_{19}H_{20}O_2N_2$ $[M+H]^+$: 309.

EXAMPLE 119

2-[4-(3-ethoxy-trans-1-propen-1-yl)phenyl]-4,5-bis-(4-N-isopropylaminophenyl) imidazole, Compound 119 was prepared according to method C-1 by using the appropriate starting materials.

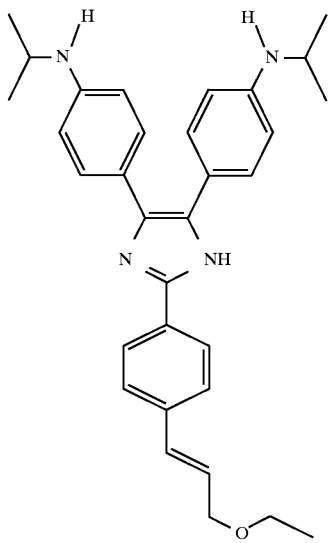

$^1$H NMR (400 MHz, $CD_3OD$) δ1.15 (d, 6 H), 1.16 (d, 6 H), 1.18 (t, 3 H), 3.53 (m, 4 H), 4.10 (br s, 2 H), 6.33 (br s, 1 H), 6.56 (m, 5 H), 7.23 (d, 4 H), 7.44 (d, 2 H), 7.85 (d, 2 H); ESIMS, m/z for $C_{32}H_{38}ON_4$ $[M+H]^+$: 495.

EXAMPLE 120

2-[4-(3-ethoxy-trans-1-propen-1-yl)phenyl]-4-(4-N-ethylaminophenyl)-5(4-N-isopropylaminophenyl) imidazole, Compound 120 was prepared according to method C-1 by using the appropiate starting materials.

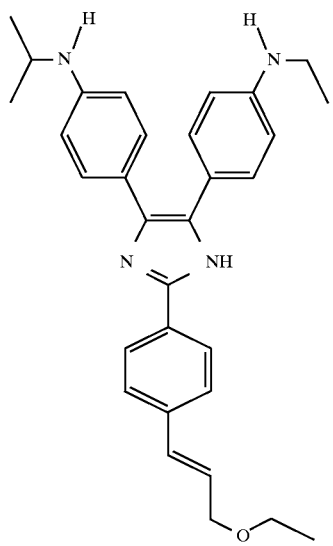

¹H NMR (400 MHz, CD₃OD) δ1.16 (m, 12 H), 3.07 (q, 2 H), 3.53 (m, 3 H), 4.10 (d, 2 H), 6.33 (m, 1 H), 6.56 (m, 5 H), 7.23 (d, 4 H), 7.44 (d, 2 H), 7.85 (d, 2 H); ESIMS, m/z for $C_{31}H_{36}ON_4$ [M+H]⁺: 481.

EXAMPLE 121

2-[4-(3-ethoxy-trans-1-propen-1-yl)phenyl]-4-(4-fluorophenyl)-5-(4-N-isopropylaminophenyl) imidazole, Compound 121 was prepared according to method C-1 by using the appropriate starting materials.

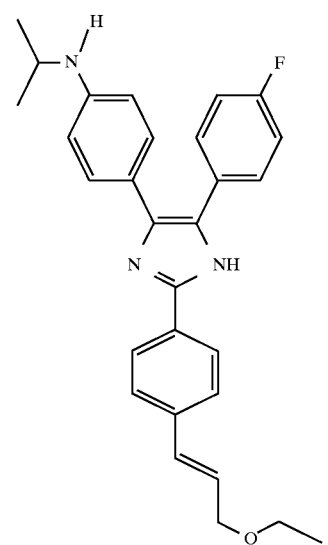

¹H NMR (400 MHz, CD₃OD) δ1.16 (m, 9 H)), 3.52 (m, 3 H), 4.09 (d, 2 H), 6.32 (m, 1 H), 6.56 (d, 2 H), 6.58 (d, 1 H), 6.98 (dd, 2 H), 7.14 (d, 2 H), 7.45 (m, 4 H), 7.85 (d, 2 H); ESIMS, m/z for $C_{29}H_{30}FON_3$ [M+H]⁺: 456.

EXAMPLE 122

2-[4-(3-ethoxy-trans-1-propen-1-yl)phenyl]-4-(4-N,N-dipropylphenyl) imidazole,

Compound 122 was prepared according to method C-2 by using the appropriate starting materials.

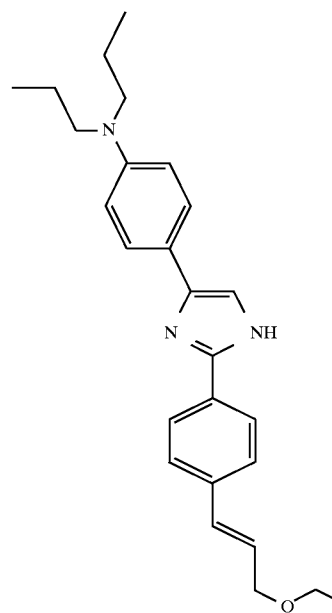

¹H NMR (400 MHz, CD₃OD) δ0.91 (t, 6 H), 1.19 (t, 3 H), 1.58 (m, 4 H), 3.26 (m, 4 H), 3.53 (m, 2 H), 4.11 (d, 2 H), 6.35 (m, 1 H), 6.63 (d, 1 H), 6.66 (d, 1 H), 7.19 (s, 1 H), 7.48 (m, 4 H), 7.83 (d, 2 H); ESIMS, m/z for $C_{26}H_{33}ON_3$ [M+H]⁺: 404.

EXAMPLE 123

2-[4-(3-ethoxy-trans-1-propen-1-yl)phenyl]-4-(4-N-isopropylphenyl) imidazole,

Compound 123 was prepared according to method C-2 by using the appropriate starting materials.

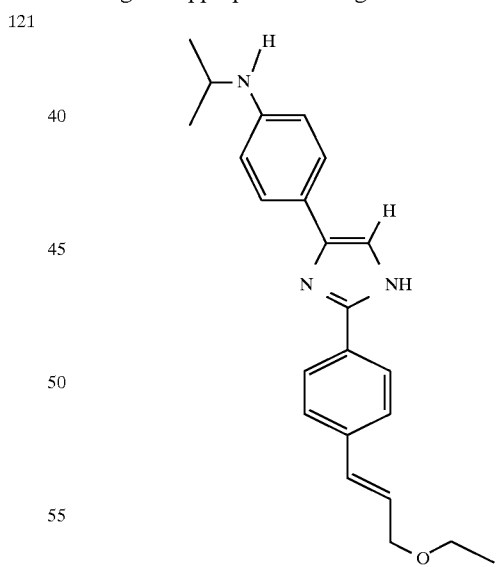

¹H NMR (400 MHz, CD₃OD) δ1.16 (d, 6 H), 1.19 (t, 3 H), 3.53 (q, 2 H), 3.60 (m, 1 H), 4.11 (d, 2 H), 6.35 (m, 1 H), 6.62 (d, 1 H), 6.64 (d, 2 H), 7.19 (s, 1 H), 7.46 (m, 4 H), 7.83 (d, 2 H); ESIMS, m/z for $C_{23}H_{27}ON_3$ [M+H]⁺: 362.

EXAMPLE 124

2-[4-(3-ethoxy-trans-1-propen-1-yl)phenyl]-4- (4-N-isobutylphenyl) imidazole,

Compound 124 was prepared according to method C-2 by using the appropriate starting materials.

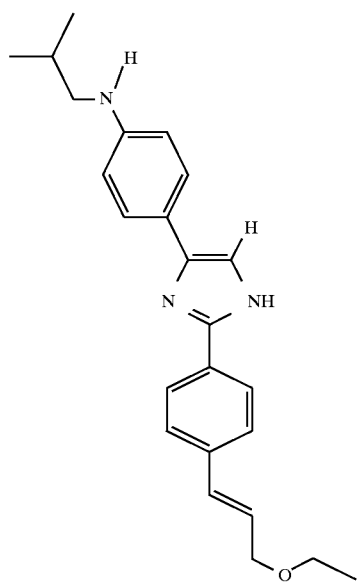

¹H NMR (400 MHz, CD₃OD) δ0.94 (d, 6 H), 1.19 (t, 3 H), 1.87 (m, 1 H), 2.90 (d, 2 H), 3.53 (q, 2 H), 4.12 (d, 2 H), 6.35 (m, 1 H), 6.62 (m, 3 H), 7.18 (s, 1 H), 7.46 (m, 4 H), 7.83 (d, 2 H); ESIMS, m/z for $C_{24}H_{29}ON_3$ [M+H]⁺: 376.

EXAMPLE 125

2-[4-(3-ethoxy-trans-1-propen-1-yl)phenyl]-4-(4-N-morpholinophenyl) imidazole,

Compound 125 was prepared according to method C-2 by using the appropriate starting materials.

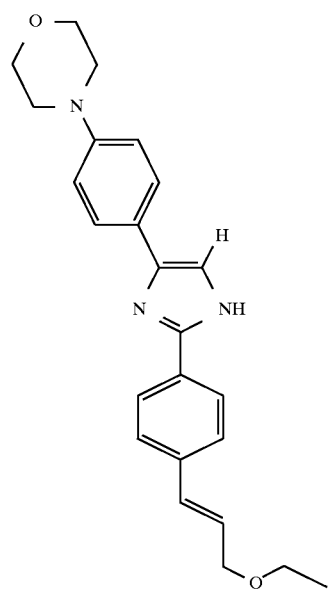

¹H NMR (400 MHz, CD₃OD) δ1.19 (t, 3 H), 3.13 (t, 4 H), 3.53 (q, 2 H), 3.80 (t, 4 H), 4.12 (d, 2 H), 6.35 (m, 1 H), 6.63 (d, 1 H), 6.97 (d, 2 H), 7.29 (s, 1 H), 7.47 (d, 2 H), 7.61 (d, 2 H), 7.84 (d, 2 H); ESIMS, m/z for $C_{24}H_{27}O_2N_3$ [M+H]⁺: 390.

EXAMPLE 126

2-[4-(3-ethoxy-trans-1-propen-1-yl)phenyl]-4-[4-N-(N'-ethyl)piperizanophenyl] imidazole, Compound 126 was prepared according to method C-2 by using the appropriate starting material

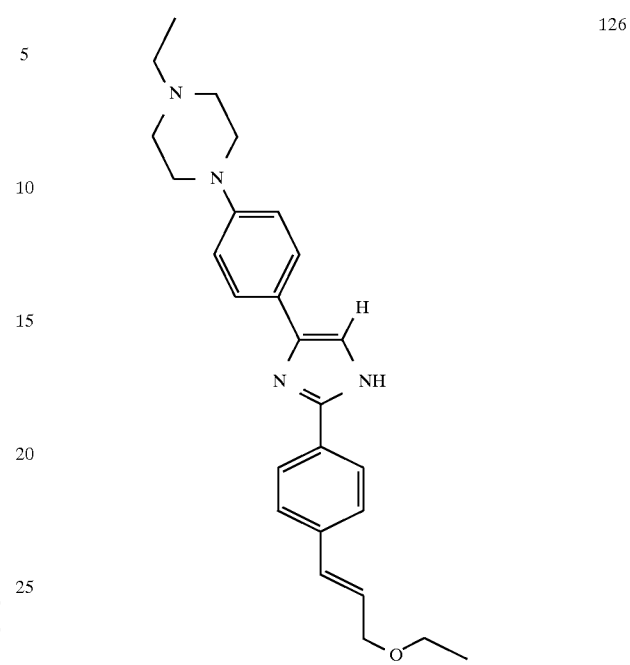

¹H NMR (400 MHz, CD₃OD) δ1.16 (m, 6 H), 2.61 (q, 2 H), 2.78 (t, 4 H), 3.26 (t, 4 H), 3.54 (q, 2 H), 4.12 (d, 2 H), 6.36 (m, 1 H), 6.64 (d, 1 H), 7.00 (d, 2 H), 7.30 (s, 1 H), 7.48 (d, 2 H), 7.62 (d, 2 H), 7.84 (d, 2 H); ESIMS, m/z for $C_{26}H_{32}ON_4$ [M+H]⁺: 417.

EXAMPLE 127

2-[4-(3-ethoxy-trans-1-propen-1-yl)phenyl]-4-(4-N-morpholinophenyl)-5methyl-imidazole.

Compound 127 was prepared according to method C-1 by using the appropriate starting material

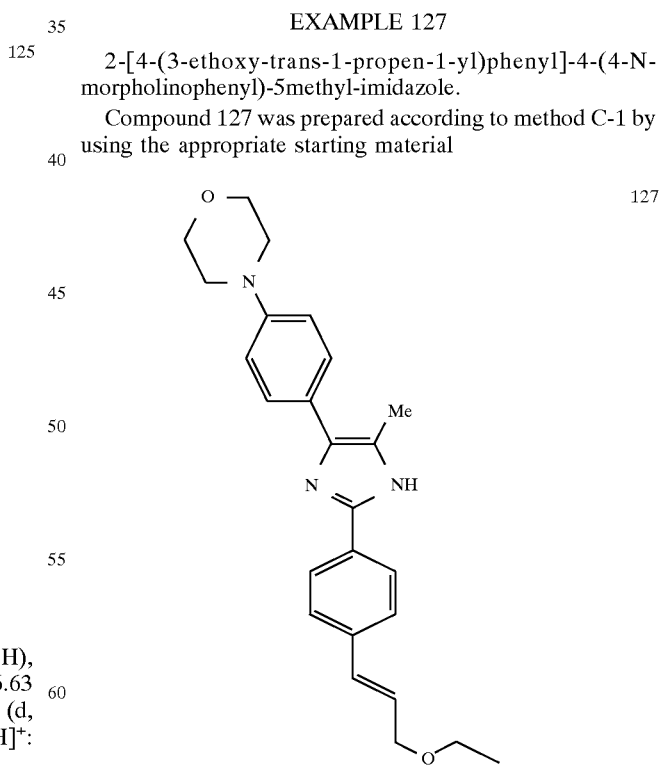

¹H NMR (400 MHz, CD₃OD) δ1.19 (t, 3 H), 2.34 (s, 3 H), 3.11 (t, 4 H), 3.52 (q, 2 H), 3.79 (t, 4 H), 4.10 (d, 2 H), 6.34 (m, 1 H), 6.60 (d, 1H), 6.98 (d, 2 H), 7.44 (m, 4 H), 7.80 (d, 2 H); ESIMS, m/z for $C_{25}H_{29}O_2N_3$ [M+H]⁺: 404.

The compounds described herein are capable of sensitizing multi-drug resistant tumor cells to antitumor chemotherapeutic agents, such as doxorubicin and vinblastine. They also have the ability to potentiate the sensitivity of tumor cells susceptible to these chemotherapeutic agents. This invention also relates to a method of sensitizing multidrug-resistant tumor cells to antitumor chemotherapeutic agents. It also relates to a method of increasing the sensitivity of drug-susceptible tumor cells to antitumor chemotherapeutic agents. In addition, this invention relates to a method of preventing the emergence of MDR tumor cells during a course of treatment with antitumor chemotherapeutic agents. Finally, this invention relates to a method of reducing the effective dosage of an antitumor chemotherapeutic agent during a course of treatment. It has been found that compounds of Formula 1 have the ability to increase the sensitivity of MDR mammalian cells in culture.

Cytotoxic drugs are commonly used as antitumor chemotherapeutic agents. These agents are also called antiproliferative agents. The desired effect of cytotoxic drugs is selective cell death with destruction of the malignant neoplastic cells and relative sparing of normal cells.

Cytotoxic drugs have also proved valuable in the treatment of other neoplastic disorders including connective or autoimmune diseases, metabolic disorders, dermatological diseases, and DNA virus infections.

Proper use of cytotoxic drugs requires a thorough familiarity with the natural history and pathophysiology of the disease before selecting the cytotoxic agent, determining a dose, and undertaling therapy. Each patient must be carefully evaluated, with attention directed toward factors which may potentiate toxicity, such as overt or occult infections, bleeding dyscrasias, poor nutritional status, and severe metabolic disturbances. In addition, the functional condition of certain major organs, such as liver, kidneys, and bone marrow, is extremely important. Therefore, the selection of the appropriate cytotoxic agent and devising an effective therapeutic regimen is influenced by the presentation of the patient.

Cytotoxic drugs as antitumor chemotherapeutic agents can be subdivided into several broad categories, including, (1) alkylating agents, such as mechlorethamine, cyclophosphamide, melphalan, uracil mustard, chlorambucil, busulfan, carmustine, lomustine, semustine, streptozoticin, and decrabazine; (2) antimetabolites, such as methotrexate, fluorouracil, fluorodeoxyuridine, cytarabine, azarabine, idoxuridine, mercaptopurine, azathioprine, thioguanine, and adenine arabinoside; (3) natural product derivatives, such as vinblastine, vincristine, dactinomycin, daunorubicin, doxorubicin, mithramycin, bleomycin, etoposide, teniposide, and mitomycin-C; and (4) miscellaneous agents, such as hydroxyurea, procarbezine, mititane, and cis-platinum.

Important antitumor chemotherapeutic agents (with the usual effective dosage) to which clinical multidrug-resistance has been observed include vinblastine (0.1 mg per kilogram per week), vincristine (0.01 mg per kilogram per week), etoposide (35 to 50 mg per square meter per day), dactinomycin (0.15 mg per kilogram per day), doxorubicin (500 to 600 mg per square meter per week), daunorubicin (65 to 75 mg per square meter per week), and mithramycin (0.025 mg per kilogram per day). MDR has been shown to occur in vitro as well as in the clinic.

Multidrug-resistant cell lines are easily obtainable for in vitro determination of drug sensitization by compounds of the present invention. In vitro potentiation of antineoplastic cytotoxicity by the imidazole derivatives of the present invention was measured in both CEM/VLB1000 and SK/VLB1000 cell lines. The multidrug resistant cell lines were obtained from Dr. Victor Ling, Ontario Cancer Institute, Toronto, Canada. The CEM/VLB 1000 cell line was maintained as a suspension in minimum essential medium supplemented with 10% fetal bovine serum in a humidied atmosphere of 95% air and 5% $CO_2$ while the SK/VLB 1000 cell line was maintained as adherent cells using the identical medium conditions as the CEM cells. The CEM/VLB 1000 cells were seeded at a density of $5 \times 10^4$ cells/well in a 96 well microtiter plate while the SK/VLB 1000 cell line was seeded at a density of 2,500 cells/well after trypsinization. Vinblastine (5 µg/mL, for the CEM cells) or Taxol (3 µg/mL, for the SK cells) and compound (0.01 to 50 µM) were added directly to the wells. After an incubation of 48 hours in presence of drug, alamar blue (B. Page et al., *Int. J. OncoL* 3: 473–476, 1993) was added (10 µL to the 200 µL cell suspension) for a period of 24 hours after which the fluorescence (excitation=530 nM, emission= 590 nM) was read for each well using a "CytoFluor" microtiter fluorometer plate reader. This assay measures the effective concentration of compound necessary to enhance the cytotoxicity ($EC_{50}$) of vinblastine in the MDR cell line. The compounds of the present invention had $EC_{50}$ values in the range of 0.06 to 10 µM.

$^3$H-vinblastine accumulation was also measured in the CEM/VLB1000 cell line. Corning Easy-Wash 96 well plates were pretreated with PBS and 1% BSA for 60 minutes and then removed. CEM/VLB1000 cells were seeded at $2 \times 10^5$, 40 µL volume. Plates were incubated at 37° C. for 30–60 minutes prior to use. The reference reversing agent, verapamil, or the compound of the present invention was added to the well followed by addition of media containing $^3$H-vinblastine (final concentration=275 nM). Plates were allowed to incubate for 3 hours at 37° C. Cells were harvested onto pretreated Wallace filtermats A (pretreated with 0.1% polyethyleneimine) using a TomTek harvester-96. After filtering, the filtermats were allowed to dry completely. Meltix B scintillant was then added to the filtermats. The filters were then placed in a 90° C. oven for approximately 3–5 minutes and then removed. Scintillant was allowed to solidify on the filtermats. Filtermats were then placed in sample bags and read on a Wallace BetaPlate scintillation counter. The effects of compounds of the present invention in the cytotoxicity potentiation assays and vinblastine (VLB) accumulation assay are given in the Table below:

| Examples | Cytotocicity Potentiation (µM)[1] CEM/VLB1000 | [$^3$H]VLB Accumulation (µM)[2] CEMVLB1000 |
|---|---|---|
| 56 | 0.55 | 'NT[3] |
| 57 | 0.21 | NT |
| 58 | 0.47 | NT |
| 59 | 0.55 | NT |
| 60 | 0.45 | NT |
| 61 | 0.16 | NT |
| 62 | 1.03 | NT |
| 63 | 0.32 | NT |
| 64 | 0.55 | NT |
| 65 | 0.25 | NT |
| 66 | 0.85 | NT |
| 67 | 0.098 | NT |
| 68 | 0.39 | NT |
| 69 | 0.33 | NT |
| 70 | 0.50 | NT |
| 71 | 0.37 | NT |
| 72 | 0.32 | NT |

-continued

| Examples | Cytotocicity Potentiation ($\mu M$)[1] CEM/VLB1000 | [$^3$H]VLB Accumulation ($\mu M$)[2] CEMVLB1000 |
|---|---|---|
| 73 | 0.34 | NT |
| 74 | 0.13 | 2.0 |
| 75 | 0.098 | 1.2 |
| 76 | 0.11 | NT |
| 77 | 0.34 | 1.2 |
| 78 | 0.45 | NT |
| 79 | 1.21 | NT |
| 80 | 0.88 | NT |
| 81 | 0.32 | NT |
| 82 | 0.96 | NT |
| 83 | 1.30 | NT |
| 84 | 0.09 | NT |
| 85 | 0.11 | NT |
| 86 | 0.26 | NT |
| 87 | 0.06 | NT |
| 88 | 0.26 | NT |
| 89 | 0.24 | NT |
| 90 | 0.12 | NT |
| 91 | 0.11 | NT |
| 92 | 0.22 | NT |
| 93 | 0.15 | NT |
| 94 | 0.25 | NT |
| 95 | 0.05 | NT |
| 96 | 0.73 | NT |
| 97 | 0.19 | NT |
| 98 | 0.60 | NT |
| 99 | 0.29 | NT |
| 100 | 3.4 | NT |
| 101 | 0.2 | NT |
| 102 | 0.35 | NT |
| 103 | 0.24 | NT |
| 104 | 0.25 | NT |
| 105 | 0.65 | NT |
| 106 | 0.38 | NT |
| 107 | 0.49 | NT |
| 108 | 0.30 | NT |
| 109 | 1.85 | NT |
| 111 | 0.62 | 1.7 |
| 113 | 0.41 | 3.9 |
| 114 | 0.63 | NT |
| 115 | 0.48 | NT |
| 116 | 0.23 | NT |
| 118 | 1.00 | NT |
| 119 | .067 | NT |
| 120 | .053 | NT |
| 121 | .12 | NT |
| 122 | .28 | NT |
| 123 | .34 | NT |
| 124 | .25 | NT |
| 125 | .37 | NT |
| 126 | .71 | NT |
| 127 | .33 | NT |

[1] Values presented are the midpoint (EC$_{50}$) of the minimum and maximum cytotoxicity induced by 3–5 $\mu$g/mL vinblastine and the specific compound of the present invention.
[2] Values presented are the midpoint (EC$_{50}$) of the minimum and maximum increase in accumulation of $^3$H-vinblastine caused by the specfic compound of the present invention.
[3] NT = Not tested.

The modulation of multidrug-resistance demonstrated by the imidazole derivatives described herein provides a method of treatment of multidrug-resistant tumors. The multidrug-resistance modulatory properties of the compounds described herein also provides a method for the prevention of the emergence of multi-drug resistant tumors during the course of cancer treatment. These same compounds additionally provide a method for reducing the required dosage of an antitumor chemotherapeutic agent.

All of the methods of this invention involve (1) the administration of a compound of Formula 1 prior to, together with, or subsequent to the administration of an antitumor chemotherapeutic agent; and (2) the administration of a combination of a compound of Formula 1 and an antitumor chemotherapeutic agent.

Thus, the compounds of Formula 1 are useful in the treatment of multidrug-resistant tumor cells or tumor cells in general, either separately or in combination with an antitumor chemotherapeutic agent. These compounds may be administered orally, topically or parenterally in dosage unit formulations containing conventional non-toxic pharmaceutically acceptable carriers, adjuvants, and vehicles. The term parenteral as used herein includes subcutaneous injections, intravenous, intramuscular, intrasternal injection or infusion techniques.

The present invention also has the objective of providing suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. The tablets contain the acting ingredient in admixture with non-toxic pharmaceutically acceptable excipients which are suitable for the manufacture of tablets. These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such expicients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In adition, fatty acids such as oleic acid find use in the preparation of injectables.

A compound of Formula 1 may also be administered in the form of suppositories for rectal administration of the drug. These compositions can be prepared by mixing the drug with a suitable non-irritating excipient which is solid at ordinary temperature but liquid at the rectal temperature and will therefore melt in the rectum to release the drug. Such materials are cocoa butter and polyethylene glycols.

The compounds of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

For topical use, creams, ointments, jellies, solutions or suspensions, etc., containing the compounds of Formula 1 are employed.

Dosage levels of the compounds of the present invention are of the order of about 0.5 mg to about 100 mg per kilogram body weight, with a preferred dosage range between about 20 mg to about 50 mg per kilogram body weight per day (from about 25 mg to about 5 gms per patient per day). The amount of active ingredient that may be combined with the carrier materials to produce a single dosage will vary depending upon the host treated and the particular mode of administration. For example, a formulation intended for oral administration to humans may contain 5 mg to 1 g of an active compound with an appropriate and convenient amount of carrier material which may vary from about 5 to about 95 percent of the total composition. Dosage unit forms will generally contain between from about 5 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

In addition, some of the compounds of the instant invention may form solvates with water or common organic solvents. Such solvates are encompassed within the scope of the invention.

What is claimed is:

1. A compound of the formula 1

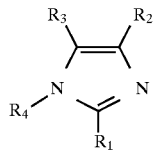

Formula 1 wherein the substituents $R_1$, $R_2$, $R_3$, and $R_4$ are defined as described in A and B below:

A. when $R_1$ is selected from the group consisting of:
  (i) substituted $C_{1-11}$ alkyl or substituted $C_{2-11}$ alkenyl, wherein the substituents are selected from the group consisting of hydroxy, $C_{1-6}$ alkyloxy; or
  (ii) mono-, di-,and tri-substituted aryl-$C_{0-11}$ alkyl wherein aryl is selected from the group consisting of phenyl, furyl, thienyl wherein the substituents are selected from the group consisting of:
    (a) phenyl, trans -2-phenylethenyl, 2-phenylethynyl, 2-phenylethyl, or in which the said phenyl group is mono- or disubstituted with a member selected from the group consisting of hydroxy, halo, $C_{0-4}$ alkyl and $C_{1-4}$ alkyloxy,
    (b) substituted $C_{1-6}$ alkyl, substituted $C_{2-6}$ alkyloxy, substituted $C_{2-6}$ alkylthio, substituted $C_{2-6}$ alkoxycarbonyl, wherein the substituents are selected from the group consisting of $C_{1-6}$ alkoxy, $C_{1-6}$ alkylthio, or
    (c) $C_{1-11}$ $CO_2R_5$, $C_{1-11}$ $CONHR_5$, trans-CH=CHCO$_2$R$_5$, or trans-CH=CHCONH$_5$ wherein $R_5$ is $C_{1-11}$ alkyl, or phenyl $C_{1-11}$ alkyl, $C_{1-6}$ alkoxy-carbonylmethyleneoxy;
then $R_2$ and $R_3$ are each independently selected from the group consisting of mono-, di, and tri-substituted phenyl wherein the substituents are independently selected from:
  (i) substituted $C_{1-6}$ alkyl,
  (ii) substituted $C_{1-6}$ alkyloxy, $C_{3-6}$ alkenyloxy, substituted $C_{3-6}$ alkenyloxy,
  (iii) substituted $C_{1-6}$ alkyl-amino, di(substituted $C_{1-6}$ alkyl)amino,
  (iv) $C_{3-6}$ alkenyl-amino, di($C_{3-6}$ alkenyl)amino, substituted $C_{3-6}$ alkenyl-amino, di(substituted $C_{3-6}$ alkenyl)amino,
  (v) pyrrolidino, piperidino, morpholino, imidazolyl, substituted imidazolyl, piperazino, N—$C_{1-6}$ alkenylpiperazino, N—$C_{3-6}$ alkenylpiperazino, N—($C_{1-6}$ alkoxy $C_{1-6}$ alkyl)piperazino, N—($C_{1-6}$ alkoxy $C_{3-6}$ alkenyl)piperazino, N—($C_{1-6}$ alkylamino $C_{1-6}$ alkyl)piperazino, N—($C_{1-6}$ alkylamino $C_{3-6}$ alkenyl) piperazino,
wherein the substituents are selected from the group consisting of
  (a) hydroxy, $C_{1-6}$ alkylalkoxy, $C_{1-6}$ alkylamino,
  (b) $C_{3-6}$ alkenyloxy, $C_{3-6}$ alkenylamino, or
  (c) pyrrolidino, piperidino, morpholino, imidazolyl, substituted imidazolyl, piperazino, N—$C_{1-6}$ alkenylpiperazino, N—$C_{3-6}$ alkenylpiperazino, N—($C_{1-6}$ alkoxy $C_{1-6}$ alkyl)piperazino, N—($C_{1-6}$ alkoxy $C_{3-6}$ alkenyl)piperazino, N—($C_{1-6}$ alkylamino $C_{1-6}$ alkyl)piperazino, N—($C_{1-6}$ alkylamino $C_{3-6}$ alkenyl)piperazino,
or $R_2$ and $R_3$ taken together forming an aryl group or substituted aryl wherein the substituents are defined as above in (i)–(v);
and $R_4$ is selected from the group consisting of:
  (i) hydrogen;
  (ii) substituted $C_{1-11}$ alkyl or $C_{2-11}$ alkenyl wherein the substituents are independently selected from the group consisting of hydrogen, hydroxy, $C_{1-6}$ alkyloxy, $C_{1-6}$alkylthio, $C_{1-6}$ alamino, phenyl-$C_{1-6}$ alkylamino, $C_{1-6}$ alkoxycarbonyl; or
  (iii) substituted aryl $C_{0-11}$ alkyl wherein the aryl group is selected from phenyl, imidazolyl, furyl, thienyl in which the substituents are selected from A. (a–c); or
B. when $R_1$ is selected from the group consisting of:
Mono-,di-, and tri-substituted aryl-$C_{0-6}$ alkyl wherein aryl is selected from the group consisting of phenyl, thienyl, and the substituents are selected from the group consisting of:

(a) trans-2-substituted benzimidazolylethenyl, trans-2-substituted benzoxazolylethenyl, trans-2-substituted benzthiazolylethenyl, in which the substituents are selected from the group consisting of hydrogen, hydroxy, halo, trihalomethyl, $C_{1-4}$ alkyl and $C_{1-4}$ alkyloxy, $C_{1-4}$ alkyloxycarbonyl, $C_{1-4}$ alkylamino, di($C_{1-4}$ alkyl)amino, $C_{3-6}$ alkenylamino, di($C_{3-6}$ alkenyl)amino, $C_{1-4}$ alkyloxy-$C_{1-4}$ alkylamino, substituted $C_{1-4}$ alkyl and $C_{1-4}$ alkyloxy, substituted $C_{1-4}$ alkyloxycarbonyl, substituted $C_{1-4}$ alkylamino, di(substituted $C_{1-4}$ alkyl)amino, substituted $C_{3-6}$ alkenylamino, di(substituted $C_{3-6}$ alkenyl)amino, wherein the substituents are as defined above, (b) trans-2-cyano ethenyl, trans-2-alkylsulfonyl ethenyl, trans-2alkenylsulfonyl ethenyl, trans-2- substituted alkylsulfonyl ethenyl, trans-2- substituted alkenylsulfonyl ethenyl, in which the substituents are defined above, (c) $C_{1-6}$ $CO_2R_5$, trans- $CH=CHCO_2R_5$, $C_{1-6}CONHR_5$, or trans-$CH=CHCONHR_5$, wherein $R_5$ is $C_{1-6}$ alkoxy $C_{2-6}$ alkyl, amino $C_{2-6}$ alkyl, $C_{1-6}$ alkylamino $C_{2-6}$ alkyl, di($C_{1-6}$ alkyl)amino $C_{2-6}$ alkyl, $C_{1-6}$ alkylthio $C_{2-6}$ alkyl, substituted $C_{1-6}$ alkoxy $C_{2-6}$ alkyl, substituted $C_{1-6}$ alkylamino $C_{2-6}$ alkyl, di(substituted $C_{1-6}$ alkyl)amino $C_{2-6}$ alkyl, substituted $C_{1-6}$ alkylthio $C_{2-6}$ alkyl, in which the substituents are selected from the group consisting of pyrrolidino, piperidino, morpholino, piperazino, N—$C_{1-6}$ alkenylpiperazino, N—$C_{3-6}$ alkenylpiperazino, N—($C_{1-6}$ alkoxy $C_{1-6}$ alkyl)piperazino, N—($C_{1-6}$ alkoxy $C_{3-6}$ alkenyl)piperazino, N—($C_{1-6}$ alkylamino $C_{1-6}$ alkyl)piperazino, N—($C_{1-6}$ alkylamino $C_{3-6}$ alkenyl)piperazino, imidazolyl, oxazolyl, thiazolyl, (d) $C_{1-6}CONR_6R_7$, or trans- $CH=CHCONR_6R_7$, wherein $R_6$ and $R_7$ are independently selected from the group consisting of $C_{1-6}$ alkyl, phenyl $C_{1-6}$ alkyl, $C_{1-6}$ alkoxycarbonylmethyleneoxy, hydroxy $C_{2-6}$ alkyl, $C_{1-6}$ alkyloxy $C_{2-6}$ alkyl, amino $C_{2-6}$ alkyl, $C_{1-6}$ alkylamino $C_{2-6}$ alkyl, di($C_{1-6}$ alkyl)amino $C_{2-6}$ alkyl, $C_{1-6}$ alkylthio $C_{2-6}$ alkyl, substituted $C_{1-6}$ alkoxy $C_{2-6}$ alkyl, substituted $C_{1-6}$ alkylamino $C_{2-6}$ alkyl, di(substituted $C_{1-6}$ alkyl)amino $C_{2-6}$ alkyl, substituted $C_{1-6}$ alkylthio $C_{2-6}$ alkyl, wherein the substituents are selected from the group consisting of pyrrolidino, piperidino, morpholino, piperazino, N—$C_{1-6}$ alkenylpiperazino, N—$C_{3-6}$ alkenylpiperazino, N—($C_{1-6}$ alkoxy $C_{1-6}$ alkyl)piperazino, N—($C_{1-6}$ alkoxy $C_{3-6}$ alkenyl)piperazino, N—($C_{1-6}$ alkylamino $C_{1-6}$ alkyl)piperazino, N—($C_{1-6}$ alkylamino $C_{3-6}$ alkenyl)piperazino, imidazolyl, oxazolyl, thiazolyl, (e) $R_7$ C(O) $C_{1-6}$ alkyl, $R_7$ C(O) carbonyl $C_{2-6}$ alkenyl, in which $R_7$ is defined as above [2(d)], (f) HO—$C_{1-6}$ alkyl-$C_{2-6}$ alkenyl, $R_7$—O—$C_{1-6}$ alkyl-$C_{2-6}$ alkenyl, $R_7NH$—$C_{1-6}$ alkyl-$C_{2-6}$ alkenyl, $R_6R_7N$—$C_{1-6}$ alkyl-$C_{2-6}$ alkenyl, $R_7NH$—C(O)—O—$C_{1-6}$ alkyl-$C_{2-6}$ alkenyl, $R_6R_7N$—C(O)—O—$C_{1-6}$ alkyl-$C_{2-6}$ alkenyl, $R_7O$—C(O)—O$C_{1-6}$ alkyl-$C_{2-6}$ alkenyl, $R_7$—C(O)—O—$C_{1-6}$ alkyl-$C_{2-6}$ alkenyl, wherein $R_6$ and $R_7$ is defined as above [2(d)], (g) $R_7$—O—$CO_{0-3}$ alkyl-$C_{3-6}$ cycloalkan-1-yl, $R_7NH$—$C_{0-3}$ alkyl- $C_{3-6}$ cycloalkan-1-yl, $R_6R_7N$— $C_{0-3}$ alkyl- $C_{3-6}$ cycloalkan-1-yl, $R_7NH$—C(O)—O— $C_{0-3}$ $C_{3-6}$ cycloalkan-1-yl, $R_6R_7N$—C(O)—O— $C_{0-3}$ alkyl- $C_{3-6}$ cycloalkan-1-yl, $R_7O$—C(O)—O— $C_{0-3}$ alkyl- $C_{3-6}$ cycloalkan-1-yl, $R_7$—C(O)—O— $C_{0-3}$ alkyl- $C_{3-6}$ cycloalkan-1-yl, $R_7O$—C(O)—$C_{0-3}$ alkyl—$C_{3-6}$ cycloalkan-1-yl, wherein $R_7$ and is defined as above [2(d)];

then $R_2$ and $R_3$ are each independently selected from the group consisting of (1) hydrogen, halo, trihalomethyl, $C_{1-6}$ alkyl, substituted $C_{1-6}$ alkyl, $C_{1-6}$ alkenyl, substituted $C_{0-6}$ alkenyl, $C_{1-6}$ alkyloxy, substituted $C_{1-6}$ alkyloxy, $C_{3-6}$ alkenyloxy, substituted $C_{3-6}$ alkenyloxy, $C_{1-6}$ alkylamino, substituted $C_{1-6}$ alkylamino, $C_{3-6}$ alkenylamino, substituted $C_{3-6}$ alkenylamino, (2) mono-, di-, and tri-substituted phenyl wherein the substituents are independently selected from:

(i) halo, trifluoromethyl, substituted $C_{1-6}$ alkyl, (ii) $C_{1-6}$ alkyloxy, substituted $C_{1-6}$ alkyloxy, $C_{3-6}$ alkenyloxy, substituted $C_{3-6}$ alkenyloxy, (iii) $C_{1-6}$ alkyl-amino, di($C_{1-6}$ alkyl)amino, substituted $C_{1-6}$ alkyl-amino, di(substituted $C_{1-6}$ alkyl)amino, $C_{3-6}$ alkenyl-amino, di($C_{3-6}$ alkenyl)amino, substituted $C_{3-6}$ alkenyl-amino, di(substituted $C_{3-6}$ alkenyl)amino,or (iv) pyrrolidino, piperidino, morpholino, imidazolyl, substituted imidazolyl, piperazino, N—$C_{1-6}$ alkenylpiperazino, N—$C_{3-6}$ alkenylpiperazino, N—($C_{1-6}$ alkoxy $C_{1-6}$ alkyl)piperazino, N—($C_{1-6}$ alkoxy $C_{3-6}$ alkenyl)piperazino, N—($C_{1-6}$ alkylamino $C_{1-6}$ alkyl)piperazino, N—($C_{1-6}$ alkylamino $C_{3-6}$ alkenyl)piperazino, wherein the substituents are selected from the group consisting of (a) hydrogen, hydroxy, halo, trifluoromethyl, (b) $C_{1-6}$ alkylalkoxy, $C_{1-6}$ alkylamino, $C_{1-6}$ alkylthio, (c) $C_{3-6}$ alkenyloxy, $C_{3-6}$ alkenylamino, $C_{3-6}$ alkenylthio, or (d) pyrrolidino, piperidino, morpholino, imidazolyl, substituted imidazolyl, piperazino, N—$C_{1-6}$ alkenylpiperazino, N—$C_{3-6}$ alkenylpiperazino, N—($C_{1-6}$ alkoxy $C_{1-6}$ alkyl)piperazino, N—($C_{1-6}$ alkoxy $C_{3-6}$ alkenyl)piperazino, N—(C1-6 alkylamino $C_{1-6}$ alkyl)piperazino, N—($C_{1-6}$ alkylamino $C_{3-6}$ alkenyl)piperazino;

with the proviso that at least one of $R_2$ and $R_3$ group be selected from [B (2)] and the phenyl and the substituents be selected from (ii)–(v) above; or $R_2$ and $R_3$ taken together forming an aryl group such as phenyl, pyridyl, in which the aryl may be optionally substituted, wherein the substituents are defined as above in (i)–(iv);

and $R_4$ is selected from the group consisting of:

(a) hydrogen;

(b) substituted $C_{1-11}$ alkyl or $C_{2-11}$ alkenyl wherein the substituents are independently selected from the group consisting of hydrogen, hydroxy, $C_{1-6}$ alkyloxy, $C_{1-6}$alkylthio, $C_{1-6}$ alkylamino, phenyl-$C_{1-6}$ alkylamino, $C_{1-6}$ alkoxycarbonyl and the substituents are selected from (ii)–(iv); or (c) aryl $C_{0-11}$ alkyl wherein the aryl group is selected from phenyl, imidazolyl, furyl, thienyl.

or its pharmaceutically acceptable salts.

2. A compound according to claim 1 having the following formula:

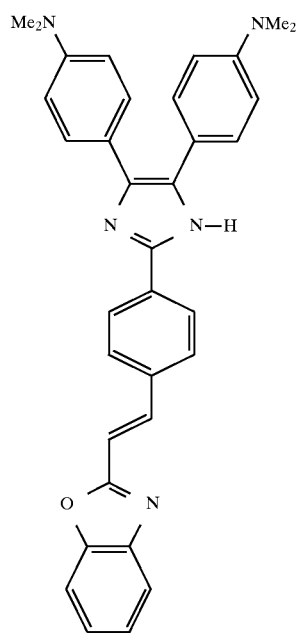

or its pharmaceutically acceptable salts.

3. A compound according to claim 1 having the following formula:

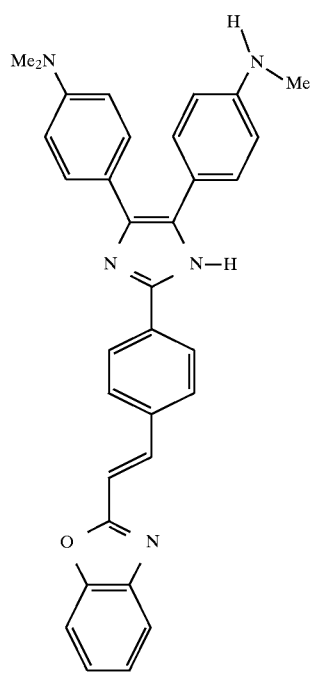

or its pharmaceutically acceptable salts.

4. A compound according to claim 1 having the following formula:

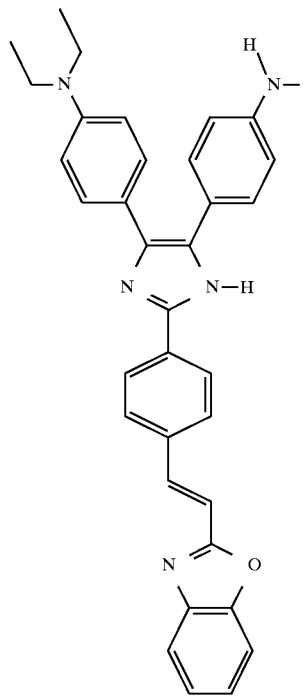

or its pharmaceutically acceptable salts.

5. A compound according to claim 1 having the following formula:

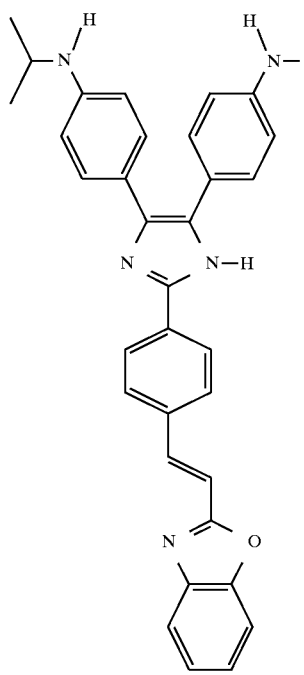

or its pharmaceutically acceptable salts.

6. A compound according to claim 1 having the following formula:

77

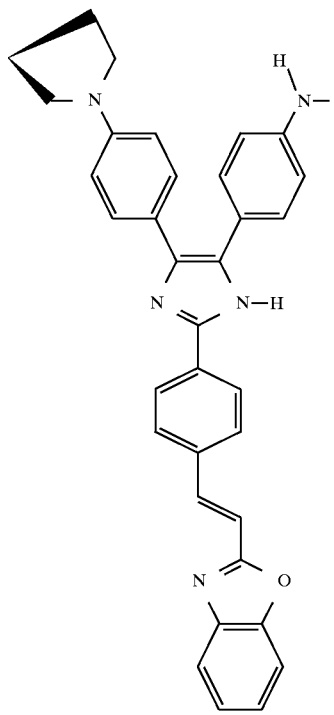

or its pharmaceutically acceptable salts.

7. A compound according to claim 1 having the following formula:

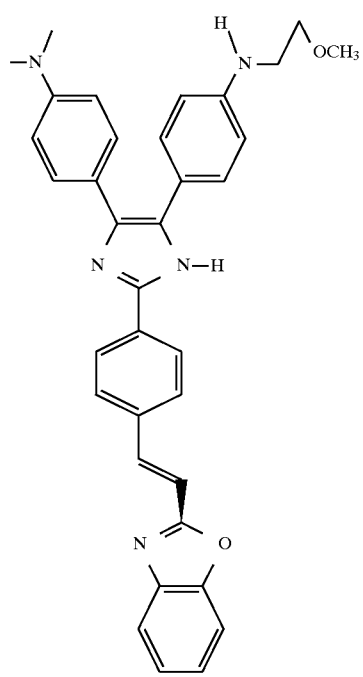

or its pharmaceutically acceptable salts.

8. A compound according to claim 1 having the following formula:

78

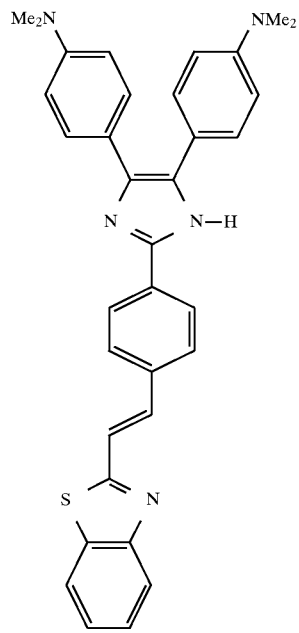

or its pharmaceutically acceptable salts.

9. A compound according to claim 1 having the following formula:

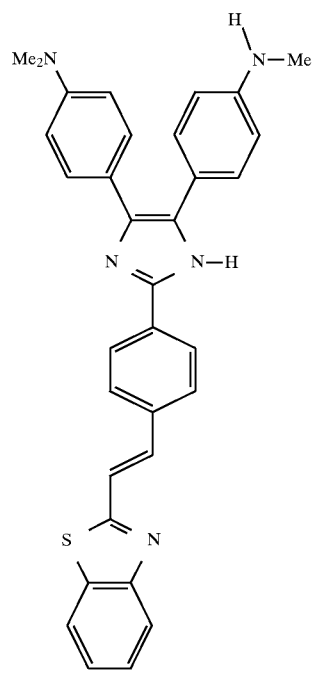

or its pharmaceutically acceptable salts.

10. A compound according to claim 1 having the following formula:

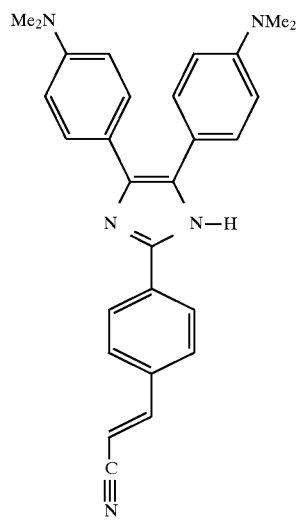

or its pharmaceutically acceptable salts.

11. A compound according to claim 1 having the following formula:

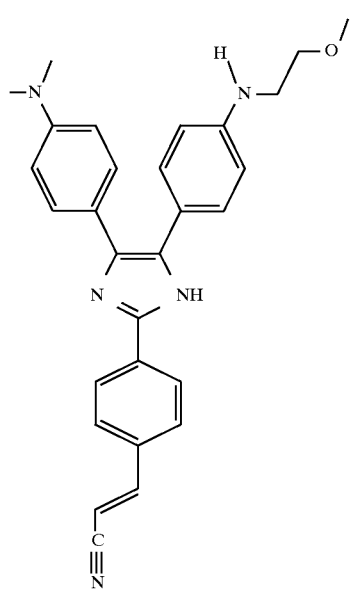

or its pharmaceutically acceptable salts.

12. A compound according to claim 1 having the following formula:

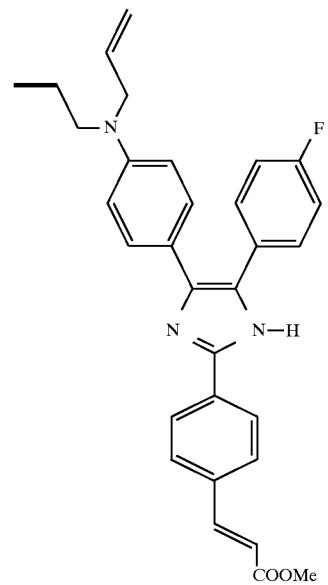

or its pharmaceutically acceptable salts.

13. A compound according to claim 1 having the following formula:

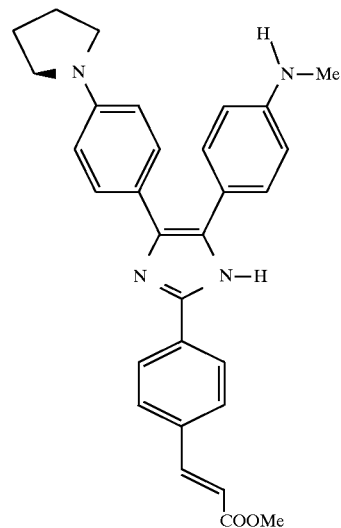

or its pharmaceutically acceptable salts.

14. A compound according to claim 1 having the following formula:

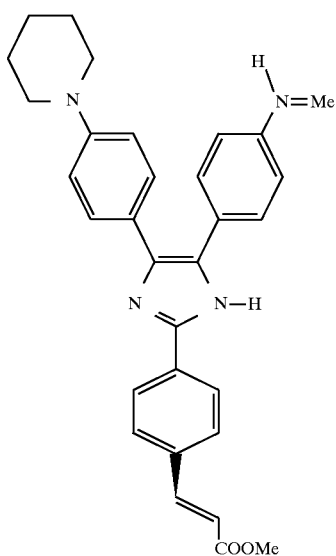
or its pharmaceutically acceptable salts.
15. A compound according to claim 1 having the following formula:
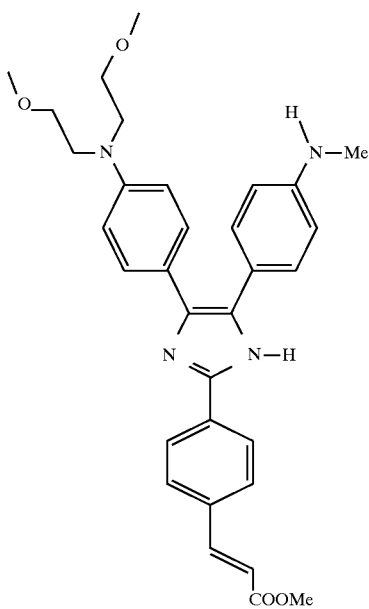
or its pharmaceutically acceptable salts.
16. A compound according to claim 1 having the following formula:
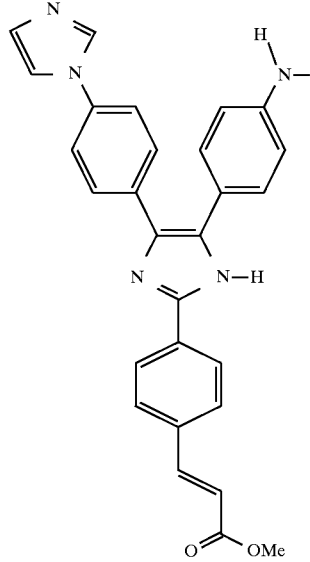
or its pharmaceutically acceptable salts.
17. A compound according to claim 1 having the following formula:
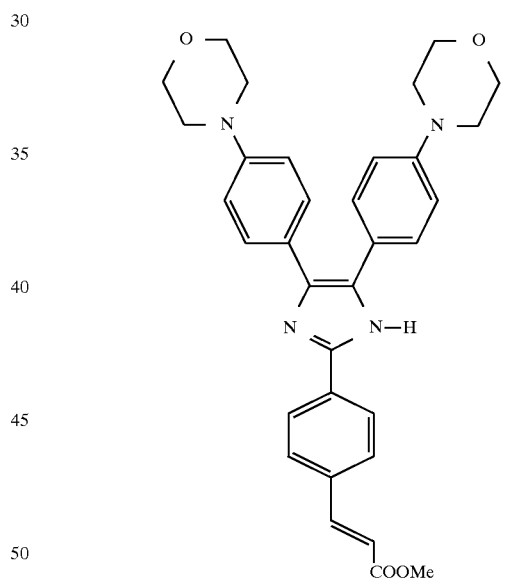
or its pharmaceutically acceptable salts.

18. A compound according to claim 1 having the following formula:

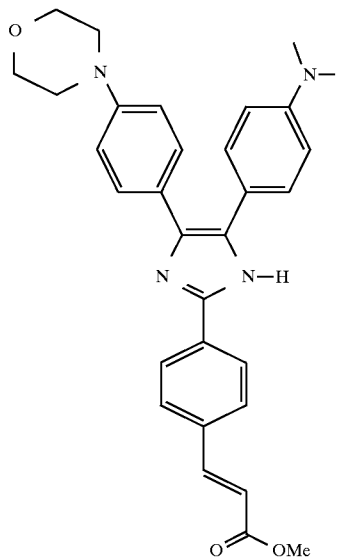

or its pharmaceutically acceptable salts.

19. A compound according to claim 1 having the following formula:

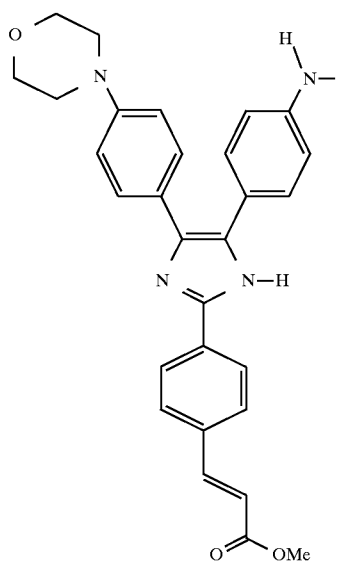

or its pharmaceutically acceptable salts.

20. A compound according to claim 1 having the following formula:

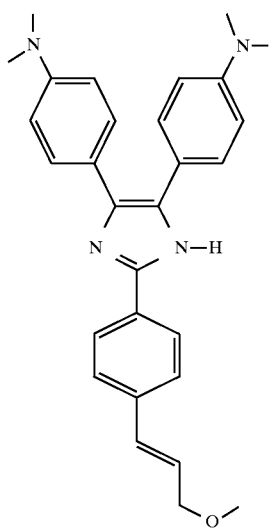

or its pharmaceutically acceptable salts.

21. A compound according to claim 1 having the following formula:

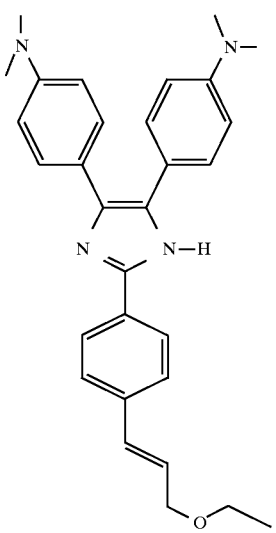

or its pharmaceutically acceptable salts.

22. A compound according to claim 1 having the following formula:

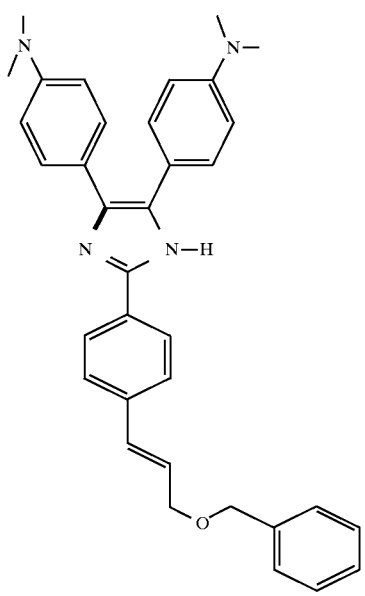
or its pharmaceutically acceptable salts.
23. A compound according to claim 1 having the following formula:
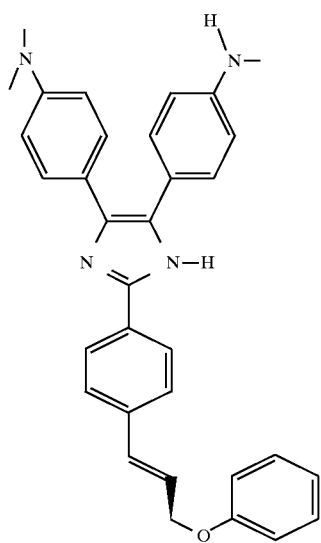
or its pharmaceutically acceptable salts.
24. A compound according to claim 1 having the following formula:
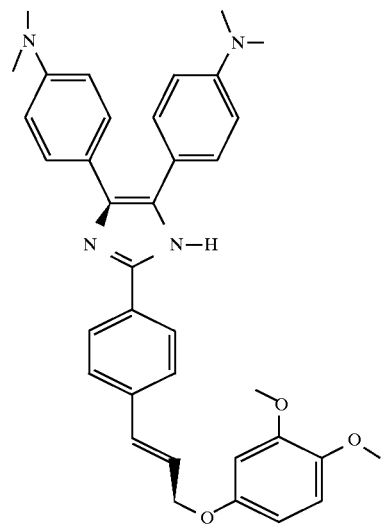
or its pharmaceutically acceptable salts.
25. A compound according to claim 1 having the following formula:
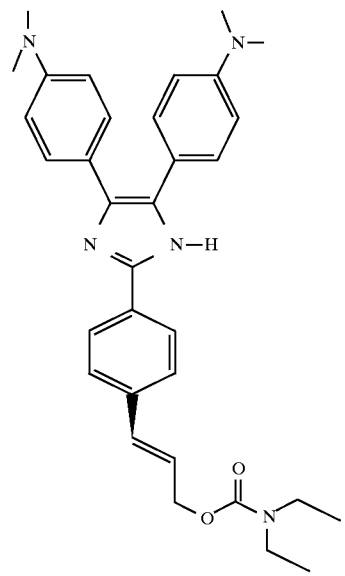
or its pharmaceutically acceptable salts.

26. A compound according to claim 1 having the following formula:

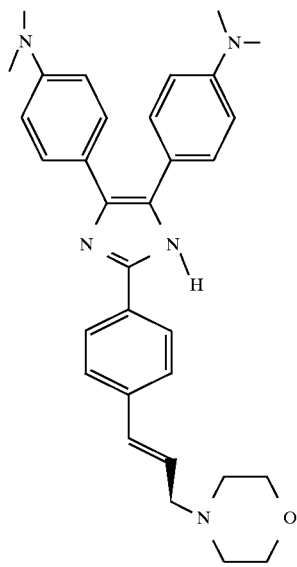

or its pharmaceutically acceptable salts.

27. A compound according to claim 1 having the following formula:

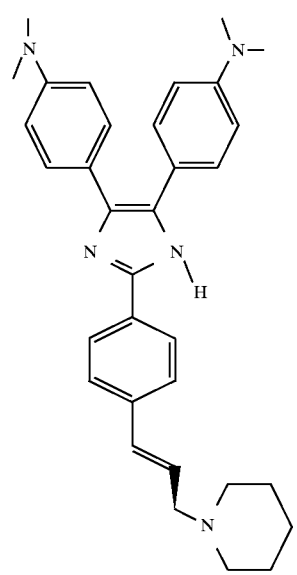

or its pharmaceutically acceptable salts.

28. A compound according to claim 1 having the following formula:

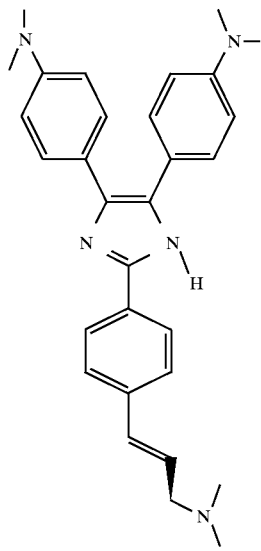

or its pharmaceutically acceptable salts.

29. A compound according to claim 1 having the following formula:

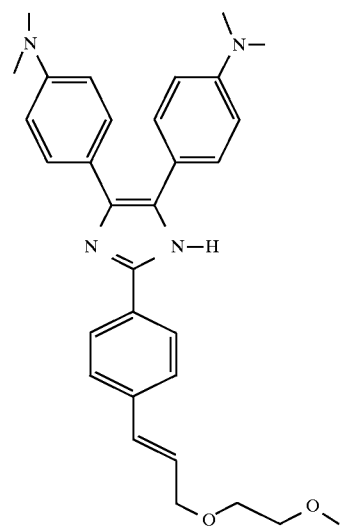

or its pharmaceutically acceptable salts.

30. A compound according to claim 1 having the following formula:

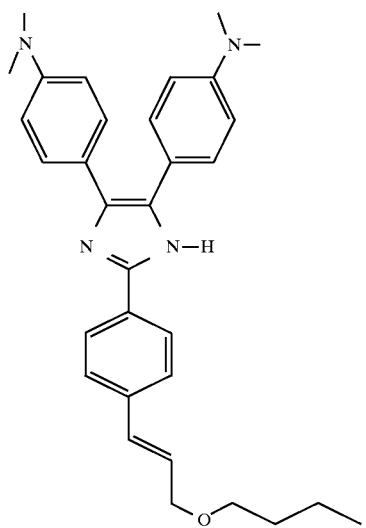

or its pharmaceutically acceptable salts.

31. A compound according to claim 1 having the following formula:

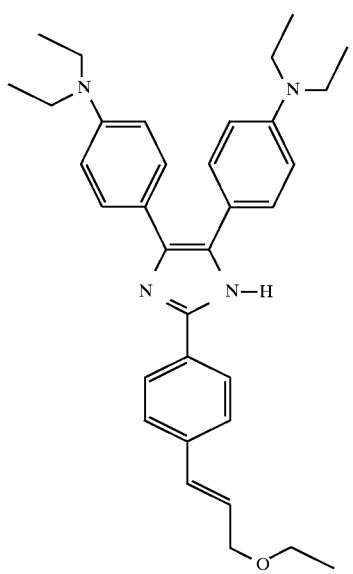

or its pharmaceutically acceptable salts.

32. A compound according to claim 1 having the following formula:

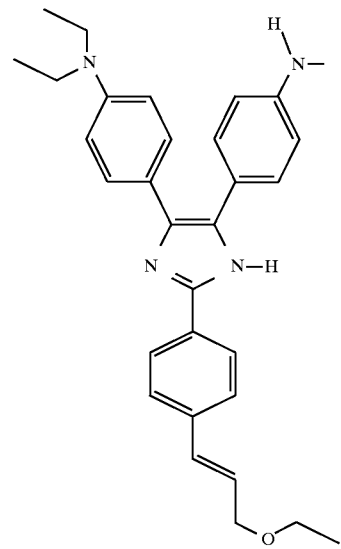

or its pharmaceutically acceptable salts.

33. A compound according to claim 1 having the following formula:

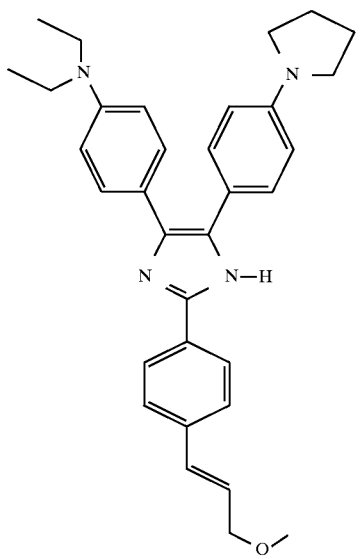

or its pharmaceutically acceptable salts.

34. A compound according to claim 1 having the following formula:

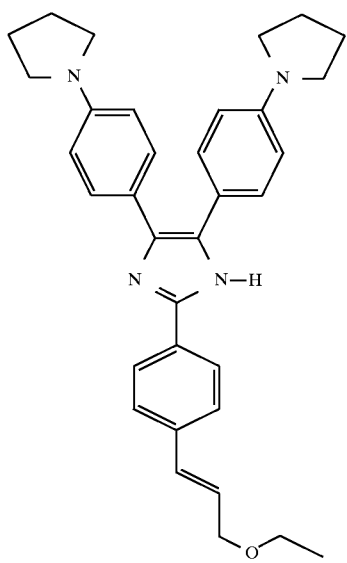

or its pharmaceutically acceptable salts.

35. A compound according to claim 1 having the following formula:

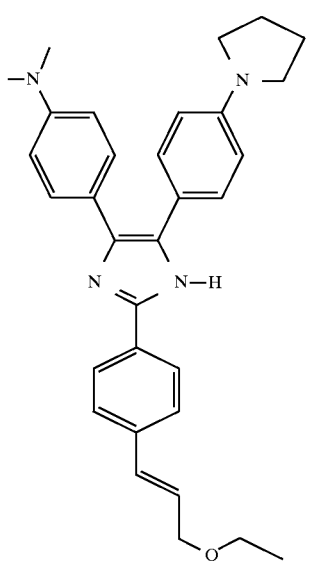

or its pharmaceutically acceptable salts.

36. A compound according to claim 1 having the following formula:

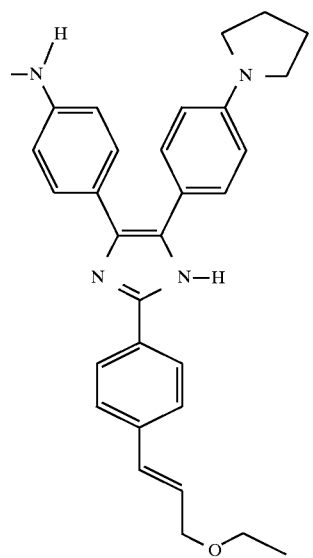

or its pharmaceutically acceptable salts.

37. A compound according to claim 1 having the following formula:

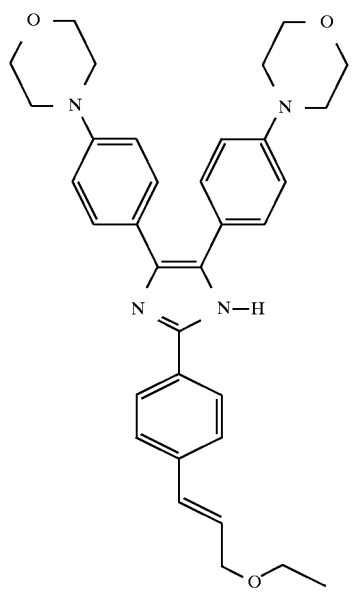

or its pharmaceutically acceptable salts.

38. A compound according to claim 1 having the following formula:

93

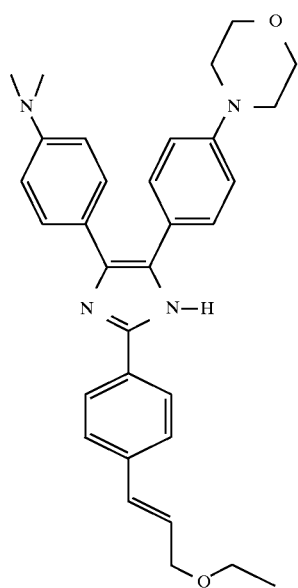

or its pharmaceutically acceptable salts.

39. A compound according to claim 1 having the following formula:

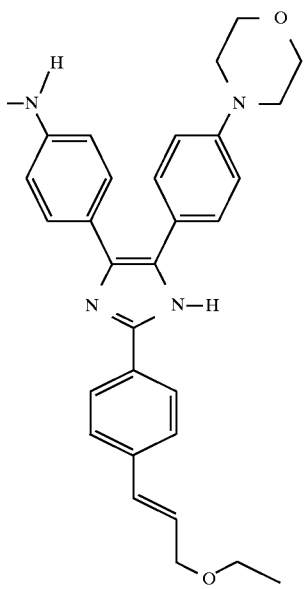

or its pharmaceutically acceptable salts.

94

40. A compound according to claim 1 having the following formula:

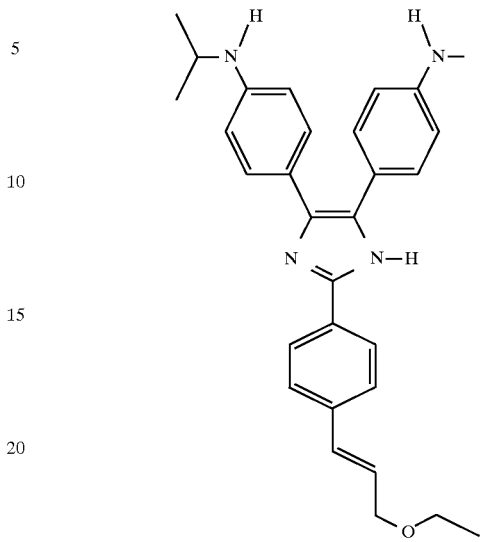

or its pharmaceutically acceptable salts.

41. A compound according to claim 1 having the following formula:

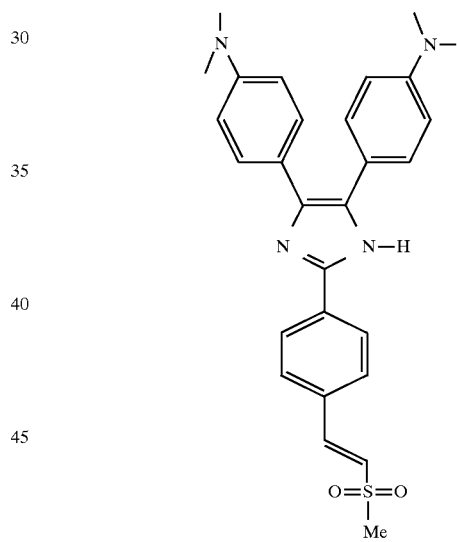

or its pharmaceutically acceptable salts.

42. A compound according to claim 1 having the following formula:

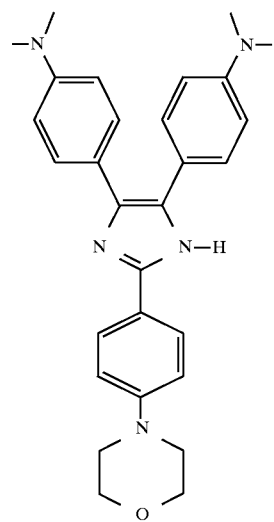

or its pharmaceutically acceptable salts.

43. A compound according to claim 1 having the following formula:

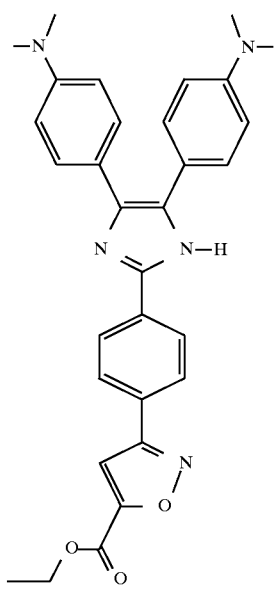

or its pharmaceutically acceptable salts.

44. A compound according to claim 1 having the following formula:

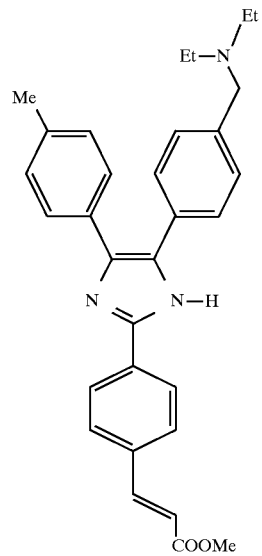

or its pharmaceutically acceptable salts.

45. A compound according to claim 1 having the following formula:

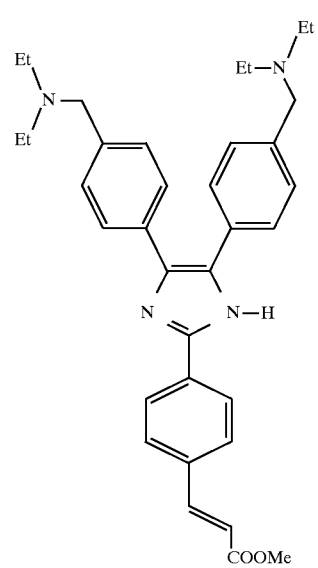

or its pharmaceutically acceptable salts.

46. A compound according to claim 1 having the following formula:

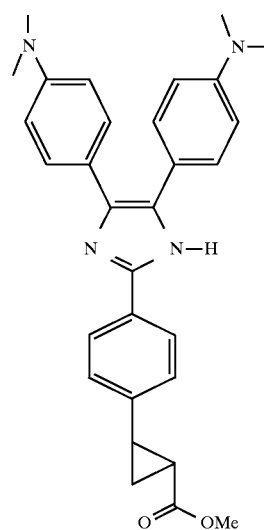

or its pharmaceutically acceptable salts.

47. A compound according to claim 1 having the following formula:

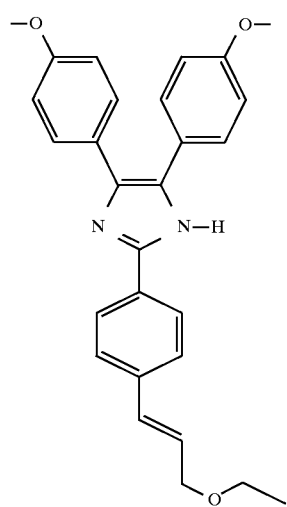

or its pharmaceutically acceptable salts.

48. A compound according to claim 1 having the following formula:

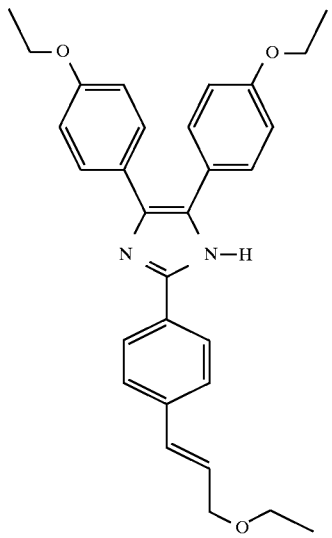

or its pharmaceutically acceptable salts.

49. A compound according to claim 1 having the following formula:

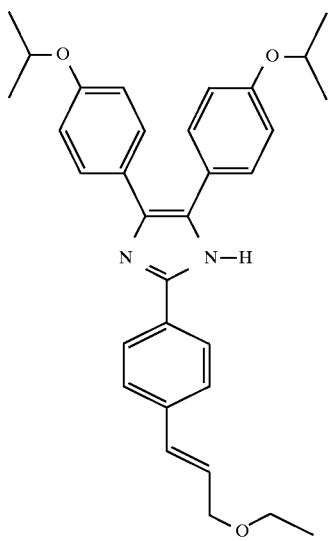

or its pharmaceutically acceptable salts.

50. A compound according to claim 1 having the following formula:

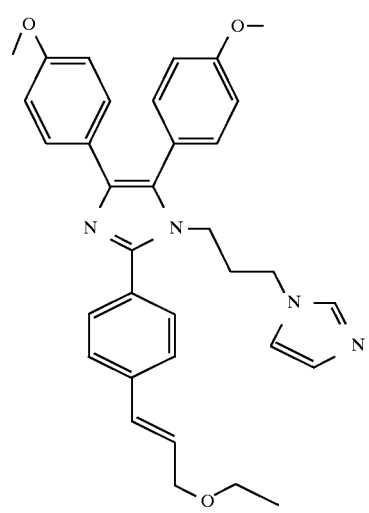

or its pharmaceutically acceptable salts.

51. A compound according to claim 1 having the following formula:

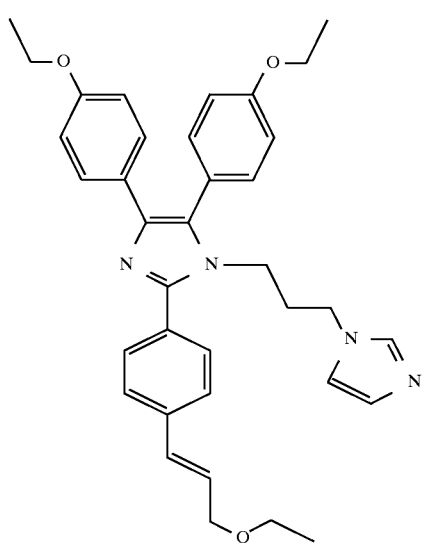

or its pharmaceutically acceptable salts.

52. A compound according to claim 1 having the following formula:

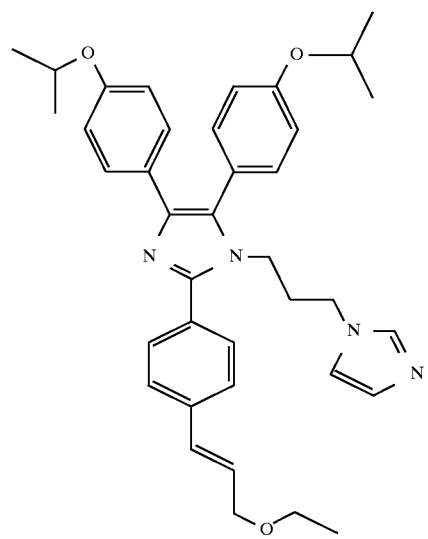

or its pharmaceutically acceptable salts.

53. A compound according to claim 1 having the following formula:

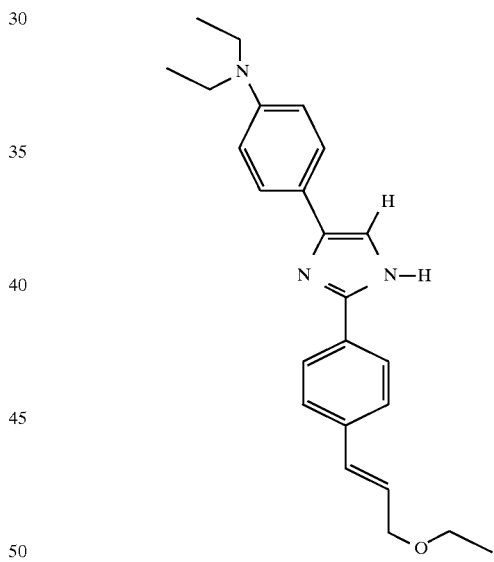

or its pharmaceutically acceptable salts.

54. A compound according to claim 1 having the following formula:

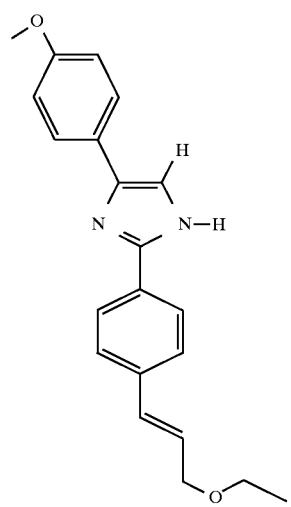
or its pharmaceutically acceptable salts.
55. A compound according to claim 1 having the following formula:
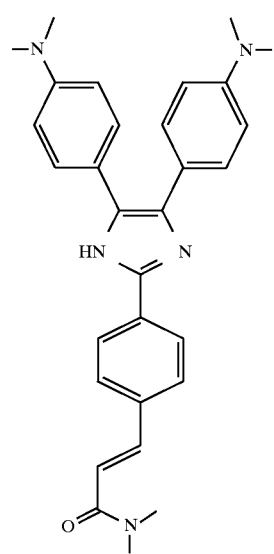
or its pharmaceutically acceptable salts.
56. A compound according to claim 1 having the following formula:
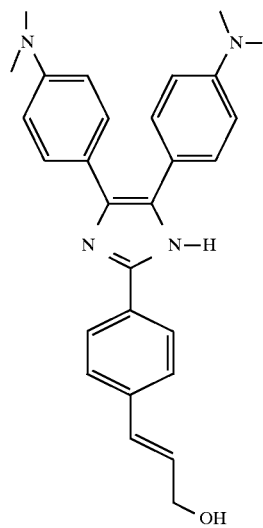
or its pharmaceutically acceptable salts.
57. A compound according to claim I having the following formula:
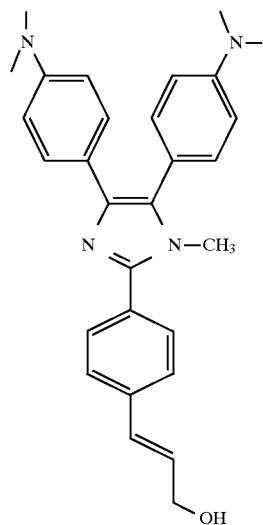
or its pharmaceutically acceptable salts.

58. A compound according to claim 1 having the following formula:

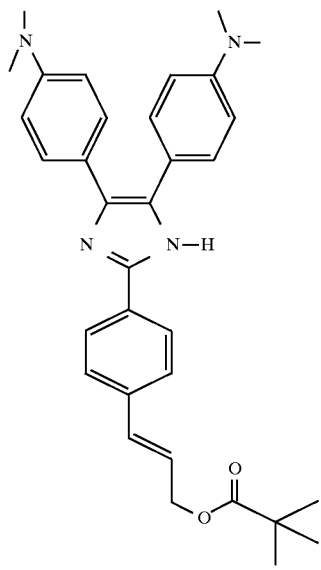

or its pharmaceutically acceptable salts.

59. A compound according to claim 1 having the following formula:

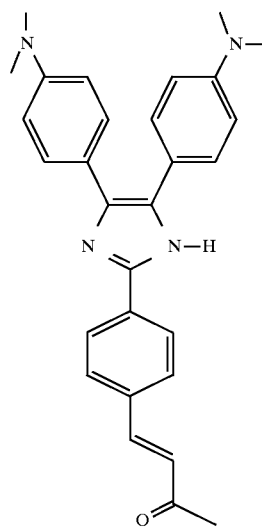

or its pharmaceutically acceptable salts.

60. A compound according to claim 1 having the following formula:

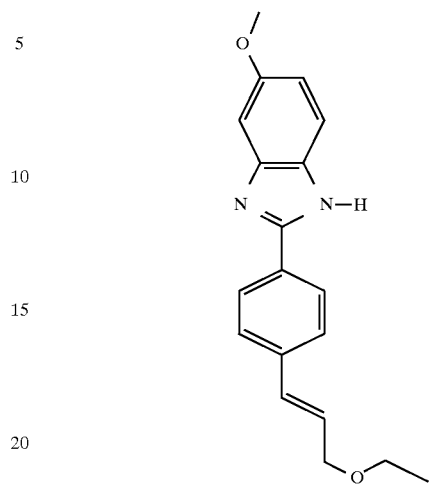

or its pharmaceutically acceptable salts.

61. A compound according to claim 1 having the following formula:

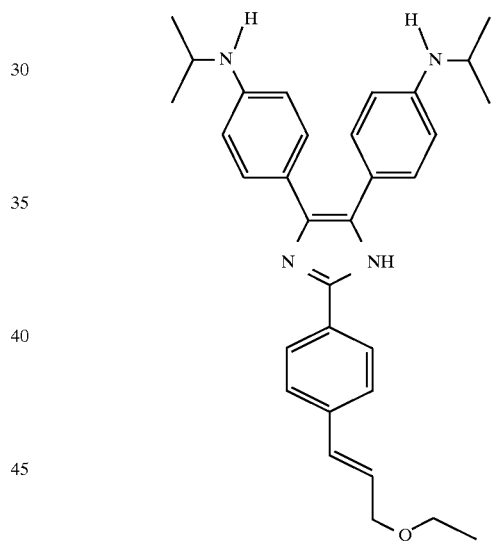

or its pharmaceutically acceptable salts.

62. A compound according to claim 1 having the following formula:

105

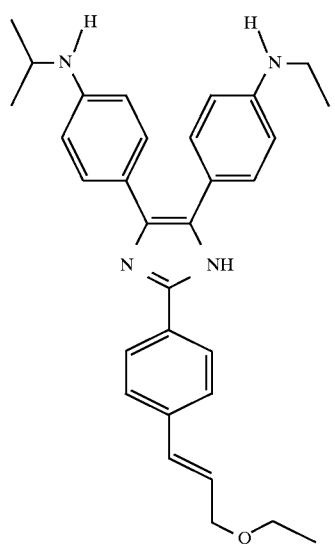

or its pharmaceutically acceptable salts.

63. A compound according to claim 1 having the following formula:

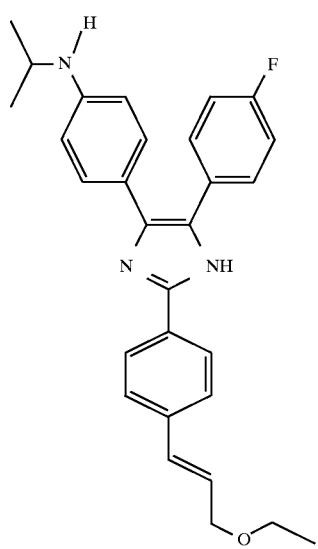

or its pharmaceutically acceptable salts.

64. A compound according to claim 1 having the following formula:

106

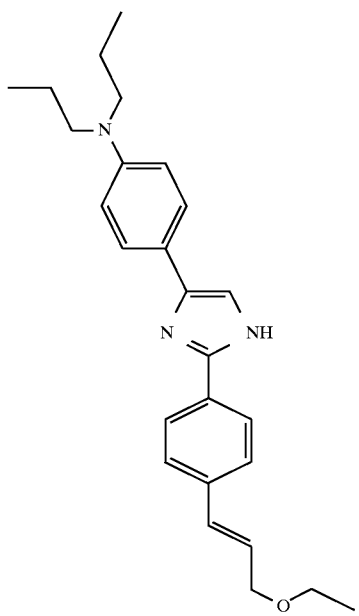

or its pharmaceutically acceptable salts.

65. A compound according to claim 1 having the following formula:

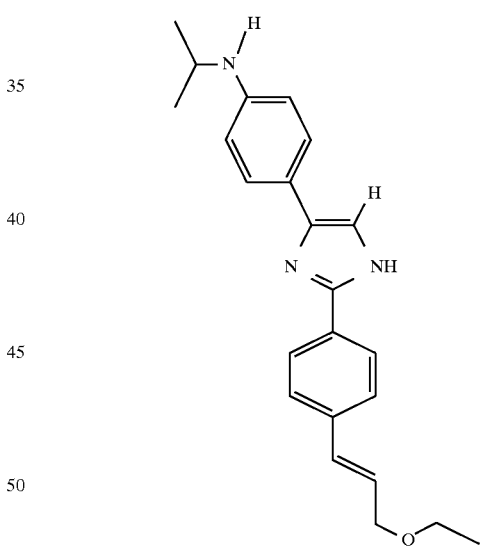

or its pharmaceutically acceptable salts.

66. A compound according to claim 1 having the following formula:

107

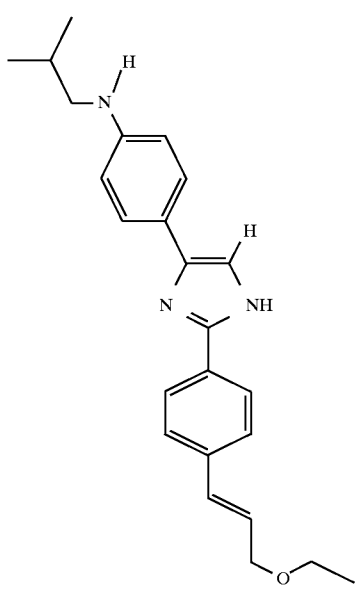

or its pharmaceutically acceptable salts.

67. A compound according to claim 1 having the following formula:

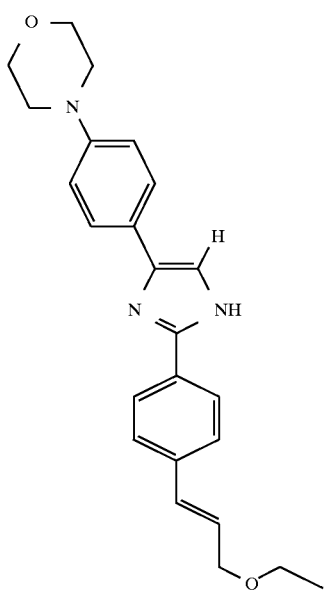

or its pharmaceutically acceptable salts.

68. A compound according to claim 1 having the following formula:

108

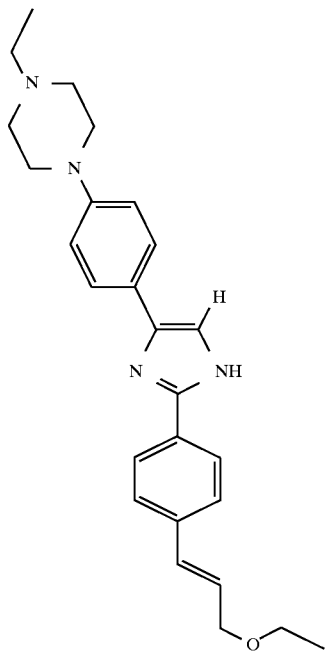

or its pharmaceutically acceptable salts.

69. A compound according to claim 1 having the following formula:

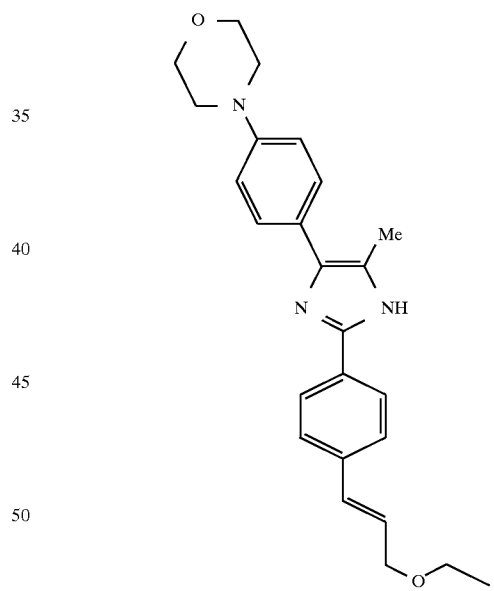

or its pharmaceutically acceptable salts.

70. A method of treatment for increasing the sensitivity of tumor cells to anti-cancer chemotherapeutic agents, said tumor cells being susceptible to anticancer chemotherapeutic agents, and said tumor cells having become resistant to chemotherapy comprising administration to a mammalian species in need of such treatment a therapeutically effective amount of a compound of claim 1 and a pharmaceutically acceptable carrier.

71. A method of treatment of tumor cells, said tumor cells being susceptible to anti-cancer chemotherapeutic agents, and said tumor cells having become resistant to chemotherapy comprising: administration to a mammalian species in need of such treatment, of a therapeutically effective amount of said anti-cancer chemotherapeutic agent, and an effective amount of a compound of claim 1.

72. A method of treatment of tumor cells, comprising: administration to a mammalian species in need of such treatment a therapeutically effective amount of an anti-cancer chemotherapeutic agent selected from the group consisting of taxol, vinblastine, vincristine, daunorubicin, and doxorubicin and an effective amount of a compound according to claim 62.

73. A pharmaceutical composition for increasing the sensitivity of tumor cells to anti-cancer chemotherapeutic agents, said tumors cells having become resistant to chemotherapy comprising a therapeutically effective amount of a compound of claim 1 and a pharmaceutically acceptable carrier.

74. A pharmaceutical composition for increasing the sensitivity of tumor cells to anti-cancer chemotherapeutic agents, said tumors cells having become resistant to chemotherapy comprising: a therapeutically effective amount of an anti-cancer chemotherapeutic agent selected from the group consisting of taxol, vinblastine, vincristine, daunorubicin, and doxorubicin, an effective amount of a compound of claim 1, and a pharmaceutically acceptable carrier.

* * * * *